US007399829B2

(12) United States Patent
Desjarlais et al.

(10) Patent No.: US 7,399,829 B2
(45) **Date of Patent: *Jul. 15, 2008**

(54) VARIANTS OF RANKL PROTEIN

(75) Inventors: John R. Desjarlais, Pasadena, CA (US); Jamal El Yazal, Alta Loma, CA (US); Rene S. Hubert, Los Angeles, CA (US); Shannon A. Marshall, San Francisco, CA (US)

(73) Assignee: Xencor, Inc., Monrovia, CA (US)

( * ) Notice: Subject to any disclaimer, the term of this patent is extended or adjusted under 35 U.S.C. 154(b) by 803 days.

This patent is subject to a terminal disclaimer.

(21) Appl. No.: 10/338,785

(22) Filed: Jan. 6, 2003

(65) Prior Publication Data

US 2003/0219864 A1 Nov. 27, 2003

Related U.S. Application Data

(60) Provisional application No. 60/373,453, filed on Apr. 17, 2002, provisional application No. 60/345,805, filed on Jan. 4, 2002.

(51) Int. Cl.

| | |
|---|---|
| ***C07K 14/00*** | (2006.01) |
| ***C12N 15/00*** | (2006.01) |
| ***C12N 5/00*** | (2006.01) |
| ***A61K 38/00*** | (2006.01) |
| ***C07H 21/00*** | (2006.01) |

(52) U.S. Cl. .................. 530/350; 435/69.1; 435/320.1; 435/325; 514/12; 536/23.5

(58) Field of Classification Search ...................... None
See application file for complete search history.

(56) References Cited

U.S. PATENT DOCUMENTS

| | | | | |
|---|---|---|---|---|
| 5,843,678 | A | 12/1998 | Boyle | |
| 6,017,729 | A | 1/2000 | Anderson et al. | |
| 6,242,213 | B1 | 6/2001 | Anderson | |
| 6,316,408 | B1 | 11/2001 | Boyle | |
| 6,645,500 | B1 * | 11/2003 | Halkier et al. | 424/185.1 |
| 2002/0061525 | A1 | 5/2002 | Rodrigo et al. | |
| 2003/0013651 | A1 | 1/2003 | Lam et al. | |

FOREIGN PATENT DOCUMENTS

| | | | |
|---|---|---|---|
| WO | WO 99/12965 | A | 3/1999 |
| WO | WO 99/29865 | A3 | 6/1999 |
| WO | WO 00/15807 | A | 3/2000 |
| WO | WO 00/15807 | A1 | 3/2000 |
| WO | WO 00/67034 | A | 11/2000 |
| WO | WO 01/25277 | A | 4/2001 |
| WO | WO 01/42298 | A | 4/2001 |
| WO | WO 01/64889 | A | 9/2001 |
| WO | WO 2004/089982 | A | 10/2001 |
| WO | WO 02/18445 | | 3/2002 |
| WO | WO 02/36141 | A | 5/2002 |
| WO | WO 03/006154 | A | 1/2003 |
| WO | WO 03/029420 | A | 4/2003 |
| WO | WO 03/033663 | A2 | 4/2003 |
| WO | WO 03/033664 | A2 | 4/2003 |
| WO | WO 03/059281 | A | 7/2003 |
| WO | WO 2004/081043 | A | 9/2004 |
| WO | WO 2005/035570 | A | 4/2005 |

OTHER PUBLICATIONS

Wells, Additivity of mutational effects in proteins. Biochemistry 29:8509-8517 (1990).*

Ngo et al., The Protein Folding Problem and Tertiary Structure Prediction, pp. 433-440 and 492-495 (1994).*

Adler SH, and Turka LA. "Immunotherapy as a means to induce transplantation tolerance." Curr Opin Immunol. Oct. 2002;14(5):660-5.

Alatalo SL, et al., "Rapid screening method of osteoclast differentiation in vitro that measures tartrate-resistant acid phosphatase 5b activity secreted into the culture medium." Clin Chem. Nov. 2000;46(11):1751-4.

Anderson DM, et al., "A homologue of the TNF receptor and its ligand enhance T-cell growth and dendritic-cell function." Nature. Nov. 13, 1997;390(6656):175-9.

Arron Jr, and Choi Y. "Bone versus immune system." Nature. Nov. 30, 2000;408(6812):535-6.

Atkins GJ, et al. "Osteoprotegerin inhibits osteoclast formation and bone resorbing activity in giant cell tumors of bone." Bone. Apr. 2001;28(4):370-7.

Bachmann MF, and Kopf M. "Balancing protective immunity and immunopathology." Curr Opin Immunol. Aug. 2002;14(4):413-9.

Bianchi L, et al., "A cluster region of AP-1 responsive elements is required for transcriptional activity of mouse ODC gene by hepatocyte growth factor." Arch Biochem Biophys. May 1, 2002;401(1):115-23.

Bodmer JL, et al., "The molecular architecture of the TNF superfamily." Trends Biochem Sci. Jan. 2002;27(1):19-26.

Childs LM, et al., "In vivo RANK signaling blockade using the receptor activator of NF-kappaB:Fc effectively prevents and ameliorates wear debris-induced osteolysis via osteoclast depletion without inhibiting osteogenesis." J Bone Miner Res. Feb. 2002;17(2):192-9.

Collin-Osdoby P, et al. "Receptor activator of NF-kappa B and osteoprotegerin expression by human microvascular endothelial cells, regulation by inflammatory cytokines, and role in human osteoclastogenesis." J Biol Chem. Jun. 8, 2001;276(23):20659-72.

Compston JE. "Bone marrow and bone: a functional unit." J Endocrinol. Jun. 2002;173(3):387-94.

Curotto de Lafaille Ma, and Lafaille JJ. "CD4(+) regulatory T cells in autoimmunity and allergy." Curr Opin Immunol. Dec. 2002;14(6):771-8.

Darnay BG, et al., "Characterization of the intracellular domain of receptor activator of NF-kappaB (RANK). Interaction with tumor necrosis factor receptor-associated factors and activation of NF-kappab and c-Jun N-terminal kinase." J Biol Chem. Aug. 7, 1998;273(32):20551-5.

(Continued)

*Primary Examiner*—Marianne P. Allen
*Assistant Examiner*—Regina Deberry
(74) *Attorney, Agent, or Firm*—Robin M. Silva; Morgan Lewis & Bockius LLP

(57) ABSTRACT

The present invention relates to novel, soluble, recombinant variants RANKL (Receptor Activator of Nuclear Factor—κB Ligand) proteins, which may be expressed solubly in *E. coli,* variants that act as RANKL antagonists, and methods for generating the same.

12 Claims, 30 Drawing Sheets

OTHER PUBLICATIONS

Deyama Y, et al. "Histamine stimulates production of osteoclast differentiation factor/receptor activator of nuclear factor-kappaB ligand by osteoblasts." Biochem Biophys Res Commun. Oct. 25, 2002;298(2):240-6.

Fata JE, et al., "The osteoclast differentiation factor osteoprotegerin-ligand is essential for mammary gland development." Cell. Sep. 29, 2000;103(1):41-50.

Gao YH, et al. "Potential role of cbfa1, an essential transcriptional factor for osteoblast differentiation, in osteoclastogenesis: regulation of mRNA expression of osteoclast differentiation factor (ODF)." Biochem Biophys Res Commun. Nov. 27, 1998;252(3):697-702.

Goater JJ, et al., "Efficacy of ex vivo OPG gene therapy in preventing wear debris induced osteolysis." J Orthop Res. Mar. 2002;20(2):169-73.

Good CR, et al., "Immunohistochemical study of receptor activator of nuclear factor kappa-B ligand (RANK-L) in human osteolytic bone tumors," J Surg Oncol. Mar. 2002;79(3):174-9.

Gori F, et al., "The expression of osteoprotegerin and RANK ligand and the support of osteoclast formation by stromal-osteoblast lineage cells is developmentally regulated." Endocrinology. Dec. 2000;141(12):4768-76.

Gowen M et al., "Emerging therapies for osteoporosis," Exp. Opin. on Emerging Drugs 2000 5(1):1-43.

Gravallese EM, et al., "The role of TNF-receptor family members and other TRAF-dependent receptors in bone resorption." Arthritis Res. 2001;3(1):6-12.

Hofbauer LC, et al., "Interleukin-1beta and tumor necrosis factor-alpha, but not interleukin-6, stimulate osteoprotegerin ligand gene expression in human osteoblastic cells." Bone. Sep. 1999;25(3):255-9.

Hofbauer LC, et al., "Receptor activator of nuclear factor-kappaB ligand and osteoprotegerin: potential implications for the pathogenesis and treatment of malignant bone diseases." Cancer. Aug. 1, 2001;92(3):460-70.

Honore P, et al., "Osteoprotegerin blocks bone cancer-induced skeletal destruction, skeletal pain and pain-related neurochemical reorganization of the spinal cord," Nat Med. May 2000;6(5):521-8.

Hotokezaka H, et al. "U0126 and PD98059, specific inhibitors of MEK, accelerate differentiation of RAW264.7 cells into osteoclast-like cells." J Biol Chem. Dec. 6, 2002;277(49):47366-72.

Hsu H, et al., " Tumor necrosis factor receptor family member RANK mediates osteoclast differentiation and activation induced by osteoprotegerin ligand." Proc Natl Acad Sci U S A. Mar. 30, 1999;96(7):3540-5.

Huber DM, et al., "Androgens suppress osteoclast formation induced by RANKL and macrophage-colony stimulating factor." Endocrinology. Sep. 2001;142(9):3800-8.

Ikeda T, et al., "Determination of three isoforms of the receptor activator of nuclear factor-kappaB ligand and their differential expression in bone and thymus." Endocrinology. Apr. 2001;142(4):1419-26.

Ito S, et al., "Crystal structure of the extracellular domain of mouse RANK ligand at 2.2-A resolution." J Biol Chem. Feb. 22, 2002;277(8):6631-6.

Kaneda T, et al., "Endogenous production of TGF-beta is essential for osteoclastogenesis induced by a combination of receptor activator of NF-kappa B ligand and macrophage-colony-stimulating factor." J Immunol. Oct. 15, 2000;165(8):4254-63.

Kitazawa R, and Kitazawa S. "Vitamin D(3) augments osteoclastogenesis via vitamin D-responsive element of mouse RANKL gene promoter." Biochem Biophys Res Commun. Jan. 18, 2002;290(2):650-5.

Kitazawa R, et al., "Promoter structure of mouse RANKL/TRANCE/OPGL/ODF gene." Biochim Biophys Acta. Apr. 14, 1999;1445(1):134-41.

Kong YY, et al., "Activated T cells regulate bone loss and joint destruction in adjuvant arthritis through osteoprotegerin ligand." Nature. Nov. 18, 1999;402(6759):304-9.

Lacey DL, et al., "Osteoprotegerin ligand is a cytokine that regulates osteoclast differentiation and activation." Cell. Apr. 17, 1998;93(2):165-76.

Lam J, et al. "TNF-alpha induces osteoclastogenesis by direct stimulation of macrophages exposed to permissive levels of RANK ligand." J Clin Invest. Dec. 2000;106(12):1481-8.

Lam J, et al., "Crystal structure of the TRANCE/RANKL cytokine reveals determinants of receptor-ligand specificity." J Clin Invest. Oct. 2001;108(7):971-9.

Lark MW, and James IE. "Novel bone antiresorptive approaches." Curr Opin Pharmacol. Jun. 2002;2(3):330-7.

Lean JM, et al., "Osteoclast lineage commitment of bone marrow precursors through expression of membrane-bound TRANCE." Bone. Jul. 2000;27(1):29-40.

Li J, et al., "RANK is the intrinsic hematopoietic cell surface receptor that controls osteoclastogenesis and regulation of bone mass and calcium metabolism." Proc Natl Acad Sci U S A. Feb. 15, 2000;97(4):1566-71.

Liu Y, et al. "Crystal structure of sTALL-1 reveals a virus-like assembly of TNF family ligands." Cell. Feb. 8, 2002;108(3):383-94.

Locksley RM, et al., "The TNF and TNF receptor superfamilies: integrating mammalian biology." Cell. Feb. 23, 2001;104(4):487-501.

Lum L, et al. "Evidence for a role of a tumor necrosis factor-alpha (TNF-alpha)-converting enzyme-like protease in shedding of TRANCE, a TNF family member involved in osteoclastogenesis and dendritic cell survival." J Biol Chem. May 7, 1999;274(19):13613-8.

Martin TJ, and Gillespie MT. "Receptor activator of nuclear factor kappa B ligand (RANKL): another link between breast and bone." Trends Endocrinol Metab. Jan.-Feb. 2001;12(1):2-4.

Matsuzaki K, et al., "Osteoclast differentiation factor (ODF) induces osteoclast-like cell formation in human peripheral blood mononuclear cell cultures." Biochem Biophys Res Commun. May 8, 1998;246(1):199-204.

McHugh KP, et al. "Mice lacking beta3 integrins are osteosclerotic because of dysfunctional osteoclasts." J Clin Invest. Feb. 2000;105(4):433-40.

Menaa C, et al., "Enhanced RANK ligand expression and responsivity of bone marrow cells in Paget's disease of bone." J Clin Invest. Jun. 2000;105(12):1833-8.

Nakagawa N, et al., "RANK is the essential signaling receptor for osteoclast differentiation factor in osteoclastogenesis." Biochem Biophys Res Commun. Dec. 18, 1998;253(2):395-400.

Nakashima T, et al. "Protein expression and functional difference of membrane-bound and soluble receptor activator of NF-kappaB ligand: modulation of the expression by osteotropic factors and cytokines." Biochem Biophys Res Commun. Sep. 7, 2000;275(3):768-75.

Oyajobi BO, et al., "Therapeutic efficacy of a soluble receptor activator of nuclear factor kappaB-IgG Fc fusion protein in suppressing bone resorption and hypercalcemia in a model of humoral hypercalcemia of malignancy." Cancer Res. Mar. 15, 2001;61(6):2572-8.

Penninger, Josef, "Bones, Lymphocytes, and Mammalian Evolution," Society for Biomolecular Screening 8th Annual Conference, The Hague, The Netherlands, Sep. 22-26, 2002 (Abstract).

Quinn JM, et al., "A combination of osteoclast differentiation factor and macrophage-colony stimulating factor is sufficient for both human and mouse osteoclast formation in vitro." Endocrinology, Oct. 1998;139(10):4424-7.

Quinn JM, et al., "The generation of highly enriched osteoclast-lineage cell populations." Bone. Jan. 2002;30(1):164-70.

Rodan GA, and Martin TJ. "Therapeutic approaches to bone diseases." Science. Sep. 1, 2000;289(5484):1508-14.

Romas E, et al., "Involvement of receptor activator of NFkappaB ligand and tumor necrosis factor-alpha in bone destruction in rheumatoid arthritis." Bone. Feb. 2002;30(2):340-6.

Sabokbar A, et al., "Two distinct cellular mechanisms of osteoclast formation and bone resorption in periprosthetic osteolysis." J Orthop Res. Jan. 2003;21(1):73-80.

Saidenberg Kermanac'H N, et al., "Osteoprotegerin and inflammation." Eur Cytokine Netw. Apr.-Jun. 2002;13(2):144-53.

Schlondorff J, et al., "Biochemical and pharmacological criteria define two shedding activities for TRANCE/OPGL that are distinct from the tumor necrosis factor alpha convertase." J Biol Chem. May 4, 2001;276(18):14665-74.

Schoppet M, et al., "RANK ligand and osteoprotegerin: paracrine regulators of bone metabolism and vascular function." Arterioscler Thromb Vasc Biol. Apr. 1, 2002;22(4):549-53.

Senior K. "Vaccinating against bone destruction." Drug Discov Today. Dec. 15, 2001;6(24):1243-1244.

Shevde NK, et al., "Estrogens suppress RANK ligand-induced osteoclast differentiation via a stromal cell independent mechanism involving c-Jun repression." Proc Natl Acad Sci U S A. Jul. 5, 2000;97(14):7829-34.

Srivastava S, et al., "Estrogen decreases osteoclast formation by down-regulating receptor activator of NF-kappa B ligand (RANKL)-induced JNK activation." J Biol Chem. Mar. 23, 2001;276(12):8836-40.

Suda T, et al., Modulation of osteoclast differentiation and function by the new members of the tumor necrosis factor receptor and ligand families. Endocr Rev. Jun. 1999;20(3):345-57.

Takahashi N, et al., "A new member of tumor necrosis factor ligand family , ODF/OPGL/TRANCE/RANKL, regulates osteoclast differentiation and function." Biochem Biophys Res Commun. Mar. 24, 1999;256(3):449-55.

Takayanagi H, et al, "RANKL maintains bone homeostasis through c-Fos-dependent induction of interferon-beta." Nature. Apr. 18, 2002;416(6882):744-9.

Takayanagi H, et al., "Signaling crosstalk between RANKL and interferons in osteoclast differentiation." Arthritis Res. 2002;4 Suppl 3:S227-32.

Teitelbaum SL. "Bone resorption by osteoclasts." Science. Sep. 1, 2000;289(5484):1504-8.

Theill LE, et al. "RANK-L and RANK: T cells, bone loss, and mammalian evolution." Annu Rev Immunol. 2002;20:795-823.

Tsuda E, et al., "Isolation of a novel cytokine from human fibroblasts the specifically inhibits osteoclastogenesis." Biochem Biophys Res Commun. May 8, 1997;234(1):137-42.

Udagawa N, et al., "Origin of osteoclasts: mature monocytes and macrophages are capable of differentiating into osteoclasts under a suitable microenvironment prepared by bone marrow-derived stromal cells." Proc Natl Acad Sci U S A. Sep. 1990;87(18):7260-4.

Vanderkerken K, et al., "Recombinant osteoprotegerin decreases tumor burden and increases survival in a murine model of multiple myeloma." Cancer Res. Jan. 15, 2003;63(2):287-9.

Wei S, et al., "Receptor activator of nuclear factor-kappa b ligand activates nuclear factor-kappa b in osteoclast precursors." Endocrinology. Mar. 2001;142(3):1290-5.

Wekerle T, et al., "Mechanisms of transplant tolerance induction using costimulatory blockade." Curr Opin Immunol. Oct. 2002;14(5):592-600.

Willard D, et al. "Expression , purification, and characterization of the human receptor activator of NF-kappaB ligand (RANKL) extracellular domain." Protein Expr Purif. Oct. 2000;20(1):48-57.

Wong BR, et al., "TRANCE is a novel ligand of the tumor necrosis factor receptor family that activates c-Jun N-terminal kinase in T cells." J Biol Chem. Oct. 3, 1997;272(40):25190-4.

Wuyts W, et al., "Evaluation of the role of RANK and OPG genes in Paget's disease of bone." Bone. Jan. 2001;28(1):104-7.

Yamagishi T, et al., "Reciprocal control of expression of mRNAs for osteoclast differentiation factor and OPG in osteogenic stromal cells by genistein: evidence for the involvement of topoisomerase II in osteoclastogenesis." Endocrinology. Aug. 2001;142(8):3632-7.

Yasuda H,et al. "Osteoclast differentiation factor is a ligand for osteoprotegerin/osteoclastogenesis-inhibitory factor and is identical to TRANCE/RANKL." Proc Natl Acad Sci U S A. Mar. 31, 1998;95(7):3597-602.

Lacey D. L. et al. "Osteoprotegerin ligand is a cytokine that regulates osteoclast differentiation and activation" *Cell* Cell Press, Cambridge, NA, US, vol. 93, Apr. 17, 1998, pp. 165-176.

Steed, P.M. et al. "Inactivation of TNF signaling by rationally designed dominant-negative TNF variants" *Science* (*American Assoc for the Advancement of Science*) vol. 301, No. 5641, (2003) pp. 1895-1898.

Yasuda H. et. al. "Osteoclast Differentiation factor is a ligand for osteoprotegerin/osteoclastogeneis—inhibitory factor and is identical to TRANCE/RANKL" *Proc. Of Natl. Acad of Sci.* , (1998) vol. 95, pp. 3597-3602.

* cited by examiner

SEQ ID No. 1:

Human RANKL
(aa 68)

FYFRAQMDPNRISEDGTHCIYRILRLHENADFQDTTLESQDTKLIPDSCRRIKQAFQGAVQKELQH
IVGSQHIRAEKAMVDGSWLDLAKRSKLEAQPFAHLTINATDIPSGSHKVSLSSWYHDRGWAKISNM
TFSNGKLIVNQDGFYYLYANICFRHHETSGDLATEYLQLMVYVTKTSIKIPSSHTLMKGGSTKYWS
GNSEFHFYSINVGGFFKLRSGEEISIEVSNPSLLDPDQDATYFGAFKVRDID

Human RANKL
(aa 317)

Figure 1a

SEQ ID No. 2:

HIS Tag | TEV Protease Cleavage Site | Human RANKL (aa 159)

MGHHHHHHSSGLEVLFQGPKLEAQPFAHLTINATDIPSGSHKVSLSSWYHDRGWAKISNMTF
SNGKLIVNQDGFYYLYANICFRHHETSGDLATEYLQLMVYVTKTSIKIPSSHTLMKGGSTKY
WSGNSEFHFYSINVGGFFKLRSGEEISIEVSNPSLLDPDQDATYFGAFKVRDID

Human RANKL
(aa 317)

Figure 1b

SEQ ID No. 3:

Mouse RANKL
(aa 68)

FLYFRAQMDPNRISEDSTHCFYRILRLHENADLQDSTLESEDTLPDSCRRMKQAFQGAVQKE
LQHIVGPQRFSGAPAMMEGSWLDVAQRGKPEAQPFAHLTINAASIPSGSHKVTLSSWYHDRG
WAKISNMTLSNGKLRVNQDGFYYLYANICFRHHETSGSVPTDYLQLMVYVVKTSIKIPSSHN
LMKGGSTKNWSGNSEFHFYSINVGGFFKLRAGEEISIQVSNPSLLDPDQDATYFGAFKVQDI
D (Mouse RANKL aa 316)

Figure 1c

```
Human: 159 KLEAQPFAHLTINATDIPSGSHKVSLSSWYHDRGWAKISNMTFSNGKLIVNQDGFYYLYA 218
           K EAQPFAHLTINA  IPSGSHKV+LSSWYHDRGWAKISNMT SNGKL VNQDGFYYLYA
Mouse: 158 KPEAQPFAHLTINAASIPSGSHKVTLSSWYHDRGWAKISNMTLSNGKLRVNQDGFYYLYA 217

Human: 219 NICFRHHETSGDLATEYLQLMVYVTKTSIKIPSSHTLMKGGSTKYWSGNSEFHFYSINVG 278
           NICFRHHETSG + T+YLQLMVYV KTSIKIPSSH LMKGGSTK WSGNSEFHFYSINVG
Mouse: 218 NICFRHHETSGSVPTDYLQLMVYVVKTSIKIPSSHNLMKGGSTKNWSGNSEFHFYSINVG 277

Human: 279 GFFKLRSGEEISIEVSNPSLLDPDQDATYFGAFKVRDID 317
           GFFKLR+GEEISI+VSNPSLLDPDQDATYFGAFKV+DID
Mouse: 278 GFFKLRAGEEISIQVSNPSLLDPDQDATYFGAFKVQDID 316
```

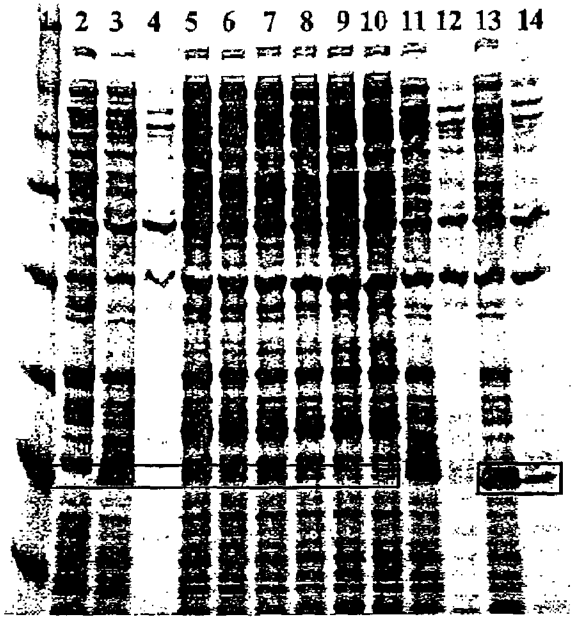

25C, 0.5 mM IPTG, 4 hr induction

Coomassie Stained Gel

| Lane | Description | Strain |
|---|---|---|
| 1 | SeeBlue Plus2 MW Standards | NA |
| 2 | Pre Induced Total Protein | His-OPGL |
| 3 | Post Induced Total Protein | His-OPGL |
| 4 | Post Induced Soluble Protein | His-OPGL |
| 5 | Post Induced Total Protein | T173R/C221S |
| 6 | Post Induced Soluble Protein | T173R/C221S |
| 7 | Post Induced Total Protein | S183R/C221S |
| 8 | Post Induced Soluble Protein | S183R/C221S |
| 9 | Post Induced Total Protein | A232K/C221S |
| 10 | Post Induced Soluble Protein | A232K/C221S |
| 11 | Post Induced Total Protein | I207K/C221S |
| 12 | Post Induced Soluble Protein | I207K/C221S |
| 13 | Post Induced Total Protein | I247E/C221S |
| 14 | Post Induced Soluble Protein | I247E/C221S |

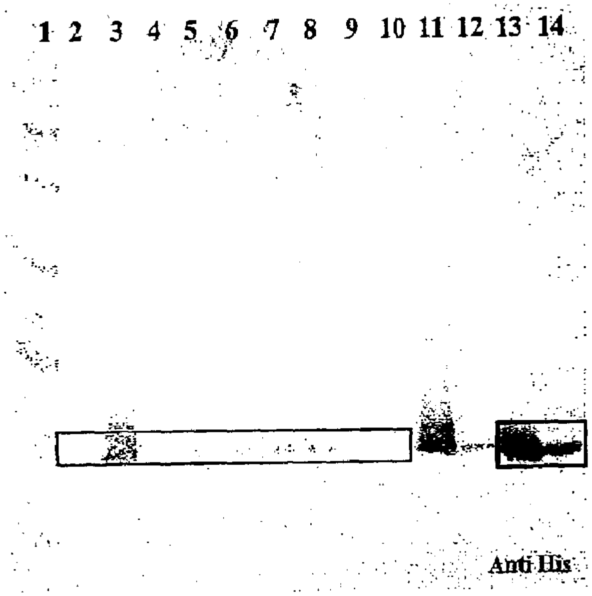

Western blot probed with anti-HIS

Figure 6

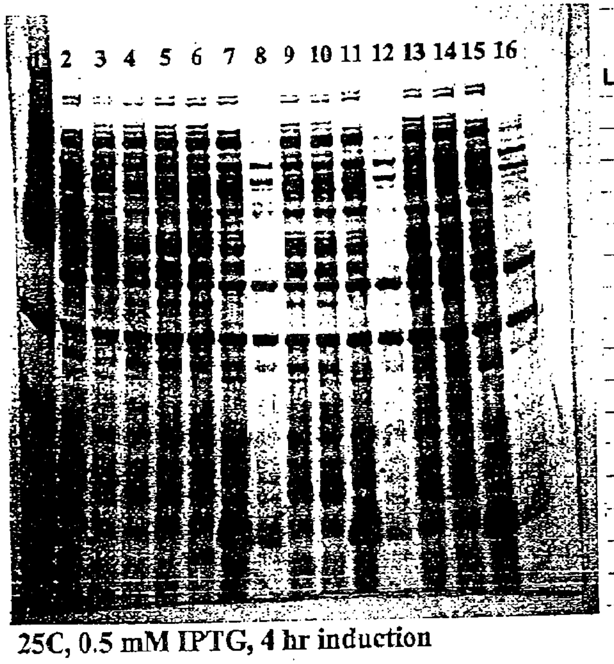

25C, 0.5 mM IPTG, 4 hr induction

Coomassie Stained Gel

| Lane | Description | Variant |
|---|---|---|
| 1 | SeeBlue Plus2 MW Standards | NA |
| 2 | Pre Induced Total Protein | C221S |
| 3 | Post Induced Total Protein | C221S |
| 4 | Post Induced Soluble Protein | C221S |
| 5 | Post Induced Total Protein | I247E |
| 6 | Post Induced Soluble Protein | I247E |
| 7 | Post Induced Total Protein | I247E/C221S |
| 8 | Post Induced Soluble Protein | I247E/C221S |
| 9 | Post Induced Total Protein | I247K |
| 10 | Post Induced Soluble Protein | I247K |
| 11 | Post Induced Total Protein | I247K/C221S |
| 12 | Post Induced Soluble Protein | I247K/C221S |
| 13 | Post Induced Total Protein | I127Q |
| 14 | Post Induced Soluble Protein | I127Q |
| 15 | Post Induced Total Protein | I247Q/C221S |
| 16 | Post Induced Soluble Protein | I247Q/C221S |

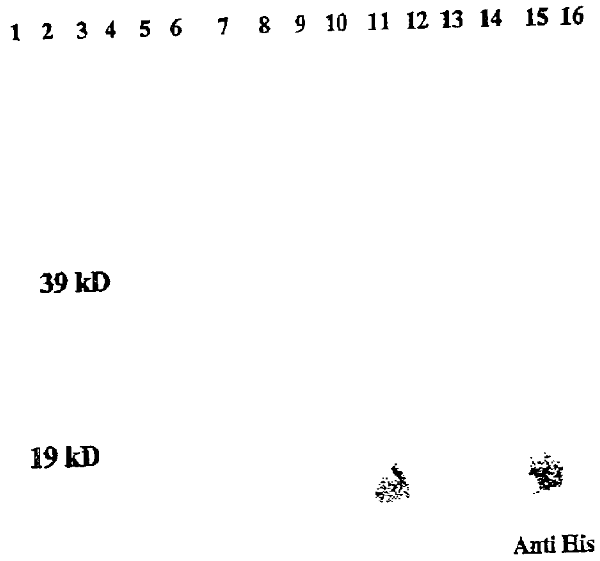

Western blot probed with anti-HIS

Figure 8

I247E/C221S
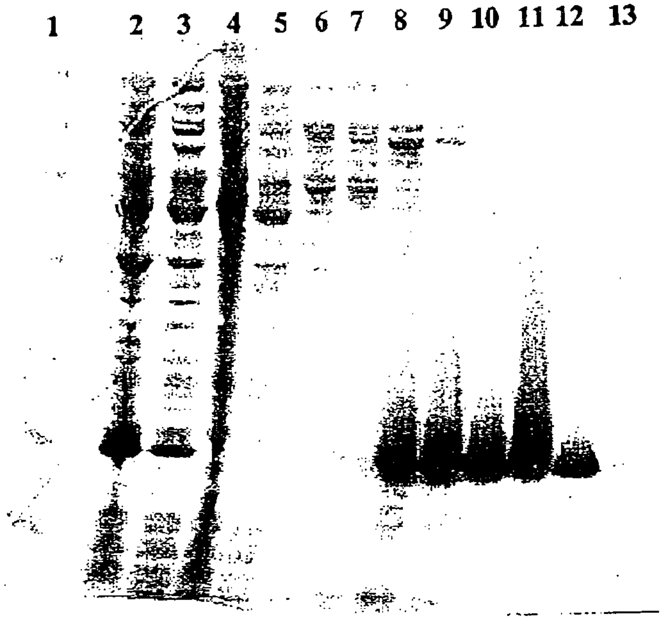
25C, 0.5 mM IPTG, 4 hr induction
Coomassie Stained Gel
| Lane | Description |
|---|---|
| 1 | SeeBlue Plus2 MW Standards |
| 2 | Total Protein |
| 3 | Soluble Protein |
| 4 | Flow Thru |
| 5 | Wash |
| 6 | 35 mM Imidazole Wash |
| 7 | 150 mM Imidazole Wash 1 |
| 8 | 150 mM Imidazole Wash 2 |
| 9 | 150 mM Imidazole Wash 3 |
| 10 | 500 mM Imidazole Elution 1 |
| 11 | 500 mM Imidazole Elution 2 |
| 12 | 500 mM Imidazole Elution 3 |
| 13 | 500 mM Imidazole Elution 4 |
51 kD
39 kD
19 kD
I247D/C221S
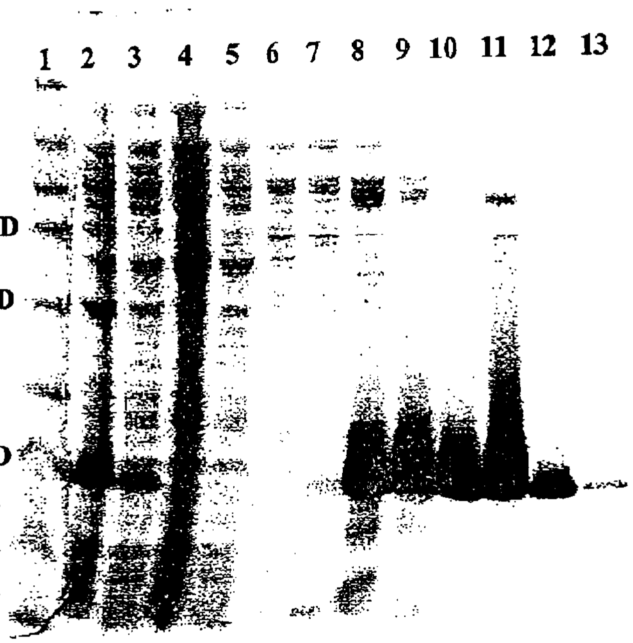
Coomassie Stained Gel
Figure 9

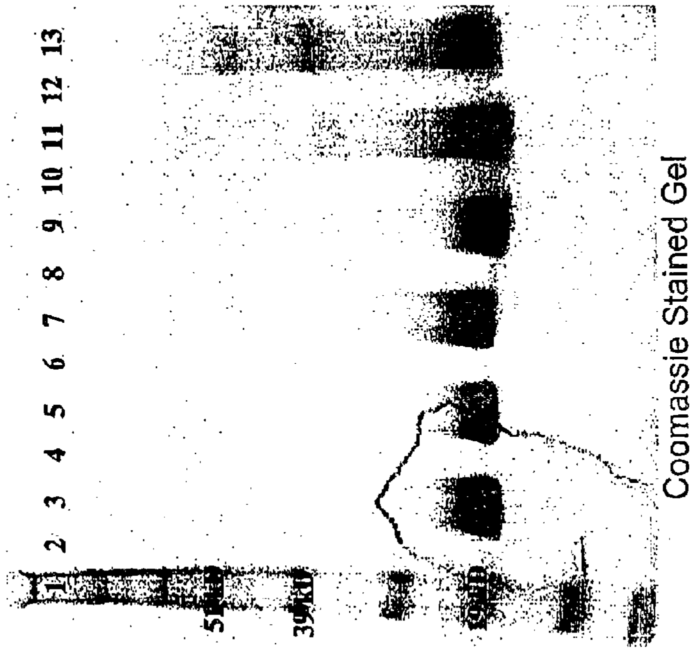
Coomassie Stained Gel
| Lane | Description |
|---|---|
| 1 | SeeBlue Plus2 MW Standards |
| 2 | none |
| 3 | 5 ug I247E/C221S |
| 4 | none |
| 5 | 5 ug I247D/C221S |
| 6 | none |
| 7 | 5 ug I247K/C221S |
| 8 | none |
| 9 | 5 ug I247Q/C221S |
| 10 | none |
| 11 | 5 ug I247A/C221S |
| 12 | none |
| 13 | 5 ug I207K/C221S |
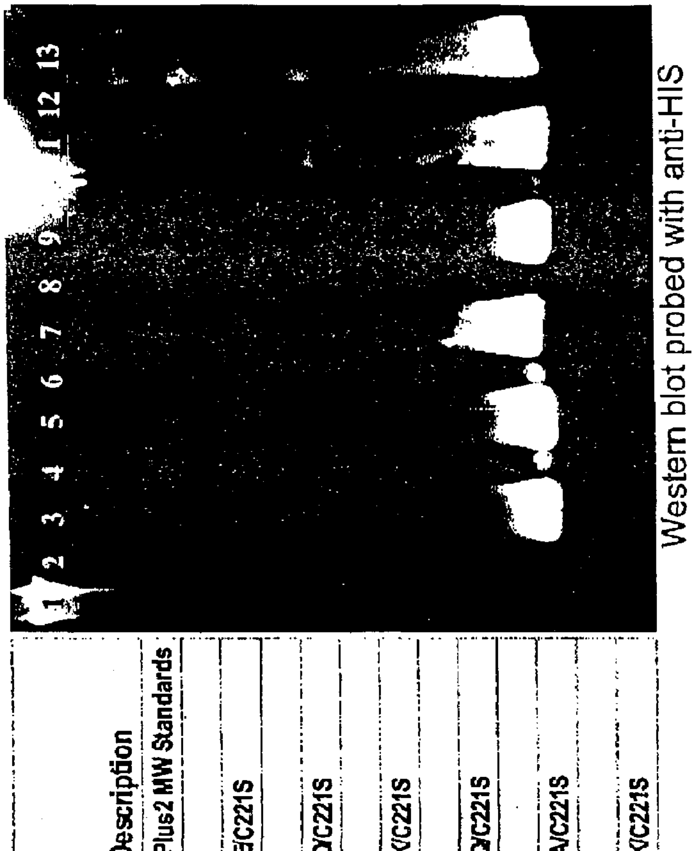
Western blot probed with anti-HIS
Figure 10

| Variant | Mw (Kd) | % Trimer | % Oligomer | Expression |
|---|---|---|---|---|
| C221S/I247E | 65 | 97 | 3 | 1.4 mg/g |
| C221S/I207K | 68 | 90 | 10 | 1.2 mg/g |
| C221S/I247K | 71 | 84 | 16 | 1.2 mg/g |
| C221S/I247Q | 69 | 91 | 9 | 1.1 mg/g |
| C221S/I247A | 67 | 92 | 8 | 1.4 mg/g |
| C221S/1247D | 68 | 92 | 8 | 1.3 mg/g |

Figure 12

| Lane | Description |
|---|---|
| 1 | C221S/I247E, no RANK-Fc IP |
| 2 | no ligand, 1 ug RANK-Fc IP |
| 3 | 200 ng C221S/I247E, 1 ug RANK-Fc IP |
| 4 | 200 ng C221S/I247D, 1 ug RANK-Fc IP |
| 5 | 200 ng C221S/I247K, 1 ug RANK-Fc IP |
| 6 | 200 ng C221S/I247Q, 1 ug RANK-Fc IP |
| 7 | 200 ng C221S/I247A, 1 ug RANK-Fc IP |
| 8 | 200 ng C221S/I207K, 1 ug RANK-Fc IP |
| 9 | 200 ng R&D RANKL, 1 ug RANK-Fc IP |
| 10 | none |
| 11 | 0.5 ug C221S/I247E |
| 12 | 0.5 ug R&D RANKL |

Anti-RANKL Western

| Lane | Description |
|---|---|
| 1 | no receptor, 200 ng C221S/I247E |
| 2 | 1ug OPG/Fc, no ligand |
| 3 | 1ug OPG/Fc, 200 ng C221S/I247E |
| 4 | 1ug OPG/Fc, 200 ng C221S/I247D |
| 5 | 1ug OPG/Fc, 200 ng C221S/I247K |
| 6 | 1ug OPG/Fc, 200 ng C221S/I247Q |
| 7 | 1ug OPG/Fc, 200 ng C221S/I247A |
| 8 | 1ug OPG/Fc, 200 ng C221S/I207K |
| 9 | 1ug OPG/Fc, 100 ng R&D RANKL |
| 10 | 500 ng C221S/I247E |

| | | | |
|---|---|---|---|
| A172R | R191Q | K248E | I249R-S228E |
| A172Q | G191A | I249Q | K248E-T227K |
| S179E | R223Q | I249R | K248E-T227Q |
| S179D | R223E | H253T | R191K-I249R |
| H180E | R223M | H253S | R191E-I249R |
| H180N | H225R | S268D | G192A-K248E |
| H180S | H225N | E269R | D190Q-K248E |
| K181Q | H225T | E269Q | D190T-K248E |
| K181E | H225E | E269T | H225R-I249R |
| K181R | E226Q | E269K | H225N-I249R |
| S183K | E226R | F270V | E226Q-I249R |
| S183E | E226D | F270E | E226R-I249R |
| Y188F | T227K | F270T | H225R-G192A |
| Y188M | T227Q | F270K | H225N-G192A |
| Y188Q | S228H | R284E | H225R-D190Q |
| Y188E | S228E | S297Q | H225R-D190T |
| H189E | S228D | S297E | G192A-H225R-I249R |
| H189A | T233R | S297D | G192A-H225N-I249R |
| H189R | T233D | D300N | R191K-E226Q-K248E |
| D190Q | T233E | D302E | R191K-E226R-K248E |
| D190T | Q237K | D302Q | |
| R191K | Q237E | D302H | |
| R191E | Q237T | I249R-S228H | |

Figure 22

| | RANKL VARIANT | | |
|---|---|---|---|
| Super Agonist | c221s/i247e | a172r | 1 |
| Agonist | c221s/i247e | a172q | 18 |
| | c221s/i247e | y188e | |
| | c221s/i247e | y188f | |
| | c221s/i247e | y188m | |
| | c221s/i247e | t233d | |
| | c221s/i247e | t233e | |
| | c221s/i247e | s228d | |
| | c221s/i247e | i249q | |
| | c221s/i247e | i249r | |
| | c221s/i247e | i249r/s228h | |
| | c221s/i247e | h253t | |
| | c221s/i247e | d302q | |
| | c221s/i247e | s268d | |
| | c221s/i247e | r191k | |
| | c221s/i247e | s183k | |
| | c221s/i247e | h189r | |
| | c221s/i247e | y188q | |
| | c221s/i247e | h198e | |
| Weak Agonist | c221s/i247e | k181q | 12 |
| | c221s/i247e | q237k | |
| | c221s/i247e | k248e | |
| | c221s/i247e | r284e | |
| | c221s/i247e | i249r/s228e | |
| | c221s/i247e | d300n | |
| | c221s/i247e | d190t/k248e | |
| | c221s/i247e | r191q | |
| | c221s/i247e | t227k | |
| | c221s/i247e | d190q/k248e | |
| | c221s/i247e | e226r/i249r | |
| | c221s/i247e | r191e/i249r | |

| | RANKL VARIANT | | |
|---|---|---|---|
| Intermediate Non-Agonists | c221s/i247e | h225e | 16 |
| | c221s/i247e | h225n | |
| | c221s/i247e | h225t | |
| | c221s/i247e | r223q | |
| | c221s/i247e | e226d | |
| | c221s/i247e | e226q | |
| | c221s/i247e | e226r | |
| | c221s/i247e | e269q | |
| | c221s/i247e | e269t | |
| | c221s/i247e | q237e | |
| | c221s/i247e | k248e/t227q | |
| | c221s/i247e | k181q | |
| | c221s/i247e | h225r/d190q | |
| | c221s/i247e | h225r/g192a | |
| | c221s/i247e | h225r | |
| | c221s/i247e | h225n/g192a | |
| Non-Agonists | c221s/i247e | e269k | 5 |
| | c221s/i247e | f270t | |
| | c221s/i247e | h225n/i249r | |
| | c221s/i247e | h225r/i249r | |
| | c221s/i247e | g192a/k298e | |

VARIANTS OF RANKL PROTEIN

This application claims the benefit of the filing date of U.S. Ser. No. 60/345,805, filed Jan. 4, 2002 and U.S. Ser. No. 60/373,453, filed Apr. 17, 2002, all of which are expressly incorporated by reference in their entirety.

The present application is related to a co-pending application filed on even date and entitled "DOMINANT NEGATIVE PROTEINS AND METHODS THEREOF, hereby incorporated by reference in its entirety."

FIELD OF THE INVENTION

The present invention relates to novel variants of the extracellular domains (ECD) of human RANKL (Receptor Activator of Nuclear Factor—κB Ligand) proteins and fragments, derivatives, conformers, and analogs thereof. These novel variants comprise RANKL variants that express solubly in *E. coli,* RANKL variants that antagonize wild type RANKL, and RANKL variants that act as superagonists.

BACKGROUND OF THE INVENTION

Normal bone remodeling is a process in which new bone deposition by osteoblasts is balanced through bone resorption by osteoclasts (see Gowen, M., Every, J G, and Kumar S. Emerging therapies for osteoporosis. Emerging Drugs, 2000 5(1): p.1-43.) In several disease states, the balance between bone deposition and bone resorption is perturbed. In osteoporosis, for example, excess bone resorption leads to brittle bones and frequent fractures of the wrist, vertebrae, and hip. In rheumatoid arthritis, increased bone resorption leads to malformations of the bones within arthritic joints. Re-establishing normal bone remodeling in these and other disorders can be achieved by decreasing or increasing the number and activity of osteoclasts (See Rodan, G A, and Martin T J. Therapeutic approaches to bone disease. Science 2000 289: p. 1508-1514.)

Several proteins modulate the bone remodeling orchestrated by osteoblasts and osteoclasts. Three key proteins are the cell-surface receptor RANK (Receptor Activator of NF-κB), the soluble decoy receptor OPG (osteoprotegerin), and the soluble and transmembrane forms of RANKL (RANK ligand, also known as RANKL11, TNF-related activation induced cytokine (TRANCE), osteoclast differentiation factor (ODF), and osteoprotegerin ligand (OPGL)). RANK is activated by the binding of its ligand, RANKL, which leads to the differentiation, survival, and fusion of pre-osteoclasts to form active bone resorbing osteoclasts (see Lacey D L, Timms E, Tan H-L, Kelley M J, Dunstan C R, Burgess T et al. Osteoprotegerin Ligand is a cytokine that regulates osteoclast differentiation and activation. 1998 Cell 93: p. 165-176.). RANKL is a trimeric TNF family member that binds to the trimeric RANK receptor.

The RANKL/OPG/RANK biochemical axis has been successfully targeted to treat osteoporosis, rheumatoid arthritis, cancer-induced bone destruction, metastasis, hypercalcemia, and pain (see Hofbauer, L C, Neubauer, A, and Heufelder A E. Receptor activator of nuclear factor-κB ligand and osteoprotegrin. 2001 Cancer 92(3): p.460-470; Takahashi N, Udagawa N, and Suda T.) Therapies utilizing OPG (see Honore P, Luger N M, Samino M A C, Schwei M J et al. Osteoprotegerin blocks bone cancer-induced skeletal destruction, skeletal pain and pain-related neurochemical reorganization of the spinal cord. 2000 Nature Medicine 6(5):521-528.) or the soluble RANK-Fc protein (See Oyajobi B O, Anderson D M, Traianedes K, Williams P J, Yoneda T, Mundy G R. Therapeutic efficacy of a soluble receptor activator of nuclear factor kappaB-IgG Fc fusion protein in suppressing bone resorption and hypercalcemia in a model of humoral hypercalcemia of malignancy. 2001 Cancer Res 61(6): p. 2572-8) are also in development. OPG and soluble RANK-Fc protein constructs bind to RANKL, thereby decreasing amount of RANKL that is available for RANK receptor activation.

Hypercalcemia is a late stage complication of cancer, disrupting the body's ability to maintain normal levels of calcium, resulting in calcium deposit in the kidneys, heart conditions and neural dysfunction and occurs most frequently in patients cancers of the with lung and breast. Hypercalcemia also occurs in patients with multiple myeloma, cancers of the head and neck, sarcoma, cancers of unknown primary origin, lymphoma, leukemia, melanoma, renal cancer, and gastrointestinal cancers (e.g. esophageal, stomach, intestinal, colon and rectal cancers).

In addition to being important in bone biology, RANKL plays a role in the immune system by regulating antigen-specific T cell responses (See Anderson et al., A homologue of the TNF receptor and its ligand enhance T-cell growth and dendritic-cell function; Nature 1997, 390(6656):175-9). RANKL is highly expressed on activated T cells while the RANK receptor is expressed at high levels on mature dendritic cells (DC). The interaction between RANKL and RANK acts as a costimulatory signal, which enhances DC survival and T cell proliferation by inducing DC differentiation, cytokine production and reduced apoptosis in both cell types. Immunotherapy to produce tolerance to transplanted tissues and/or organs can be achieved by blocking the costimulatory signal using RANK antagonists. Blocking costimulation prevents T cell activation by DCs, and causes alloreactive T cells to become anergic and/or undergo apoptosis (See Adler et al., Immunotherapy as a means to induce transplantation tolerance; Current Opinion in Immunology 2002, 14:660-665). By a similar mechanism of action, antagonizing RANK signaling could be a treatment for autoimmune disorders such as systemic lupus erythematosus, inflammatory bowel disease, diabetes, multiple sclerosis, rheumatoid arthritis, and ankylosing spondylitis. RANKL variant superagonists, on the other hand could be used to activate the immune system by promoting T cell activation. RANKL superagonists could be useful treatments for diseases including but not limited to cancer and viral infection.

Much work has been done to develop therapeutic entities and reagents for biological research based on RANKL. For example, RANKL fragments, analogs, derivatives, or conformers having the ability to bind OPG, which could be used as treatments for a variety of bone diseases, have been described (See U.S. Pat. No. 5,843,678). RANKL variants, which induce production of an immune response that down-regulates RANKL activity, have been disclosed (See WO 00/15807). In other studies, utilization of RANKL protein and its derivatives as immune modulators has been proposed (See WO 99/29865). All references cited herein are hereby expressly incorporated by reference.

Accordingly, a need exists for RANKL antagonists and superagonists.

SUMMARY OF THE INVENTION

The present invention is directed at generating novel variants of human RANKL protein, comprising the extracellular domains of RANKL, which behave as RANKL antagonists or superagonists. Here, we describe novel variants of human RANKL protein that behave as RANKL antagonists and superagonists. RANKL antagonists may comprise dominant-negative RANKL proteins and/or competitive inhibitors of RANKL. A further component of the invention is the identification of modifications that confer soluble expression in *E. coli*. Soluble expression allows for efficient and cost-effective production and manufacturing of human RANKL variants, and therefore is critical for the discovery, characterization, and production of novel RANKL antagonists and superagonists.

An aspect of the present invention is non-naturally occurring RANKL variants that express solubly in bacteria, including but not limited to *E. coli*. In previous studies, it has been observed that human RANKL forms inclusion bodies when expressed in *E. coli*. Alternate production routes such as refolding from inclusion bodies or mammalian expression are significantly more expensive and time consuming than soluble bacterial expression. Soluble bacterial expression facilitates the discovery, characterization, and production of novel RANKL variants. It is a further object of the invention to provide a method that can be used to engineer variants of other proteins that express solubly in bacteria, including but not limited to *E. coli*.

The invention further relates to the design of human RANKL antagonists that inhibit the interaction between RANK receptor and RANKL and methods for generating the same.

An aspect of the present invention is non-naturally occurring RANKL variants that: 1) do not appreciably agonize RANK activity; 2) antagonize RANK activity; 3) exchange with wild-type RANKL (that is, form trimers containing at least one wild type RANKL protein monomer and at least one variant RANKL protein monomer), and 4) interfere with RANK mediated osteoclast formation and/or T cell costimulation. Such variants are referred to as "dominant negative" variants.

A further object of the present invention is RANKL variants that preferentially heterotrimerize with wild-type RANKL.

An aspect of the present invention is RANKL variants that: 1) do not appreciably agonize RANK activity; 2) antagonize RANK activity; 3) compete with wild type RANKL for binding the RANK receptor, and 4) interfere with RANK mediated osteoclast formation and activation and/or T cell costimulation. Such variants are referred to as "competitive inhibitor" variants.

The invention further relates to the design of human RANKL superagonists that bind and activate the RANK receptor more strongly than the wild type human RANKL protein does.

In a further aspect, the invention provides recombinant nucleic acids encoding the variant RANKL proteins, expression vectors, and host cells.

In an additional aspect, the invention provides methods of producing a variant RANKL protein comprising culturing the host cells of the invention under conditions suitable for expression of the variant RANKL protein.

In a further aspect, the invention provides pharmaceutical compositions comprising a variant RANKL protein of the invention and a pharmaceutical carrier.

In a further aspect, the invention provides methods for treating RANKL-related disorders comprising administering a variant RANKL protein of the invention to a patient.

In accordance with the objects outlined above, the present invention provides RANKL variant proteins comprising amino acid sequences with at least one amino acid change compared to the wild type RANKL proteins.

BRIEF DESCRIPTION OF THE DRAWINGS

FIG. 1*a* shows the amino acid sequence of wild-type human RANKL extracellular region (amino acids 68-317 of GenBank accession AAB86811; SEQ ID NO: 1).

FIG. 1*b* shows the amino acid sequence of wild-type human RANKL extracellular region with 6X histidine tag and TEV protease cleavage site. This construct and variants thereof were expressed and assayed biochemically and functionally in cell-based assays (SEQ ID NO: 2)

FIG. 1*c* shows the amino acid sequence of wild-type mouse RANKL extracellular region (amino acids 68-316 of GenBank accession NP_035743; SEQ ID NO: 3). This sequence serves as reference for numbering mouse RANKL amino acid positions.

FIG. 2*a* shows a BLAST alignment between amino acids 159-317 (92-250 of SEQ ID NO: 1) of full-length wild-type human RANKL and amino acids 158-316 (91-249 of SEQ ID NO: 3) of full-length wild-type mouse RANKL.

FIG. 2*b* shows a listing of mutations of several human RANKL solubility variants.

FIG. 6 shows expression analysis that demonstrates soluble *E. coli* expression of RANKL variants C221S/I207K and C221S/I247E. Wild-type RANKL is not soluble along with several other variants.

FIG. 8 shows that the C221S mutation when combined with the I247E, I247K, or I247Q mutations confer soluble expression in *E. coli*. Each of the single mutations in isolation is not sufficient to confer soluble expression.

FIG. 9 shows Ni NTA batch purification from soluble fraction of the two RANKL variants C221S/I247E and C221S/I247D. For each purification, fractions from lanes 11-13 were pooled and equilibriated in PBS, pH 8.0. Analysis shows that soluble variants can be expressed to high levels and purified.

FIG. 10 shows a quality control gel of highly purified soluble RANKL protein preparations from the six variants C221S/I247E, C221S/I247D, C221S/I247K, C221S/I247Q, C221S/I247A, and C221S/I207K.

FIG. 12 Summary of light scatter-size exclusion chromatography showing that all six human RANKL variants are predominantly timeric. Expression levels are expressed as mass of RANK protein purified per mass of bacteria producing the protein.

FIG. 22 shows the list of computationally designed inhibitory RANKL variants. These inhibitory variants can be combined with RANKL solubility variants to produce soluble human RANKL variants.

Figure 3:
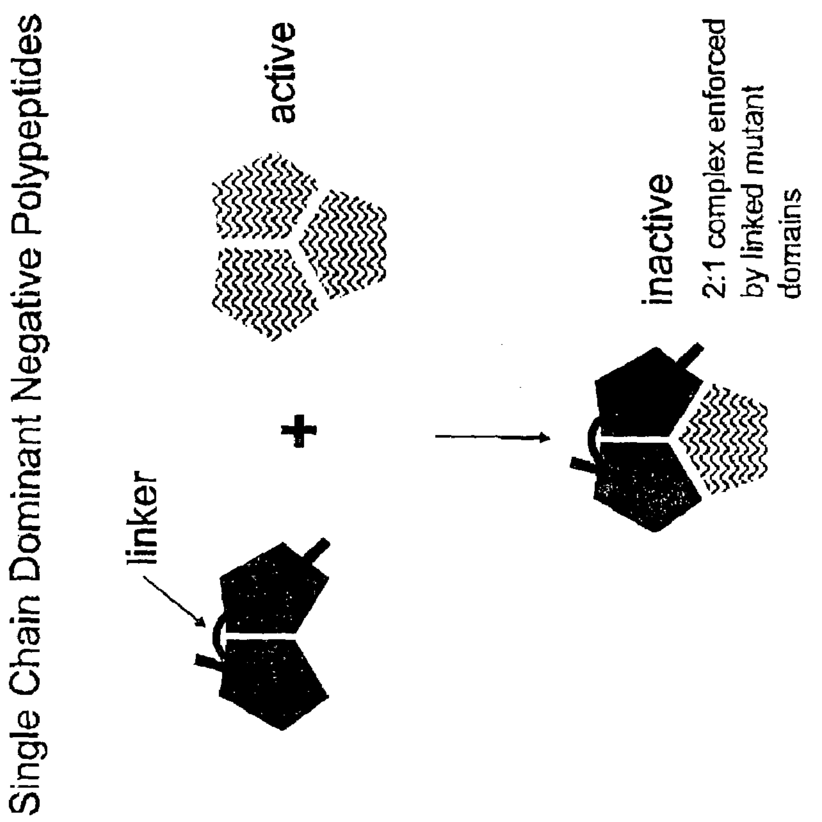
FIG. 3 shows the strategy for generating single chain dominant-negative RANKL variants. The linked dimer forms an inactive complex with wild-type RANKL. Through this mechanism of inactivating wild-type RANKL, the single chain dominant-negative RANKL variants will exert their therapeutic effects.
Figure 4:
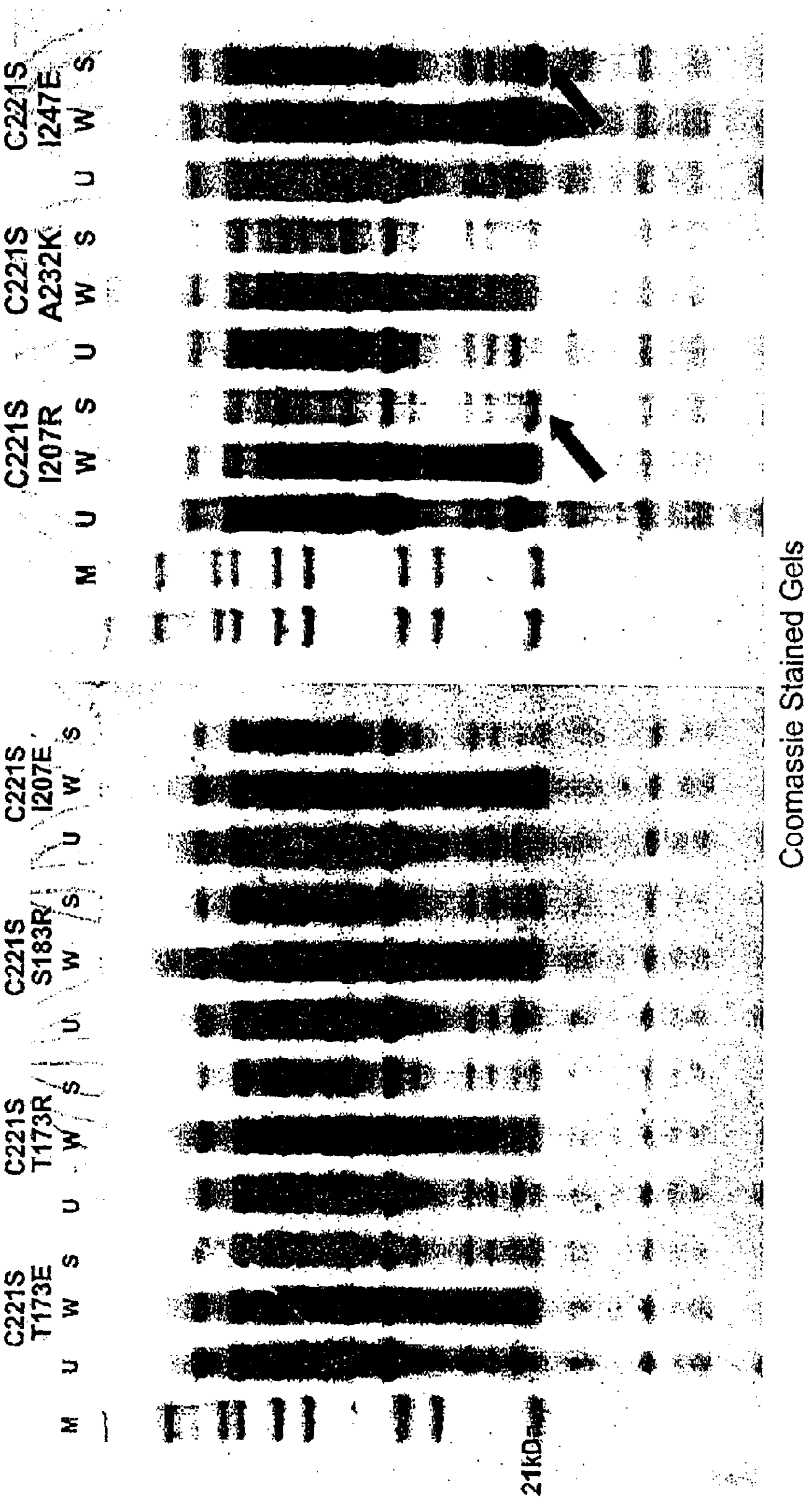
FIG. 4 shows expression analysis that demonstrates soluble *E. coli* expression of C221S/I207R and C221S/I247E (arrows). RANKL variants C221S/173E, C221S/173R, C221S/S183R, C221S/A232K and C221S/I207E do not exhibit soluble expression. Wild-type RANKL was also insoluble (data not shown). M is molecular weight marker; U is uninduced bacterial lysate, W is whole cell bacterial lysate, and S is soluble fraction
Figure 5:
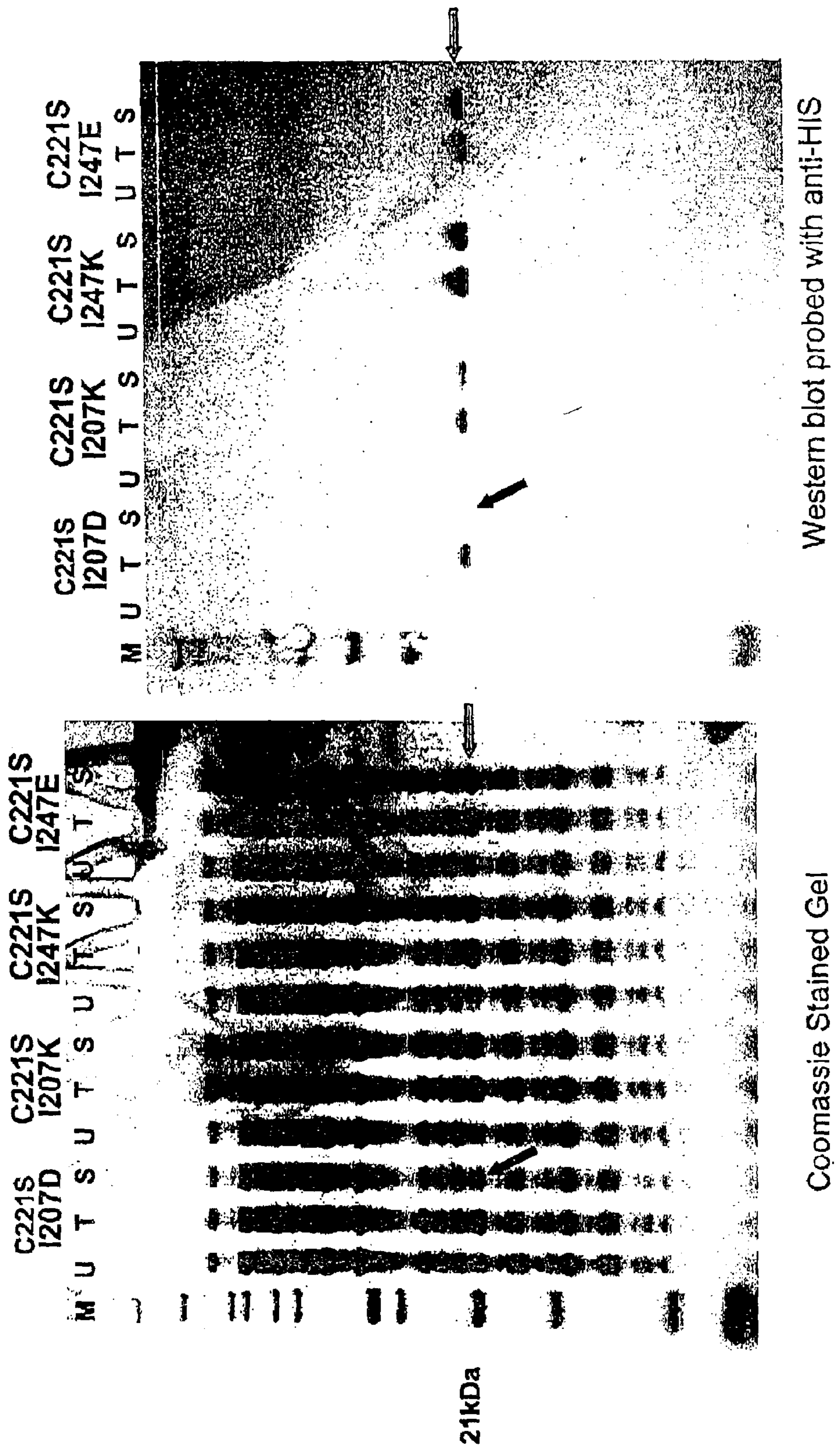
FIG. 5 shows expression analysis that demonstrates soluble *E. coli* expression of the additional RANKL variants C221S/I207K, C221S/I247K, and C221S/I247E and demonstrates lack of soluble *E. coli* expression of the variant C221S/I207D. M is molecular weight marker; U is uninduced bacterial lysate, T is whole cell bacterial lysate, and S is soluble fraction.

FIG. 29 Summary of RANKL agonism screens. Twenty-one RANKL variants were identified to be non-agonists while 12 were weak agonists. One RANKL variant, C221S/I247E/A172R is a superagonist.

FIG. 30 Summary of RANKL antagonizing variants. These variants were shown to antagonize RANKL mediated osteoclastogenesis.Definitions By "RANK" herein is meant a cell-surface receptor activator of NF-κB. The RANK protein (or nucleic acid) can be from proteins may be from any number of organisms, with RANK proteins from mammals being particularly preferred. Suitable mammals include, but are not limited to, rodents (rats, mice, hamsters, guinea pigs, etc.), primates, farm animals (including sheep, goats, pigs, cows, horses, etc); and in the most preferred embodiment, from humans (the sequence of which is depicted in the figures). As will be appreciated by those in the art, RANK proteins based on RANK proteins from mammals other than humans may find use in animal models of human disease.

By "RANKL" herein is meant a ligand for RANK. Again, RANKL sequences from humans are preferred (sequences depicted in the Figures), but RANKL sequences from organisms outlined above are also included. As is more fully outlined below, RANKL proteins trimerize (although higher oligomers may also occur) to activate the RANK receptor. Thus, RANKL proteins occur as monomers as well as oligomers, generally trimers. As more fully outlined below, variant RANKL protein monomers can be made which physically interact with other monomers (including other variant RANKL monomers, wild-type monomers, or wild-type monomers from different species) to form mixed oligomers or trimers.

By "variant RANKL monomer proteins" or grammatical equivalents herein is meant a RANKL monomer protein that contains at least one modification, including substitutions, insertions and deletions. Thus, variant RANKL proteins means non-naturally occurring RANKL proteins that differ from the wild type RANKL protein by at least 1 modification, including but not limited to amino acid substitution, insertion, or deletion. RANKL variants are characterized by the predetermined nature of the variation, a feature that sets them apart from naturally occurring allelic or interspecies variation of the RANKL protein sequence. The RANKL variants typically either exhibit the same qualitative biological activity as the naturally occurring RANKL or have been specifically engineered to have alternate biological properties. Variant RANKL proteins are derived from the extracellular domain of wild type RANKL (that is, residues 68-317 in FIG. 1*a*). However, the variant RANKL proteins may contain insertions or deletions at the N-terminus, C-terminus, or internally. For example, a preferred truncated variant of the human RANKL protein comprises residues 159-317, as shown in FIG. 1*b*. Thus, in a preferred embodiment, variant RANKL proteins have at least 1 residue that differs from the human RANKL sequence, with at least 2, 3, 4, or 5 different residues being more preferred. Variant RANKL proteins may comprise one domain or multiple domains connected by linker sequences. Variant RANKL proteins may contain further modifications, for instance modifications that alter stability or immunogenicity or which enable posttranslational modifications such as PEGylation or glycosylation.

In general, deletions include portions of RANKL that are not extracellular, and include substitutions in residues corresponding to monomer association sites and receptor recognition and/or binding sites. Preferred variants are further described below, and include both conservative and non-conservative substitutions, with the latter being preferred.

By "extracellular domain" or "ECD" as used herein is meant the segment of protein existing predominantly outside the cell. For transmembrane proteins, this segment can be tethered to the cell through a transmembrane domain or released from the cell through proteolytic digestion. Alternatively, the extracellular domain could comprise the whole protein or amino acid segments thereof when secreted from the cell. In general, RANKL members are expressed as type II transmembrane proteins (extracellular C terminus). Soluble forms of RANKL proteins may result from proteolytic cleavage of the signal propeptide by matrix metalloproteinases termed TNF-alpha converting enzymes (TACE) or directly by recombinant methods. Unless otherwise disclosed, the variant RANKL proteins of the present invention are composed of the extracellular domain or functional equivalents thereof. That is, the variants of the present invention do not comprise transmembrane domains unless specifically noted.

By "agonists of wild-type RANKL" or grammatical equivalents thereof, herein is meant variants of RANKL which themselves or in combination with wild type RANKL appreciably activate RANK receptor. In a preferred embodiment, activation of the RANK receptor by agonistic RANKL variants is between 50% and 110% of the activation that would be attained with an equal amount of wild type RANKL protein, with between 80% and 100% being especially preferred.

By "superagonists of wild-type RANKL" or grammatical equivalents thereof, herein is meant variants of RANKL that enhance the activation of RANK receptor signaling by wild type RANKL proteins or that themselves activate the RANKL receptor more strongly than an equal amount of wild type RANKL. In a preferred embodiment the RANKL superagonist proteins yield at least 10% more activity than wild type RANKL, with at least 50%, 100% or 200% increases in activity being especially preferred.

By "altered property" or grammatical equivalents thereof herein is meant, in the context of a protein, any characteristic or attribute of a protein that differs from the corresponding property of a naturally occurring protein. These properties include, but are not limited to cytotoxic activity; oxidative stability, substrate specificity, substrate binding or catalytic activity, thermal stability, alkaline stability, pH activity profile, resistance to proteolytic degradation, kinetic association (Kon) and dissociation (Koff) rate, protein folding, immunogenicity, osteoclastogenesis, binding affinity and selectivity, ability to be secreted, ability to be displayed on the surface of a cell, ability to oligomerize, ability to signal, ability to stimulate cell proliferation, ability to activate receptors; ability to induce differentiation, survival and fusion of pre-osteoclasts, ability to inhibit cell proliferation, ability to induce apoptosis, ability to be modified by phosphorylation or glycosylation, and the ability to treat disease. Unless otherwise specified, a property of a RANKL variant is considered to be "altered" when the property exhibits preferably at least a 5%, more preferably 50%, and most preferably at least a 2-fold increase or decrease relative to the corresponding property in the wild type RANKL protein. For example, a change in osteoclast activity is evidenced by at least a 75% or greater decrease in osteoclastogenesis initiated by a variant RANKL protein as compared to wild-type protein, and a change in binding affinity is evidenced by at least a 5% or greater increase or decrease in binding affinity to wild-type RANK and/or OPG receptors.

By "antagonists of wild type RANKL" or grammatical equivalents thereof herein is meant variants of RANKL that inhibit or significantly decrease the activation of RANK receptor signaling by wild-type RANKL proteins. Both dominant negative RANKL variants and competitive inhibitors of RANKL are antagonists of wild type RANKL. Furthermore, antagonists of wild type RANKL should not be able to appreciably activate the RANK receptor and initiate the RANKL signaling pathway(s). In a preferred embodiment, at least a 50% decrease in receptor activation relative to wild type RANKL is seen, with greater than 50%, 76%, 80-90% being preferred.

By "competitive inhibitor RANKL variants" or "ciRANKL" or grammatical equivalents thereof herein is meant variants that compete with naturally occurring RANKL protein for binding to the RANK receptor, thereby limiting the ability of naturally occurring RANKL to bind and activate the RANK receptor. In general, ci RANKL proteins are included within the definition of variant RANKL proteins.

By "conformer" herein is meant a protein that has a protein backbone three-dimensional structure that is virtually the same as a reference protein but that has significant differences in the amino acid sequence.

By "control sequences" herein is meant nucleic acid sequences necessary for the expression of an operably linked coding sequence in a particular host organism. Control sequences include, but are not limited to, promoters, enhancers, and ribosome-binding site By "epitope" herein is meant a portion of a protein that mediates an immune response. An epitope may serve as a binding site for an antibody, T-cell receptor, and/or MHC molecule.

By "exposed residues" as used herein is meant those residues whose side chains are significantly exposed to solvent. In a preferred embodiment, at least 30 $Å^2$ of solvent exposed area is present, with greater than 50 $Å^2$ or 75 $Å^2$ being especially preferred. In an alternate embodiment, at least 50% of the surface area of the side chain is exposed to solvent, with greater than 75% or 90% being preferred.

By "gene therapy" herein is meant the one time or repeated administration of a therapeutically effective DNA, mRNA, or other nucleic acid. In one embodiment, genes are introduced into cells in order to achieve in vivo synthesis of a therapeutically effective genetic product, for example for replacement of a defective gene. Antisense RNA and DNA can be used as therapeutic agents for blocking the expression of certain genes in vivo. In alternate embodiments, double stranded RNA derived from a target gene can block the expression of a target gene in vivo, and ribozymes can be used to process or degrade a target gene of interest. Antisense nucleic acids can be designed to structural genes or regulatory regions thereof.

By "hydrophobic residues" or "nonpolar residues" as used herein is meant valine, leucine, isoleucine, methionine, phenylalanine, tyrosine, and tryptophan.

By "increase in polar character" as used herein is meant any of the following: (1) replacement of hydrophobic residues with neutral polar or charged residues or (2) the replacement of neutral polar residues with charged residues.

By "labeled" herein is meant that a protein has at least one element, isotope or chemical compound attached to enable the detection and/or purification of the protein. In general, labels include, but are not limited to, a) isotopic labels, which may be radioactive or heavy isotopes; b) immune labels, which may be antibodies or antigens; c) colored or fluorescent dyes,) enzymes, e) particles such as colloids, magnetic particles, etc.

By "linker", "linker sequence", "spacer", "tethering sequence" or grammatical equivalents thereof, herein is meant a molecule or group of molecules (such as a monomer or polymer) that connects two molecules and often serves to place the two molecules in a preferred configuration. In one aspect of this embodiment, the linker is a peptide bond. Choosing a suitable linker for a specific case where two polypeptide chains are to be connected depends on various parameters, e.g., the nature of the two polypeptide chains (e.g., whether they naturally oligomerize (e.g., form a dimer or not), the distance between the N- and the C-termini to be connected if known from three-dimensional structure determination, and/or the stability of the linker towards proteolysis and oxidation. Furthermore, the linker may contain amino acid residues that provide flexibility. Thus, the linker peptide may predominantly include the following amino acid residues: Gly, Ser, Ala, or Thr. These linked RANKL proteins have constrained hydrodynamic properties, that is, they form constitutive dimers) and thus efficiently interact with other naturally occurring RANKL proteins to form a dominant negative heterotrimer.

The linker peptide should have a length that is adequate to link two RANKL variant monomers in such a way that they assume the correct conformation relative to one another so that they retain the desired activity as antagonists of the native RANKL protein. Suitable lengths for this purpose include at least one and not more than 30 amino acid residues. Preferably, the linker is from about 1 to 30 amino acids in length, with linkers of 1, 2, 3, 4, 5, 6, 7, 8, 9, 10, 11, 12, 13, 14, 15, 16, 17, 18 19 and 20 amino acids in length being preferred. See also WO 01/25277, incorporated herein by reference in its entirety.

In addition, the amino acid residues selected for inclusion in the linker peptide should exhibit properties that do not interfere significantly with the activity of the polypeptide. Thus, the linker peptide on the whole should not exhibit a charge that would be inconsistent with the activity of the polypeptide, or interfere with internal folding, or form bonds or other interactions with amino acid residues in one or more of the monomers that would seriously impede the binding of receptor monomer domains.

Useful linkers include glycine-serine polymers (including, for example, (GS)n, (GSGGS)n (GGGGS)n and (GGGS)n, where n is an integer of at least one), glycine-alanine polymers, alanine-serine polymers, and other flexible linkers such as the tether for the shaker potassium channel, and a large variety of other flexible linkers, as will be appreciated by those in the art. Glycine-serine polymers are preferred since both of these amino acids are relatively unstructured, and therefore may be able to serve as a neutral tether between components. Secondly, serine is hydrophilic and therefore able to solubilize what could be a globular glycine chain. Third, similar chains have been shown to be effective in joining subunits of recombinant proteins such as single chain antibodies.

Suitable linkers may also be identified by screening databases of known three-dimensional structures for naturally occurring motifs that can bridge the gap between two polypeptide chains. Another way of obtaining a suitable linker is by optimizing a simple linker, e.g., (Gly4Ser)n, through random mutagenesis. Alternatively, once a suitable polypeptide linker is defined, additional linker polypeptides can be created by application of PDA™ technology to select amino acids that more optimally interact with the domains being linked. Other types of linkers that may be used in the present invention include artificial polypeptide linkers and inteins. In another preferred embodiment, disulfide bonds are designed to link the two receptor monomers at inter-monomer contact sites. In one aspect of this embodiment the two receptors are linked at distances <5 Angstroms. In addition, the variant RANKL polypeptides of the invention may be further fused to other proteins, if desired, for example to increase expression or stabilize the protein.

By "mixed trimers" (frequently used interchangeably with mixed oligomers herein) is meant trimers that are composed of one or two monomers of wild type RANKL and one or two monomers of variant RANKL protein.

By "nonconservative modification" herein is meant a modification in which the wild type residue and the mutant residue differ significantly in one or more physical properties, including hydrophobicity, charge, size, and shape. For example, modifications from a polar residue to a nonpolar residue or vice-versa, modifications from positively charged residues to negatively charged residues or vice versa, and modifications from large residues to small residues or vice versa are nonconservative modifications.

Conservative modifications are generally those shown below, however, as is known in the art, other substitutions may be considered conservative:

| | |
|---|---|
| Ala | Ser |
| Arg | Lys |
| Asn | Gin, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Modifications of the proteins are preferably substitutions and may include those to surface, boundary and core areas of a TNFSF member. See, for example, U.S. Pat. Nos. 6,188,965 and 6,269,312, hereby incorporated by reference. In another preferred embodiment, modifications may be made to surface residues, particularly when alterations to binding properties are desired (either to other monomers or to the receptor).

By "nucleic acid" herein is meant DNA, RNA, and related molecules, which contain deoxy- and/or ribonucleotides. In some cases, for example for use with antisense nucleic acids, nucleic acid analogs may be used.

By "operably linked" herein is meant that a nucleic acid is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation.

By "patient" herein is meant both humans and other animals, particularly mammals as outlined herein, and non-animal organisms, with humans being preferred.

By "pharmaceutically acceptable salt" as used herein refers to those salts that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like, or derived from inorganic bases such as sodium, potassium, lithium, ammonium, calcium, magnesium, iron, zinc, copper, manganese, aluminum salts and the like, as well as salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

By "polar residues" herein is meant serine, threonine, histidine, aspartic acid, asparagine, glutamic acid, glutamine, arginine, and lysine.

By "protein" herein is meant at least two covalently attached amino acids, which includes proteins, polypeptides, oligopeptides and peptides. The protein may be made up of naturally occurring amino acids and peptide bonds, or synthetic peptidomimetic structures, i.e., "analogs" such as peptoids [see Simon et al., Proc. Natl. Acd. Sci. U.S.A. 89(20: 9367-71 (1992)], generally depending on the method of synthesis. For example, homo-phenylalanine, citrulline, and noreleucine are considered amino acids for the purposes of the invention. "Amino acid" also includes amino acid residues such as proline and hydroxyproline. Both D- and L-amino acids may be utilized.

By "RANKL non-agonists" or grammatical equivalents thereof herein is meant variants of RANKL that do not appreciably activate RANK receptor. In a preferred embodiment, activation of the RANK receptor by non-agonistic RANKL variants is at most 50% of the activation that would be attained with an equal amount of wild type RANKL protein, with at least less than 20% or 10% being especially preferred.

By "RANKL related disorder" or "RANKL responsive disorder" or grammatical equivalents thereof herein is meant a disorder that may be ameliorated, prevented, or treated by the administration of a pharmaceutical composition comprising a variant RANKL protein. RANKL-related diseases and disorders include but are not limited to: osteoporosis (postmenopausal) caused by elevated RANKL through oophorectomy; osteoporosis (glucocorticoid-induced) caused by elevated RANKL through glucocorticoids; rheumatoid arthritis associated with elevated RANKL in T-cells, synovial fibroblasts, and bone marrow stroma; bone loss in hyperparathyroidism caused by elevated RANKL through parathyroid hormone (PTH); Paget's disease (sporadic) caused by elevated RANKL; osteoclastoma associated with elevated RANKL; multiple myeloma associated with elevated RANKL; breast cancer associated with elevated RANKL; disuse osteopenia; bone loss due to weightlessness, malnutrition, periodontal disease, alcohol use, androgens, estrogens, chemotherapy, and parathyroid hormone; Gaucher's disease, Langerhans' cell histiocytosis, spinal cord injury, acute septic arthritis, osteomalacia, Cushing's syndrome, monoostotic fibrous dysplasia, polyostotic fibrous dysplasia, periodontal reconstruction, and bone fractures; multiple myeloma; osteolytic bone cancers such as breast cancer, lung cancer, kidney cancer and rectal cancer; bone metastasis, bone pain management, and humoral malignant hypercalcemia, among others. Additional RANKL responsive disorders, include but are not limited to prosthesis fitting, prevention of prosthesis loosening, craniofacial reconstruction and in the treatment of other fractures, for example, hip, spine and long bone fractures among others. Additional RANKL responsive disorders, include but are not limited to autoimmune diseases such as systemic lupus erythematosus, inflammatory bowel disease, diabetes, multiple sclerosis, rheumatoid arthritis, and ankylosing spondylitis; as well as transplantation rejection, viral infections, and cancer. Other disease indications, which the variant RANKL proteins of the present invention may treat include, but are not limited to: hematologic neoplasisas and neoplastic-like conditions for example, Hodgkin's lymphoma; non-Hodgkin's lymphomas (Burkitt's lymphoma, small lymphocytic lymphoma/chronic lymphocytic leukemia, mycosis fungoides, mantle cell lymphoma, follicular lymphoma, diffuse large B-cell lymphoma, marginal zone lymphoma, hairy cell leukemia and lymphoplasmacytic leukemia), tumors of lymphocyte precursor cells, including B-cell acute lymphoblastic leukemia/lymphoma, and T-cell acute lymphoblastic leukemia/lymphoma, thymoma, tumors of the mature T and NK cells, including peripheral T-cell leukemias, adult T-cell leukemia/T-cell lymphomas and large granular lymphocytic leukemia, Langerhans cell histocytosis, myeloid neoplasias such as acute myelogenous leukemias, including AML with maturation, AML without differentiation, acute promyelocytic leukemia, acute myelomonocytic leukemia, and acute monocytic leukemias, myelodysplastic syndromes, and chronic myeloproliferative disorders, including chronic myelogenous leukemia.

Additional diseases or disorders which may be treated by the variant RANKL proteins of the present invention, include but are not limited to cancers which rarely or never metastasize to bone and in which hypercalcemia generally does not occur, for example: tumors of the central nervous system, e.g., brain tumors (glioma, neuroblastoma, astrocytoma, medulloblastoma, ependymoma, and retinoblastoma), solid tumors (nasopharyngeal cancer, basal cell carcinoma, pancreatic cancer, cancer of the bile duct, Kaposi's sarcoma, testicular cancer, uterine, vaginal or cervical cancers, ovarian cancer, primary liver cancer or endometrial cancer, and tumors of the vascular system (angiosarcoma and hemagiopericytoma), among others.

By "reduction in hydrophobicity" as used herein is meant the removal of hydrophobic chemical groups.

By "soluble expression" or grammatical equivalents thereof as used herein is meant that the RANKL variant protein is expressed in soluble form (as opposed to forming aggregates or inclusion bodies). In a preferred embodiment, greater than 5% of the expressed RANKL variant protein is soluble, with at least 50%, 75% or 90% being especially preferred. In an alternate embodiment, the total yield of soluble protein is at least 0.01 mg/L of culture, or preferably at least 0.1 or 1.0 mg/L of culture. In a preferred embodiment, RANKL proteins that express solubly can be released, in soluble form, from cells using any non-denaturing buffer (that is, buffers that contain less than 1 M guanidinium or urea).

By "treatment" herein is meant to include therapeutic treatment, as well as prophylactic, or suppressive measures for the disease or disorder. Thus, for example, successful administration of a variant RANKL protein prior to onset of the disease may result in treatment of the disease. As another example, successful administration of a variant RANKL protein after clinical manifestation of the disease to combat the symptoms of the disease comprises "treatment" of the disease. "Treatment" also encompasses administration of a variant RANKL protein after the appearance of the disease in order to eradicate the disease. Successful administration of an agent after onset and after clinical symptoms have developed, with possible abatement of clinical symptoms and perhaps amelioration of the disease, further comprises "treatment" of the disease.

By "wild-type" herein is meant an amino acid sequence or a nucleotide sequence that is found in nature and includes allelic variations; that is, an amino acid sequence or a nucleotide sequence that has not been intentionally modified. In a preferred embodiment, the wild-type sequence is the most prevalent human sequence.

DETAILED DESCRIPTION OF THE INVENTION

The present invention is directed to variant RANKL monomers and mixed oligomers containing the variant RANKL monomers that modify receptor activation. In preferred embodiments, the mixed oligomers have either antagonist or agonist activity. The therapeutic strategy is based on the design of novel RANKL variants that have altered receptor binding and/or activation properties as compared to naturally occurring RANKL proteins, and the ability to oligomerize with naturally occurring RANKL proteins. In other words, RANKL variants that result in reduced activation (preferably do not substantially activate) RANKL receptors (as compared to a naturally occurring RANKL protein) will exchange with at least one naturally occurring RANKL protein and sequester it into reduced or inactive hetero-oligomers, inhibiting the oligomer's biological activity, e.g. the ability to bind and/or activate the receptor. Similarly, agonists can be done in a similar manner.

The RANKL variants of the present invention may be designed by modifying RANKL proteins at key receptor contact points in order to modify (disrupt or enhance, depending on the desired outcome) the ability of the ligand to either bind or activate the receptor. The exchange and physical interaction of these oligomeric RANKL variants with naturally occurring RANKL proteins results in altered activity of the naturally occurring RANKL oligomeric proteins. To help accomplish this goal more effectively; the RANKL variants can be designed to preferentially hetero-oligomerize with naturally occurring RANKL proteins. Alternatively, the variants may be designed to bind each other and "swamp" out the effect of any naturally occurring RANKL proteins due to the amount of variant oligomers present; e.g. equilibria favors the binding of the variant mixed oligomers.

Accordingly, the present invention provides methods and compositions utilizing variants of an extracellular domain of a RANKL protein.

One aspect of the present invention is the generation of variants of human RANKL that express as soluble components from host systems, preferably bacteria and mammalian host cells such as CHO cells. A further aspect of the present invention is the generation of variants of human RANKL that act as antagonists of the wild type RANKL and/or RANK or variants of human RANKL that act as superagonists of RANK signaling.

Rational design of novel RANKL variants may be achieved by using, for example, Protein Design Automation® (PDA™) technology. (See U.S. Pat. Nos. 6,188,965; 6,269,312; 6,403,312; 6,188,965; 6,269,312; 6,403,312; 6,177,318; 7,315,786; WO 98/47089 and U.S. Ser. Nos. 60/104,612, 60/158,700, 60/181,630, 60/186,904, 09/782,004 and 60/347,772, 60/347,772, and 10/218,102; and PCT/US01/218,102 and U.S. Ser. No. 60/345,805; U.S. Ser. No. 60/373,453 and 60/374,035, all references expressly incorporated herein in their entirety.)

PDA™ technology couples computational design algorithms that generate quality sequence diversity with experimental high-throughput screening to discover proteins with improved properties. The computational component uses atomic level scoring functions, side chain rotamer sampling, and advanced optimization methods to accurately capture the relationships between protein sequence, structure, and function. Calculations begin with the three-dimensional structure of the protein and a strategy to optimize one or more properties of the protein. PDA™ technology then explores the sequence space comprising all pertinent amino acids (including unnatural amino acids, if desired) at the positions targeted for design. This is accomplished by sampling conformational states of allowed amino acids and scoring them using a parameterized and experimentally validated function that describes the physical and chemical forces governing protein structure. Powerful combinatorial search algorithms are then used to search through the initial sequence space, which may constitute $10^{50}$ sequences or more, and quickly return a tractable number of sequences that are predicted to satisfy the design criteria. Useful modes of the technology span from combinatorial sequence design to prioritized selection of optimal single site substitutions. PDA™ technology has been applied to numerous systems including important pharmaceutical and industrial proteins and has a demonstrated record of success in protein optimization PDA™ utilizes three-dimensional structural information. In the most preferred embodiment, the structure of RANKL is obtained by solving its crystal structure or NMR structure by techniques well known in the art. In an alternate preferred embodiment, a homology model of RANKL is built, using methods known to those in the art. For example, a homology model of RANKL can be made using the structure of murine RANKL and the sequence of human RANKL.

Soluble RANKL Variants

In a preferred embodiment, PDA™ technology is utilized for the rational design of RANKL variants that are expressed as soluble proteins, preferably secreted, in host cell systems including prokaryotes and eukaryotes, with preferred embodiments expressing in bacterial host cell systems. Since attempts at soluble bacterial expression of human proteins are often unsuccessful, these soluble variants and the approaches developed to generate them have broad applicability for the field of protein engineering. The methods described herein may be used to generate soluble variants of additional proteins. Furthermore, the generation of soluble RANKL variants enables the development of RANKL variants with novel biological properties, including but not limited to RANKL variants that act as RANKL antagonists.

A variety of strategies may be utilized to design RANKL variants that express solubly in *E. coli*. In a preferred embodiment, three strategies are used: 1) reduce hydrophobicity by replacing solvent-exposed hydrophobic residues with suitable polar residues, 2) increase polar character by replacing neutral polar residues with charged polar residues 3) replace non-disulfide bonded cysteine residues (unpaired cysteines) with suitable non-cysteine residues, and 4) replace residues whose identity is different in murine versus human RANKL. As will be appreciated by those in the art, several alternative strategies could also be utilized. For example, modifications that increase the stability of a protein can sometimes improve solubility by decreasing the population of partially folded or misfolded states. As another example, protein solubility is typically at a minimum when the isoelectric point of the protein is equal to the pH of the surrounding solution. Modifications which perturb the isoelectric point of the protein away from the pH of a relevant environment, such as serum, can therefore serve to improve solubility.

Replacing Solvent-exposed Hydrophobic Residues with Suitable Polar Residues

In a preferred embodiment, solvent exposed hydrophobic residues are replaced with structurally and functionally compatible polar residues. Alanine and glycine may also serve as suitable replacements, constituting a reduction in hydrophobicity. Solvent exposed hydrophobic residues can be defined according to absolute or fractional solvent accessibility, as defined above. It is also possible to use other methods, such as contact models, to identify exposed residues. As used herein, solvent exposed hydrophobic residues in RANKL include, but are not limited to, isoleucine 247 and isoleucine 249.

Especially preferred solvent exposed hydrophobic residues are those residues that have not been implicated in mediating RANKL function, including isoleucine 247.

In an alternate embodiment, preferred polar residues include those that are observed at homologous positions in proteins that are RANKL homologs. In a most preferred embodiment, the RANKL homologs comprise mouse RANKL. Additional preferred RANKL homologs include allelic variants of the human RANKL and RANKL other related species. Alternatively, RANKL homologs may comprise other TNF superfamily members including but not limited to TNF-alpha, LT, TRAIL, BAFF, and CD40L. See also the patent application entitled "DOMINANT NEGATIVE PROTEINS AND METHODS THEREOF, filed on Jan. 6, 2003, Desjarlais, et al.; hereby incorporated by reference in its entirety."

In an especially preferred embodiment, suitable polar residues include only the subset of polar residues with low or favorable energies as determined using PDA™ technology calculations. For example, suitable polar residues may be defined as those polar residues whose energy in the optimal rotameric configuration is more favorable than the energy of the exposed hydrophobic residue observed in the wild type protein at that position, or those polar residues whose energy in the optimal rotameric configuration is among the most favorable of the set of energies of all polar residues at that position.

Preferred polar residues for position 247 include, but are not limited to, glutamine, glutamic acid, lysine, and arginine.

In the most preferred embodiment, suitable polar residues include the subset of polar residues that are deemed suitable by both PDA™ calculations and by sequence alignment data.

Replacing Residues Whose Identities are Different in Murine Versus Human RANKL

In a preferred embodiment, residues whose identities vary between the soluble murine ECD RANKL protein and the insoluble human ECD RANKL protein are mutated to a structurally and functionally compatible residue. Variants derived from the differences between the human and murine RANKL sequences include, but are not limited to, T173A, D174S, S183T, F201L, I207R, D230S, L231V, A232P, E234D, T243V, T254N, Y263N, S285A, E292Q, and R314Q where the human RANKL amino acid is listed first followed by the murine RANKL amino acid.

In an especially preferred embodiment, positions that are hydrophobic in the human sequence and polar in the murine sequence and/or positions that are neutral in the human sequence and charged in the murine sequence are targeted for modification. For example, positions including but not limited to 207 and 263 may be targeted for modification. Position 207 is isoleucine, a nonpolar residue, in the human sequence and arginine, a charged residue, in the mouse sequence, while position 263 is tyrosine, a nonpolar residue, in the human sequence and asparagine, a polar residue, in the mouse sequence.

In a preferred embodiment, suitable residues for the above listed positions are defined as those with low (favorable) energies as calculated using PDA™ technology. For example, suitable residues may be defined as those residues whose energy in the optimal rotameric configuration is more favorable than the energy of the wild type human residue observed at that position, or those residues whose energy in the optimal rotameric configuration is among the most favorable of the set of energies of all residues at that position.

Preferred residues for position 173 include, but are not limited to, glutamic acid and arginine.

Preferred residues for position 183 include, but are not limited to, arginine.

Preferred residues for position 207 include, but are not limited to, aspartic acid, glutamic acid, lysine, and arginine.

Replacing Non-Disulfide Bonded Cysteine Residues with Suitable Non-Cysteine Residues In another preferred embodiment, free cysteine residues (that is, cysteine residues that are not participating in disulfide bonds) are mutated to a structurally and functionally compatible non-cysteine residue. Unpaired cysteines can be identified by visual analysis of the structure or by analysis of the disulfide bond patterns of related proteins. RANKL contains an unpaired cysteine at position 221.

In a preferred embodiment, if the cysteine position is substantially buried in the protein core, suitable non-cysteine residues include alanine and the hydrophobic residues, and if the cysteine position is substantially exposed to solvent, suitable non-cysteine residues include alanine and the polar residues.

In a preferred embodiment, suitable residues are defined as those with low (favorable) energies as calculated using PDA™ technology. For example, suitable residues may be defined as those non-cysteine residues whose energy in the optimal rotameric configuration is more favorable than the energy of the cysteine residue observed in the wild type protein at that position, or those residues whose energy in the optimal rotameric configuration is among the most favorable of the set of energies of all residues at that position.

In a preferred embodiment, suitable residues are defined as those that are observed at homologous positions in proteins that are RANKL homologs. For example, serine is observed at position 221 in RANKL homologs.

In a more preferred embodiment, suitable residues are those, which have both low (favorable) energies as calculated using PDA™ technology and are observed at homologous positions in proteins that are RANKL homologs.

In a most preferred embodiment, cysteine 221 in RANKL is replaced by serine.

Combining Approaches

In the most preferred embodiment, multiple modifications are combined to yield RANKL variants that express solubly in *E. coli*. Especially preferred combinations of modifications include, but are not limited to, I247Q/C221 S, I247E/C221S, I247K/C221S, and I247R/C221 S.

Dominant Negative RANKL Variants

In a preferred embodiment, RANKL variants are engineered to yield significantly reduced affinity and/or signaling for RANK receptor relative to wild type RANKL while maintaining affinity for other RANKL proteins to allow formation of mixed trimers. Such RANKL variants are referred to as “dominant negative RANKL variants” or “DN-RANKL”. The dominant negative RANKL variants act by sequestering the naturally occurring RANKL proteins in mixed heterotrimers that are incapable of appreciably activating the RANK receptor. Consequently, DN-RANKL act to antagonize the action of naturally occurring RANKL. Alternatively, the amount of variant homotrimers “swamps” out the effect of endogeneous homotrimers.

In a preferred embodiment, DN-RANKL variant proteins exhibit decreased biological activity as compared to wild-type RANKL, including but not limited to, decreased binding to the either RANK and/or OPG receptors, decreased activation and/or a loss of osteoclastogenesis and/or costimulatory activity.

In an alternate preferred embodiment, DN-RNAKL variant proteins do not bind to either RANK or OPG receptors.

Variant RANKL proteins that exhibit less than 50% biological activity as compared to wild-type are preferred. More preferred are variant RANKL proteins that exhibit less than 25%, even more preferred are variant proteins that exhibit less than 15%, and most preferred are variant RANKL proteins that exhibit less than 10% of a biological activity of wild-type RANKL. Suitable assays are discussed further below.

Thus, the invention provides variant RANKL proteins with altered binding affinities such that the DN-RANKL proteins will preferentially oligomerize with wild-type RANKL, but do not substantially interact with wild type RANK or OPG receptors. “Preferentially” in this case means that given equal amounts of variant RANKL monomers and wild-type RANKL monomers, at least 25% of the resulting trimers are mixed trimers of variant and wild type RANKL, with at least about 50% being preferred, and at least about 80-90% being particularly preferred. In other words, it is preferable that the affinity of DN-RANKL variants for wild type RANKL is greater than the affinity of a DN-RANKL variant for another DN-RANKL protein or than the affinity of wild type RANKL for another wild type RANKL protein.

For purposes of the present invention, the areas of the wild-type or naturally occurring RANKL molecule to be modified are preferably (but not required to be) selected from the group consisting of the Large Domain (also known as II), Small Domain (also known as I), the DE loop, and the trimer interface. The Large Domain, the Small Domain and the DE loop are three separate receptor contact domains, each made up of several non-contiguous linear segments of the protein. These domains are identified in the RANKL protein by comparison to the receptor interaction domains of Lymphotoxin-alpha and TRAIL, two TNF superfamily homologues of RANKL whose structures (1TNR and 1D0G, respectively) have been defined in complex with their cognate receptors using crystallographic methods. The trimer interface mediates physical interactions between RANKL monomers. Trimerization positions can be identified directly from the crystal structure of the mouse RANKL protein (1JTZ). In a preferred embodiment, positions from one RANKL monomer containing atoms that are within 5 angstroms distance from a neighboring RANKL monomer are designated as trimer interface positions. Modifications may be made solely in one of these areas or in any combination of these and other areas.

The Large Domain preferred positions to be modified include human RANKL positions 172, 187-193, 222-228, 267-270, 297, and 300-302. For the Small Domain, the preferred positions to be modified are 179-183, 233-241. For the DE Loop, the preferred positions to be modified include 246-253, and position 284. The Trimer Interface includes positions 163, 165, 167, 193, 195, 213, 215, 217, 219, 221, 235, 237, 239, 244, 253-264, 268, 271-282, 300, 302, 304-305, 307, 311, and 313-314.

Modifications to Large Domain, Small Domain, or DE loop positions are expected to have direct effects on receptor binding and/or signaling. As will be appreciated by those in the art, additional modifications outside of these domains can also indirectly affect receptor binding and/or signaling.

Modifications at the trimer interface can be engineered to optimize the ability of RANKL variants to hetero-trimerize with wild-type RANKL proteins. In some cases, this can be accomplished with a single substitution at one trimer interface position. In other cases, two or more substitutions at multiple trimer interface positions must be combined. For example, the substitutions W193E and H253E could be made simultaneously in order to create an electrostatic repulsion between two variant RANKL monomers such that the RANKL variants would prefer to interact with a wild-type monomer.

In a preferred embodiment, substitutions, insertions, deletions or other modifications at multiple receptor interaction and/or trimerization domains may be combined. Such combinations are frequently advantageous in that they have additive or synergistic effects on dominant-negative activity. Examples include, but are not limited to, simultaneous substitution of amino acids at the large and small domains (e.g. 225 and 237), large domain and DE loop (e.g. 226 and 249), large domain and trimerization domain (e.g. 225 and 215), or multiple substitutions within a single domain. Additional examples include any and all combinations of substitutions.

In a most preferred embodiment, modifications at receptor interaction and/or trimerization domains are combined with RANKL substitutions that confer soluble *E. coli* expression as described above. Examples of such combinations include but are not limited to: C221S/I247E/E269T, C221S/I247E/F270T, and C221S/I247R/H225N.

While the description herein is focused on RANKL variants, as will be appreciated by those in the art, the embodiments and definitions can be applied to soluble trimerizing proteins additional oligomeric proteins that are involved in signal transduction.

Single Chain Dominant Negative RANKL Variants

An additional embodiment includes linked dimers of the RANKL variants (FIG. 3). The present invention relates to these single chain polypeptides comprising multiple receptor-interaction domains that are modified such that each domain has significantly reduced affinity for the cognate receptor(s). Such linked domains preferably retain association with individual monomer domains such that they will exhibit a dominant-negative phenotype, antagonizing the action of the free monomer domains.

RANKL Proteins As Competitive Inhibitors

In an alternative embodiment, RANKL variants are engineered to yield monomers, dimers, or trimers that bind to the RANK receptor but do not appreciably activate the RANK receptor. These variants compete with naturally occurring RANKL protein for binding to the RANK receptor, thereby limiting the ability of naturally occurring RANKL to bind and activate the RANK receptor. Such RANKL variants are referred to as “competitive inhibitor RANKL variants” or “ciRANKL”.

In a preferred embodiment, ciRANKL comprises two variant RANKL monomers that are covalently connected. Such a construct would block wild type RANKL from binding two of the three subunits that form the RANK receptor. Furthermore, the affinity of a dimeric ciRANKL would likely be higher than an equivalent monomeric ciRANKL, facilitating competition. Linkers include, but are not limited to, polypeptide linkages between N- and C-termini of the domains, linkage via a disulfide bond between monomers, and linkage via chemical cross-linking reagents. Alternatively, the N- and C-termini may be covalently joined by deletion of portions of the N- and/or C-termini and linking the remaining fragments via a linker or linking the fragments directly.

In a preferred embodiment, ciRANKL variant proteins exhibit decreased biological activity as compared to wild-type RANKL, including but not limited to, decreased activation and/or a loss of osteoclastagenesis. Suitable assays include, but are not limited to, those described below. Furthermore, ciRANKL proteins are capable of inhibiting the biological functioning of wild type RANKL.

Variant RANKL proteins that reduce the biological activity of wild-type RANKL by at least 50% are preferred. More preferred are variant RANKL proteins reduce the biological activity of wild type RANKL by 75%. Especially preferred ciRANKL variants reduce the activity of wild-type RANKL by at least 90%.

Thus, the invention provides variant RANKL proteins with altered binding affinities such that the ciRANKL proteins will form monomers or dimers, but not trimers, and will bind to the RANK receptor. In a preferred embodiment, the affinity of ciRANKL for the RANK receptor is greater than the affinity of wild type RANKL for the RANK receptor. It is especially preferred that ciRANKL binds to RANK with at least 10-fold greater affinity than the wild type RANKL.

For purposes of the present invention, the areas of the wild-type or naturally occurring RANKL molecule to be modified are selected from the group consisting of the Large Domain (also known as II), Small Domain (also known as I), the DE loop, and the trimer interface. The Large Domain, the Small Domain and the DE loop are three separate receptor contact domains, each made up of several non-contiguous linear segments of the protein. These domains are identified in the RANKL protein by comparison to the receptor interaction domains of Lymphotoxin-alpha and TRAIL, two TNF superfamily homologues of RANKL whose structures (1TNR and 1D0G, respectively) have been defined in complex with their cognate receptors using crystallographic methods. The trimer interface mediates physical interactions between RANKL monomers. Trimerization positions can be identified directly from the crystal structure of the mouse RANKL protein (1JTZ). In a preferred embodiment, positions from one RANKL monomer containing atoms that are within 5 angstroms distance from a neighboring RANKL monomer are designated as trimer interface positions. Modifications may be made solely in one of these areas or in any combination of these and other areas.

Linkers

In a preferred embodiment, a linker peptide is chosen such that the two RANKL variant monomers assume a conformation that allows binding to the RANK receptor. Linkers are defined above.

RANKL Superagonist Variants

In a preferred embodiment, PDA™ technology is utilized for the rational design of RANKL variants that behave as superagonists. RANKL superagonist variants are RANKL variants that bind to and/or activate the RANK receptor more strongly than the wild type human RANKL does. As a result, RANKL superagonists could be used as a treatment for RANKL-responsive conditions that result from insufficient activity of endogenous RANKL.

In a preferred embodiment, RANKL superagonists exhibit increased biological activity as compared to wild type RANKL, including but not limited to increased binding to RANK receptor, increased activation of the RANK receptor, and/or increase in cytotoxic activity. In a preferred embodiment the RANKL superagonist proteins are at least 10% more active then wild type human RANKL, with at least 50%, 100% or 200% increases in activity being especially preferred. Suitable assays are discussed further below.

For purposes of the present invention, the areas of the wild type or naturally occurring RANKL molecule to be modified are selected from the group consisting of the Large Domain (also known as II), Small Domain (also known as I), the DE loop, and the trimer interface. The Large Domain, the Small Domain and the DE loop are three separate receptor contact domains, each made up of several non-contiguous linear segments of the protein. These domains are identified in the RANKL protein by comparison to the receptor interaction domains of Lymphotoxin-alpha and TRAIL, two TNF superfamily homologues of RANKL whose structures (1TNR and 1D0G, respectively) have been defined in complex with their cognate receptors using crystallographic methods. The trimer interface mediates interactions between RANKL monomers. Trimerization positions can be identified directly from the crystal structure of the mouse RANKL protein (1JTZ). In a preferred embodiment, positions from one RANKL monomer containing atoms that are within 5 angstroms distance from a neighboring RANKL monomer are designated as trimer interface positions. Modifications may be made solely in one of these areas or in any combination of these and other areas.

Generation of Nucleic Acids Encoding RANKL Variants

In a preferred embodiment, nucleic acids encoding RANKL variants are prepared by total gene synthesis, or by site-directed mutagenesis of the DNA encoding wild type or variant RANKL protein. Methods including template-directed ligation, recursive PCR, cassette mutagenesis, site-directed mutagenesis or other techniques that are well known in the art may be utilized.

Using the nucleic acids of the present invention, which encode a variant RANKL protein, a variety of expression vectors can be made. Preferred bacterial expression vectors include but are not limited to pET, pBAD, bluescript, pUC, pQE, pGEX, pMAL, and the like. Generally, these expression vectors include transcriptional and translational regulatory nucleic acid operably linked to the nucleic acid encoding the variant RANKL protein. Transcriptional and translational regulatory sequences may include, but are not limited to, promoter sequences, ribosomal binding sites, transcriptional start and stop sequences, translational start and stop sequences, and enhancer or activator sequences. Furthermore, the vector will typically include a selectable marker such as an antibiotic resistance gene.

A suitable bacterial promoter is any nucleic acid sequence capable of binding bacterial RNA polymerase and initiating the downstream (3') transcription of the coding sequence of the variant RANKL protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter may include naturally occurring promoters of non-bacterial origin that have the ability to bind bacterial RNA polymerase and initiate transcription.

In addition to a functioning promoter sequence, an efficient ribosome binding site is desirable. In *E. coli,* the ribosome binding site is called the Shine-Delgarno (SD) sequence and includes an initiation codon and a sequence 3-9 nucleotides in length located 3-11 nucleotides upstream of the initiation codon.

The expression vector may also include a signal peptide sequence that provides for secretion of the variant RANKL protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria). For expression in bacteria, usually bacterial secretory leader sequences, operably linked to a variant RANKL encoding nucleic acid, are preferred.

The bacterial expression vector may also include a selectable marker gene to allow for the selection of bacterial strains that have been transformed. Suitable selection genes include genes, which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

Suitable expression vectors for non-bacterial expression systems are also well known in the art and can be utilized.

In an alternate embodiment, variant RANKL proteins or fragments thereof may be prepared by chemical synthesis. In such an embodiment, it is not necessary to generate nucleic acids encoding the RANKL variants.

Expression of RANKL Variants

In a most preferred embodiment, the variant RANKL proteins are expressed in bacterial systems, including but not limited to *E. coli.* Bacterial expression systems and methods for their use are well known in the art (see Current Protocols in Molecular Biology, Wiley & Sons, and Molecular Cloning—A Laboratory Manual—3$^{rd}$ Ed., Cold Spring Harbor Laboratory Press, New York (2001)). The choice of codons, suitable expression vectors and suitable host cells will vary depending on a number of factors, and may be easily optimized as needed.

Bacterial expression vectors encoding RANKL variants are transformed into bacterial host cells using techniques well known in the art, such as calcium chloride treatment, electroporation, and others.

In a preferred embodiment, bacterial cultures are grown to mid-log phase and expression is induced, for instance with IPTG. Cells are then harvested after 2-24 hours. Protein can be released from the cells using several methods, including sonication, addition of detergents, French press, etc.

In an alternate embodiment, variant RANKL proteins are expressed in non-bacterial systems, including but not limited to yeast, baculovirus, and mammalian expression systems, as well as in vitro expression systems. Suitable protocols are well known in the art.

Purification of RANKL Variants

In a preferred embodiment, the variant RANKL protein is purified or isolated after expression. Standard purification methods include electrophoretic, molecular, immunological and chromatographic techniques, including ion exchange, hydrophobic, affinity, and reverse-phase HPLC chromatography, and chromatofocusing. For example, the variant RANKL protein may be purified using a standard anti-recombinant protein antibody column. Ultrafiltration and diafiltration techniques, in conjunction with protein concentration, are also useful. For general guidance in suitable purification techniques, see Scopes, R., Protein Purification, Springer-Verlag, NY, 3r ed (1994). The degree of purification necessary will vary depending on the use of the variant RANKL protein. In some instances no purification will be necessary.

Derivitization of RANKL Variants

Once made, the variant RANKL proteins may be covalently or non-covalently modified. Derivatized RANKL variants may exhibit improved solubility, absorption, immunogenicity, pharmacokinetics, and the like. Moieties capable of mediating such effects are disclosed, for example, in Remington's Pharmaceutical Sciences, 16th ed., Mack Publishing Co., Easton, Pa. (1980).

Synthetic Modification

One type of covalent modification includes reacting targeted amino acid residues of a variant RANKL polypeptide with an organic derivatizing agent that is capable of reacting with selected side chains or the N-or C-terminal residues of a variant RANKL polypeptide.

Examples include, but are not limited to, modification to effect binding to human serum albumin, alkylaton of any side chain, lipidation, acetylation, acylation, nitrile derivatives of asparagine or glutamine, sulfoxide derivatives methionine, cysteinyl residues reacted with compounds including alpha-haloacetates, histidyl residues derivatized by reaction with diethylprocarbonate, and lysinyl and amino terminal residues reacted with compounds such as succinic or other carboxylic acid anhydrides.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of lysine, arginine, and histidine side chains [T. E. Creighton, Proteins: Structure and Molecular Properties, W. H. Freeman & Co., San Francisco, pp. 79-86 (1983)], acetylation of the N-terminal amine, and amidation of any C-terminal carboxyl group.

Derivatization with bifunctional agents is useful, for instance, for cross linking a variant RANKL protein to a water-insoluble support matrix or surface for use in the method for purifying anti-variant RANKL antibodies or screening assays. Commonly used cross linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio] propioimidate.

Other modifications may be made to the variant RANKL proteins of the present invention, including modifications to the protein that enhance stability, dosage administration (e.g., amphiphilic polymers, see WO 0141812A2, commercially available from Nobex Corporation), clearance (e.g., PEG, aliphatic moieties that effect binding to HSA), and the like.

Glycosylation

The sequence of RANKL variant proteins can be further modified to add or remove glycosylation sites. For example, O-linked glycosylation sites can be altered by adding or removing one or more serine or threonine residues. N-linked glycosylation sites can be altered by incorporating or removing a canonical N-linked glycosylation site, N-X-Y, where N is asparagine, X is any amino acid except for proline and Y is threonine, serine or cysteine. Another means of increasing the number of carbohydrate moieties on the variant RANKL polypeptide is by chemical or enzymatic coupling of glycosides to the polypeptide. Such methods are described in the art, e.g., in WO 87/05330 published Sep. 11, 1987, and in Aplin and Wriston, CRC Crit. Rev. Biochem., pp. 259-306 (1981).

PEGylation

Another type of covalent modification of variant RANKL comprises linking the variant RANKL polypeptide to one of a variety of nonproteinaceous polymers, e.g., polyethylene glycol ("PEG"), polypropylene glycol, or polyoxyalkylenes, in the manner set forth in U.S. Pat. Nos. 4,640,835; 4,496,689; 4,301,144; 4,670,417; 4,791,192 or 4,179,337. These nonproteinaceous polymers may also be used to enhance the ability of a variant RANKL to disrupt receptor binding or to alter the stability, solubility, pharmacokinetics, and/or immunogenicity of the variant RANKL.

In another preferred embodiment, the location of cysteine, lysine, and/or histidine residues in a RANKL variant is modified in order to control the site of PEG attachment. A variety of coupling chemistries may be used to achieve PEGylation, as is well known in the art. Examples, include but are not limited to, the technologies of Shearwater and Enzon. See, Kinstler et al, Advanced Drug Deliveries Reviews, 54, 477-485 (2002) and M J Roberts et al, Advanced Drug Delivery Reviews, 54, 459-476 (2002), both hereby incorporated by reference.

Optimal sites for modification can be chosen using a variety of criteria, including but not limited to, visual inspection, structural analysis, sequence analysis and molecular simulation. For example, the fractional accessibility of individual residues can be analyzed to identify modification sites that will not disrupt the monomer structure. In additional preferred embodiments, modification sites are chosen such that the distance from the modification site to another RANKL monomer is maximal. In additional embodiments, it is possible that receptor binding disruption may occur and may be beneficial to the activity of the RANKL variants of this invention.

Circular Permutation and Cyclization

In another preferred embodiment, the wild type RANKL or variants generated by the invention may be circularly permuted. All natural proteins have an amino acid sequence beginning with an N-terminus and ending with a C-terminus. The N- and C-termini may be joined to create a cyclized or circularly permutated RANKL proteins while retaining or improving biological properties (e.g., such as enhanced stability and activity) as compared to the wild-type protein. In the case of a RANKL protein, a novel set of N- and C-termini are created at amino acid positions normally internal to the protein's primary structure, and the original N- and C-termini are joined via a peptide linker consisting of from 0 to 30 amino acids in length (in some cases, some of the amino acids located near the original termini are removed to accommodate the linker design). In a preferred embodiment, the novel N- and C-termini are located in a non-regular secondary structural element, such as a loop or turn, such that the stability and activity of the novel protein are similar to those of the original protein. In a further preferred embodiment PDA™ technology may be used to further optimize the RANKL variant, particularly in the regions created by circular permutation. These include the novel N- and C-termini, as well as the original termini and linker peptide. In addition, a completely cyclic RANKL may be generated, wherein the protein contains no termini. This is accomplished utilizing intein technology. Thus, peptides can be cyclized and in particular inteins may be utilized to accomplish the cyclization.

Various techniques may be used to permutate proteins. See U.S. Pat. No. 5,981,200; Maki K, Iwakura M., Seikagaku. January 2001; 73(1): 42-6; Pan T., Methods Enzymol. 2000; 317:313-30; Heinemann U, Hahn M., Prog Biophys Mol Biol. 1995; 64(2-3): 121-43; Harris M E, Pace N R, Mol Biol Rep. 1995-96; 22(2-115-23; Pan T, Uhlenbeck O C., Mar 30, 1993; 125(2): 111-4; Nardulli A M, Shapiro D J. 1993 Winter; 3(4): 247-55, EP 1098257 A2; WO 02/22149; WO 01/51629; WO 99/51632; Hennecke, et al., 1999, J. Mol. Biol., 286, 1197-1215; Goldenberg et al J. Mol. Biol 165, 407-413 (1983); Luger et al, Science, 243, 206-210 (1989); and Zhang et al., Protein Sci 5, 1290-1300 (1996); all hereby incorporated by reference.

Fusion Constructs

Variant RANKL polypeptides of the present invention may also be fused to another, heterologous polypeptide or amino acid sequence to form a chimera. The chimeric molecule may comprise a fusion of a variant RANKL polypeptide with an immunoglobulin or a particular region of an immunoglobulin such as the Fc or Fab regions of an IgG molecule.). In some embodiments, for example in the creation of animal models of disease, fusion proteins comprising the variant RANKL proteins with other sequences may be done, for example using fusion partners comprising labels (e.g. autofluorescent proteins, survival and/or selection proteins), stability and/or purification sequences, toxins, variant proteins from other members of the superfamily (e.g. analogous to the creation of "bi-specific antibodies") or any other protein sequences of use. Additional fusion partners are described below. In some instances, the fusion partner is not a protein.

In another embodiment, the RANKL variant is fused with human serum albumin to effect an improvement in pharmacokinetics.

In another preferred embodiment, the RANKL variant is conjugated to an antibody, preferably an anti-variant RANKL protein antibody.

In a further embodiment, RANKL is fused to a cytotoxic agent. In this method, the RANKL fusion acts to target the cytotoxic agent to tumor tissue or cells, resulting in a reduction in the number of afflicted cells. Such an approach thereby reduces symptoms associated with cancer and RANKL protein related disorders. Cytotoxic agents include, but are not limited to, diphtheria A chain, exotoxin A chain, ricin A chain, abrin A chain, curcin, crotin, phenomycin, enomycin and the like, as well as radiochemicals.

Peptide Tags

Various tag polypeptides and their respective antibodies are well known in the art. Epitope tags may be placed at the amino-or carboxyl-terminus of the variant RANKL proteins to enable antibody detection. Also, the epitope tag enables the variant RANKL protein to be readily purified by affinity purification. Examples of peptide tags include, but are not limited to, poly-histidine (poly-His) or poly-histidine-glycine (poly-His-Gly) tags; the flu HA tag polypeptide [Field et al., Mol. Cell. Biol. 8:2159-2165 (1988)]; the c-myc tag [Evan et al., Molecular and Cellular Biology, 5:3610-3616 (1985)]; the Herpes Simplex virus glycoprotein D (gD) tag [Paborsky et al., Protein Engineering, 3(6):547-553 (1990)], the Flag-peptide [Hopp et al., BioTechnology 6:1204-1210 (1988)); the KT3 epitope peptide [Martin et al., Science 255:192-194 (1992)]; tubulin epitope peptide [Skinner et al., J. Biol. Chem. 266:15163-15166 (1991)]; and the T7 gene 10 protein peptide tag [Lutz-Freyermuth et al., Proc. Natl. Acad. Sci. U.S.A. 87:6393-6397 (1990)].

Labels

In one embodiment, the variant RANKL protein is modified by the addition of one or more labels. For example, labels that may be used are well known in the art and include but are not limited to, biotin, tag and fluorescent labels (e.g. fluorescein). These labels may be used in various assays as are also well known in the art to achieve characterization.

Assays

Variant RANKL proteins may be experimentally tested and validated using in vivo and in vitro assays. Suitable assays include, but are not limited to, activity assays and binding assays. For example, RANKL activity assays, such as the tartrate resistant acid phosphatase assay (TRAP; Matsuzaki et al., Biochemical and biophysical research communications 246, 199-204 (1998)) for monitoring the differentiation of pre-osteoclast or RAW264.7 cells into osteoclasts, and the NF-□B (Wei et al., Endocrinology 142, 1290-1295, (2001)) or c-Jun (Srivastava et al., JBC 276, 8836-8840 (2001)) transcription factor activation assays for monitoring signaling through RANK are screens that may be utilized in identifying RANKL variants that are antagonists of wild-type RANKL. Other biological markers for osteoclastogenesis include counting multinucleated TRAP staining cells, calcitonin receptor expression, the presence of ruffled borders on osteoclasts, and cathepsin K expression and activity (see Suda et al., Modulation of Osteoclast Differentiation and Function by the New Members of the Tumor Necrosis Factor Receptor and Ligand Families; Endocrine Reviews 20(3): 345-357 (1999) and Garnero et al., The collagenolytic activity of cathepsin K is unique among mammalian proteinases; Journal of biochemistry 273(48):32347-32352 (1998)).

In a preferred embodiment, binding affinities for the following interactions are determined and compared: 1) variant RANKL oligomer formation, 2) wild type RANKL oligomer formation, 3) variant RANKL binding to RANK, 4) wild type RANKL binding to RANK, 5) variant RANKL binding to OPG, and 6) wild type RANKL binding to OPG. Suitable assays include, but are not limited to, quantitative comparisons comparing kinetic and equilibrium binding constants. The kinetic association rate (Kon) and dissociation rate (Koff), and the equilibrium binding constants (Kd) may be determined using surface plasmon resonance on a BIAcore instrument following the standard procedure in the literature [Pearce et al., Biochemistry 38:81-89 (1999)]. Several alternative methods can also be used to determine binding affinity and kinetics.

RANKL variants can also be tested to determine whether they are capable of forming mixed oligomers including but not limited to mixed trimers. In a preferred embodiment, this is accomplished by labeling wild type RANKL and variant RANKL with distinguishable tags, combining wild type and variant RANKL, and screening for oligomers that contain both tag types. For example, FLAG-tagged wild type RANKL and His-tagged variant RANKL can be combined, and sandwich ELISAs can be performed to identify trimers that contain both FLAG and His tag. Another alternative is to run native gels and perform Western blots using both anti-FLAG and anti-His tag antibodies. This method relies on the fact that FLAG and His tags significantly perturb protein migration in native gels. As will be appreciated by those in the art, many alternate protocols could also be used to measure the formation of mixed trimers.

Therapeutic Application of RANKL Variants

Once made, the variant RANKL proteins and nucleic acids of the invention find use in a number of applications. In a preferred embodiment, the variant RANKL proteins are administered to a patient to treat a RANKL related disorders.

Pharmaceutical Composition

The pharmaceutical compositions of the present invention comprise a variant RANKL protein in a form suitable for administration to a patient. In the preferred embodiment, the pharmaceutical compositions are in a water-soluble form, for example as pharmaceutically acceptable salts. Particularly preferred are the ammonium, potassium, sodium, calcium, and magnesium salts.

The pharmaceutical compositions may also include one or more of the following: carrier proteins such as serum albumin; buffers such as NaOAc; fillers such as microcrystalline cellulose, lactose, corn and other starches; binding agents; sweeteners and other flavoring agents; coloring agents; and polyethylene glycol. Additives are well known in the art, and are used in a variety of formulations.

In a further embodiment, the variant RANKL proteins are added in a micellular formulation; see U.S. Pat. No. 5,833,948, hereby expressly incorporated by reference in its entirety.

Combinations of pharmaceutical compositions may be administered. Moreover, the compositions may be administered in combination with other therapeutics.

Depending upon the manner of introduction, the pharmaceutical composition may be formulated in a variety of ways. The concentration of the therapeutically active variant RANKL protein in the formulation may vary from about 0.1 to 100 weight %. In another preferred embodiment, the concentration of the variant RANKL protein is in the range of 0.003 to 1.0 molar, with dosages from 0.03, 0.05, 0.1, 0.2, and 0.3 millimoles per kilogram of body weight being preferred.

Also, sustained release or controlled release formulations may be used for the compositions of the present invention. For example, ProLease® (commercially available from Alkermes) a microsphere-based delivery system composed of the desired bioactive molecule incorporated into a matrix of poly-DL-lactide-co-glycolide (PLG) and other pharmaceutically compatible polymeric matrices may be used to create sustained release formulations.

Route of Administration

The administration of the variant RANKL proteins of the present invention, preferably in the form of a sterile aqueous solution, may be done in a variety of ways, including, but not limited to, orally, subcutaneously, intravenously, intranasally, intraotically, transdermally, topically (e.g., gels, salves, lotions, creams, etc.), intraperitoneally, intramuscularly, intrapulmonary (e.g., AERx®) inhalable technology commercially available from Aradigm or Inhance™ pulmonary delivery system commercially available from Inhale Therapeutics), vaginally, rectally, or intraocularly. In some instances, for example, in the treatment of wounds, inflammation, etc., the variant RANKL protein may be directly applied as a solution or spray. Depending upon the manner of introduction, the pharmaceutical composition may be formulated in a variety of ways.

Dosing

In a preferred embodiment, a therapeutically effective dose of a variant RANKL protein is administered to a patient in need of treatment. The exact dose will depend on the purpose of the treatment, and will be ascertainable by one skilled in the art using known techniques. As is known in the art, adjustments for variant RANKL protein degradation, systemic versus localized delivery, and the rate of new protease synthesis, as well as the age, body weight, general health, sex, diet, time of administration, drug interaction and the severity of the condition may be necessary, and will be ascertainable with routine experimentation by those skilled in the art.

Gene Therapy

Similarly, nucleic acid encoding the variant RANKL proteins (including both the full-length sequence, partial sequences, or regulatory sequences of the variant RANKL coding regions) may be administered in gene therapy applications.

In a preferred embodiment, the nucleic acid encoding the variant RANKL proteins (including both the full-length sequence, partial sequences, or regulatory sequences of the variant RANKL coding regions) may also be used in gene therapy. In gene therapy applications, genes are introduced into cells in order to achieve in vivo synthesis of a therapeutically effective genetic product, for example for replacement of a defective gene. Antisense RNA and DNA can be used as therapeutic agents for blocking the expression of certain genes in vivo. It has already been shown that short antisense oligonucleotides can be imported into cells where they act as inhibitors (see Zamecnik et al., Proc. Natl. Acad. Sci. U.S.A. 83:4143-4146 (1986)). The oligonucleotides can be modified to enhance their uptake, e.g. by substituting their negatively charged phosphodiester groups by uncharged groups.

There are a variety of techniques available for introducing nucleic acids into viable cells. The currently preferred in vivo gene transfer techniques include transfection with viral (typically retroviral) vectors and viral coat protein-liposome mediated transfection [Dzau et al., Trends in Biotechnology 11:205-210 (1993)]. In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem. 262:4429-4432 (1987); and Wagner et al., Proc. Natl. Acad. Sci. U.S.A. 87:3410-3414 (1990). For review of gene marking and gene therapy protocols see Anderson et al., Science 256:808-813 (1992).

In a preferred embodiment, variant RANKL genes are administered as DNA vaccines, either single genes or combinations of variant RANKL genes. Naked DNA vaccines are generally known in the art. Brower, Nature Biotechnology, 16:1304-1305 (1998). Methods for the use of genes as DNA vaccines are well known to one of ordinary skill in the art, and include placing a variant RANKL gene or portion of a variant RANKL gene under the control of a promoter for expression in a patient in need of treatment.

The variant RANKL gene used for DNA vaccines may encode full-length variant RANKL proteins, but more preferably encodes portions of the variant RANKL proteins including peptides derived from the variant RANKL protein. In a preferred embodiment a patient is immunized with a DNA vaccine comprising a plurality of nucleotide sequences derived from a variant RANKL gene. Similarly, it is possible to immunize a patient with a plurality of variant RANKL genes or portions thereof as defined herein. Without being bound by theory, expression of the polypeptide encoded by the DNA vaccine, cytotoxic T-cells, helper T-cells and antibodies are induced which recognize and destroy or eliminate cells expressing RANKL proteins.

In a preferred embodiment, the DNA vaccines include a gene encoding an adjuvant molecule with the DNA vaccine. Such adjuvant molecules include cytokines that increase the immunogenic response to the variant RANKL polypeptide encoded by the DNA vaccine. Additional or alternative adjuvants are known to those of ordinary skill in the art and find use in the invention.

All references cited herein, including patents, patent applications (provisional, utility and PCT), and publications are incorporated by reference in their entirety.

EXAMPLES

Example 1

Solubility Library Design

A homology model of human RANKL based on the mouse RANKL structure (1JTZ) was analyzed for excessive exposure of non-polar amino acids on the surface of the protein.

The solvent accessible surface area was determined for each amino acid in the structure using algorithms known in the art. The most dramatic exposure of non-polar residues was observed at I247 isoleucine 247 (I247) (138 Å$^2$) and isoleucine 249 (1249) (108 Å$^2$). Indeed, these two isoleucine residues are the only non-polar amino acids with accessible surface area exceeding 100 Å$^2$ in the structural context of trimerized RANKL. I249, however, is located in a region of the protein predicted to interact directly with RANK. Therefore, I247 was chosen for substitution. PDA™ technology predicted that multiple substitutions at I247 were allowed, including the charged amino acids E, K, glutamic acid, lysine and Rarginine, and the polar amino acid Qglutamine. Such substitutions, due to their intrinsically polar nature, are expected to enhance the solubility of the folded protein, and in some cases assist in its proper folding after expression in *E. coli*. The PDA™ technology predictions suggest also that the aforementioned substitutions will preserve tertiary and quaternary structure of the RANKL protein, such that it will retain a large part of its functional activity.

Additional analysis was performed at the primary structure level by comparing the human RANKL sequence (FIGS. 1*a*, 1*b*) to that of the mouse sequence (FIG. 1*c*). Although the mouse and human sequences differ at only sixteen positions (FIG. 2*a*) within our construct, the mouse protein expresses solubly in *E. coli* while the human protein does not. This analysis highlighted additional positions for substitution. Of particular interest are positions containing a non-polar amino acid in the human sequence and a polar amino acid in the mouse sequence. For instance, isoleucine 207 in the human RANKL sequence is replaced by an arginine in the mouse sequence. This substitution was also consistent with PDA™ technology predictions that arginine is favorable at this position in the structure. At several other positions (e.g. threonine 173, serine 183), variability between the mouse and human sequence was used simply as an indicator that substitution at those positions might be compatible with the protein structure. In these cases, PDA™ technology simulations indicated that replacement with charged amino acids is permissible.

Finally, a single unpaired C cysteine exists in the human RANKL protein at position 221. As is well known in the art, unpaired cysteines often lead to unfavorable solution properties of a protein. Therefore, this residue in the human sequence was replaced by serine. A serine at this position is predicted by PDA™ technology simulations to be favorable. In addition, inspection of a multiple sequence alignment of the TNF ligand superfamily reveals that S serine occurs at the equivalent position in other members of the TNF family.

A summary of the amino acid sequences for the human RANKL solubility variants is listed in FIG. 2*b*.

RANKL Solubility Variants Library Construction

The full-length RANKL cDNA was cloned using RT-PCR on lymph node cDNAs. Amino acids 159 to 317 were subcloned into pET33b after PCR-mediated addition of TEV and HIS His tags. The amino acid sequence of this wild-type RANKL is described in FIG. 1*b*.

Site directed mutagenesis was performed on plasmid cDNA clones to introduce the nucleotide changes that result in the amino acid substitutions listed below. The site directed mutagenesis reaction utilized pairs of divergent and overlapping oligonucleotides with nucleotide variations that introduce the specific amino acid changes. These oligonucleotides were extended using Pfu polymerase through multiple rounds of thermal cycling. The template plasmid was degraded using the restriction enzyme DpnI, and the extension products were transformed into TOP10 bacterial cells. Clones were sequenced to confirm the presence of the designed changes and to insure no unwanted modifications were introduced.

RANKL Solubility Variant Bacterial Expression

The human RANKL variants were tested for soluble expression in bacteria (FIGS. 4-8). The sequence confirmed plasmids were transformed into BL21(DE3)pLysS *E. coli* cells. After bacterial growth, induction with IPTG, and expression, the cells were lysed and centrifuged to separate the insoluble and soluble fraction of the lysate. SDS-PAGE and Western blot analysis were performed to characterize expression of the RANKL solubility variants. The results of the expression analysis are summarized in Table 1 below. The results show that the approach to generate soluble human RANKL was successful, as ten variants show soluble expression in bacterial.

TABLE 1

Summary of the bacterial expression analysis using human RANKL solubility variants.

| RANKL Variant | Bacterial Expression |
|---|---|
| Wild-type RANKL (Nter-HIS-Tev-159-317) | No Soluble Expression |
| C221S | No Soluble Expression |
| I247E | No Soluble Expression |
| I247K | No Soluble Expression |
| I247Q | No Soluble Expression |
| T173E/C221S | No Soluble Expression |
| T173R/C221S | No Soluble Expression |
| S183R/C221S | No Soluble Expression |
| I207D/C221S | No Soluble Expression |
| I207E/C221S | No Soluble Expression |
| I207K/C221S | Soluble Expression |
| I207R/C221S | Low Soluble Expression |
| C221S/A232K | Very Low Soluble Expression |
| C221S/I247A | Soluble Expression |
| C221S/I247D | Soluble Expression |
| C221S/I247E | Soluble Expression |
| C221S/I247K | Soluble Expression |
| C221S/I247Q | Soluble Expression |
| C221S/I247R | Low Soluble Expression |
| T173R/S183R/I207R/C221S/I247R | Low Soluble Expression |

Figure 7:
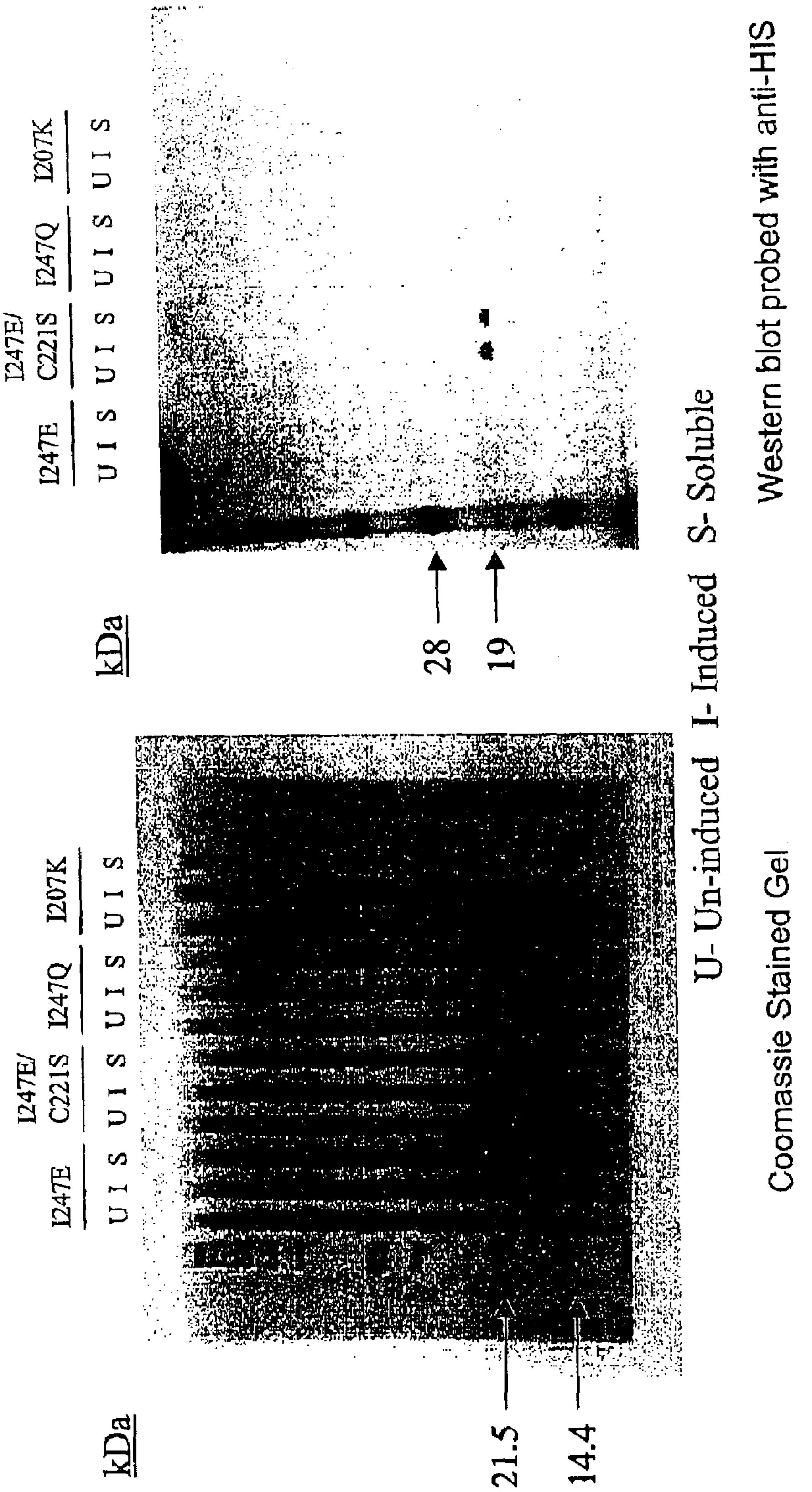
FIG. 7 shows that the C221S mutation when combined with the I247E mutation confers soluble RANKL expression in *E. coli*.

The significance of the C221S change in imparting solubility to the variants was examined by creating variants with the single point modifications C221S, I247Q, I247E, and I247K. Expression analysis showed that soluble expression was observed when C221 S was combined with one of the three changes, I247Q, I247E, and I247K (FIGS. 7, 8).

RANKL Solubility Variant Characterization

Figure 11:
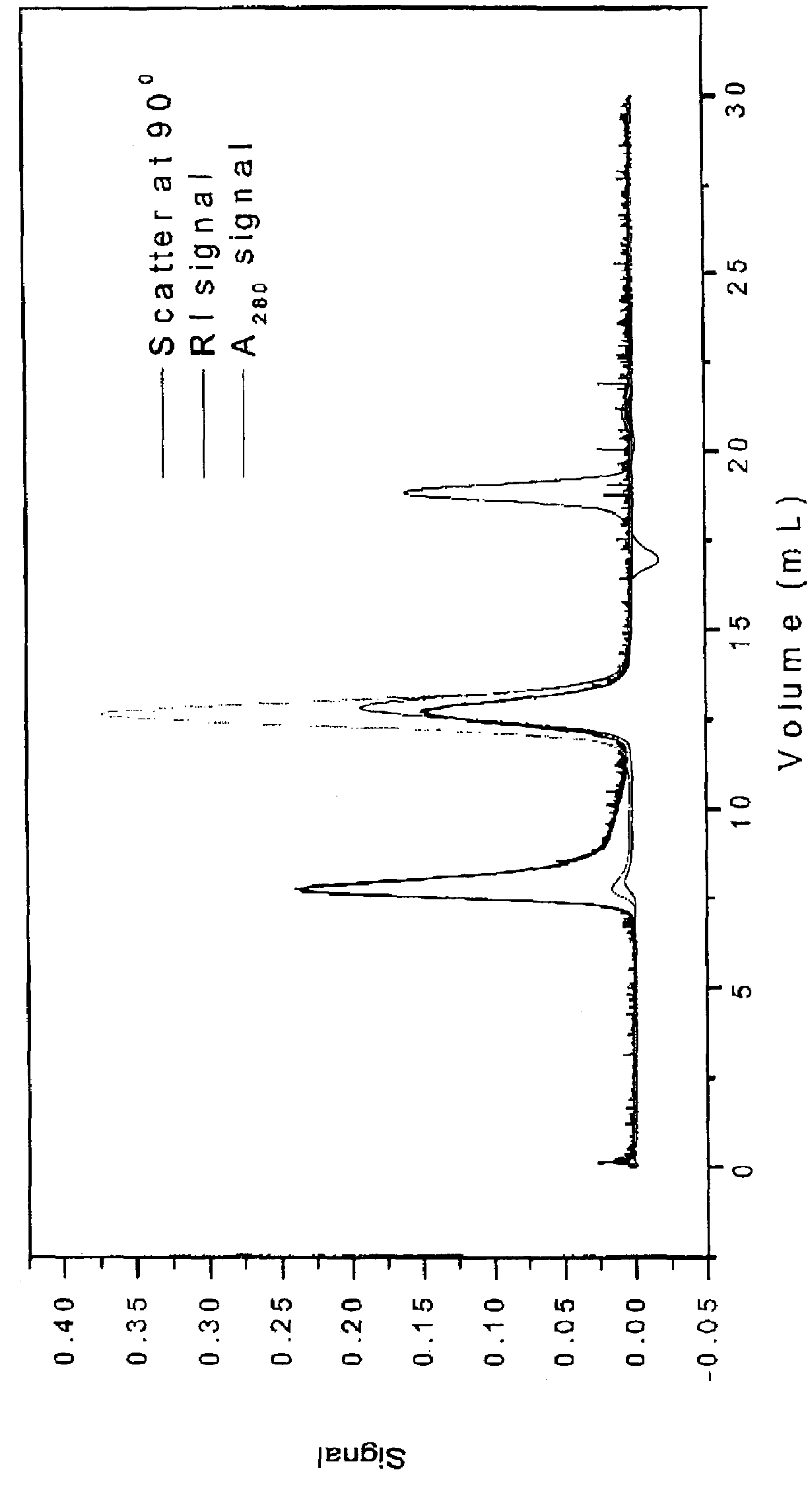
FIG. 11 shows light scattering and size exclusion chromatography data indicating that solubility variant C221S/I247E is 97% trimeric. This analysis demonstrates that the variant protein is folded properly and forms a trimer as is expected for wild-type RANKL protein.
Figure 13:
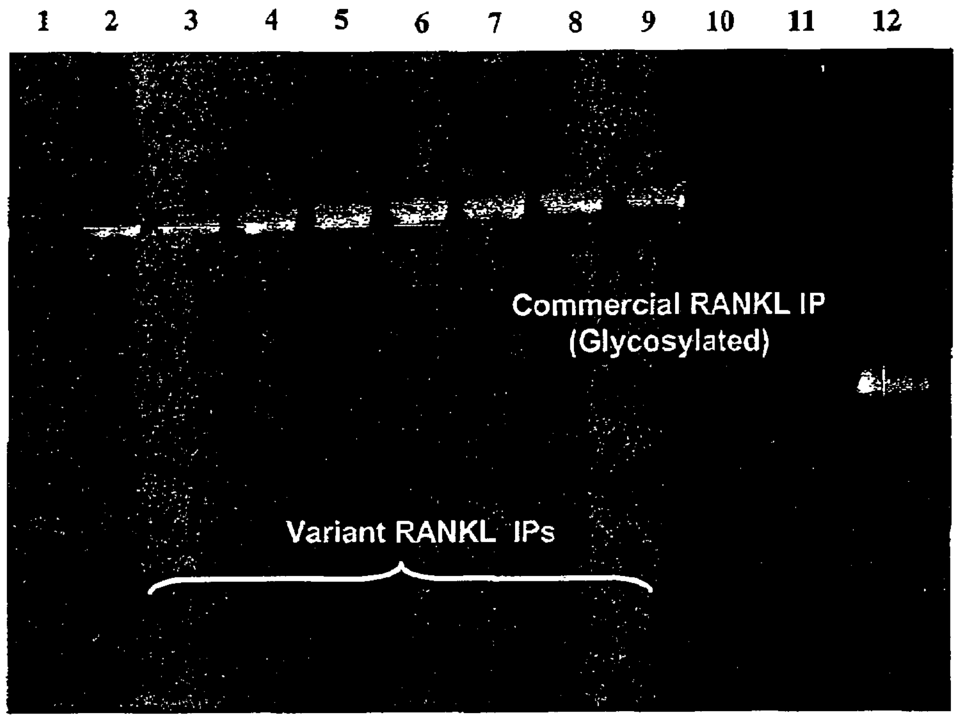
FIG. 13 shows Western analysis indicating that the 6 RANKL solubility variants bind the human receptor RANK in the context of a RANK-Fc fusion construct. The ability of the RANKL variants to bind RANK was assessed in a receptor precipitation experiment. 200 ng of His tagged RANKL was incubated with 1 μg of RANK-Fc for 1 hour at 4° C. in DMEM/10%FBS/10 mM Hepes/0.01% Tween 20. Protein A/G beads were added and allowed to incubate on ice for an additional 1 hr. Immune complexes were collected by centrifugation and washed twice with binding buffer and then once with PBS. Samples were analyzed by SDS-PAGE followed by immunoblotting with an anti-His antibody. His-tagged TNFα was captured by TNFR1-Fc as a positive control and His-tagged TNFα incubated with RANK-Fc acted as the negative control.
Figure 14:
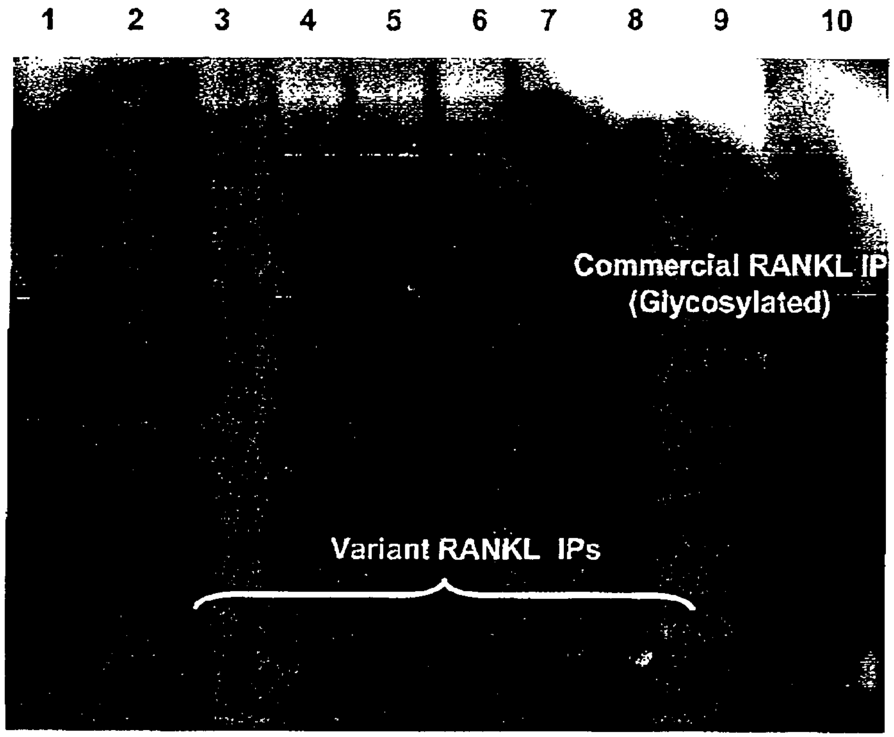
FIG. 14 shows Western analysis indicating that the six RANKL solubility variants bind human OPG-Fc. The ability of variant RANKL to bind OPG was assessed in a immunoprecipitation experiment. 200 ng of His tagged RANKL was incubated with 1 μg of OPG-Fc for 1 hour at 4° C. in DMEM/10% FBS/10 mM Hepes/0.01% Tween 20. Protein A/G beads were added and allowed to incubate on ice for an additional 1 hr. Immune complexes were collected by centrifugation and washed twice with binding buffer and then once with PBS. Samples were analyzed by SDS PAGE followed by immunoblotting with an anti-RANKL antibody.

Six of the highest expressing RANKL solubility variants C221S/I207K, C221S/I247A, C221S/I247D, C221S/I247E, C221S/I247K, and C221S/I247Q were scaled up for protein purification (FIGS. 9, 10) and biochemical characterization. Highly purified protein was collected from the soluble fractions. The proteins were expressed with good yields and determined to be trimeric using dynamic light scattering and size exclusion chromatography (FIG. 11, 12). In addition, the six RANKL solubility variants were shown to bind RANK receptor and the decoy receptor OPG in immunoprecipitation experiments (FIG. 13, 14). The solubility variants express well, can be purified effectively, fold and trimerize as expected, and bind the RANK receptor and OPG receptors.

Figure 15:
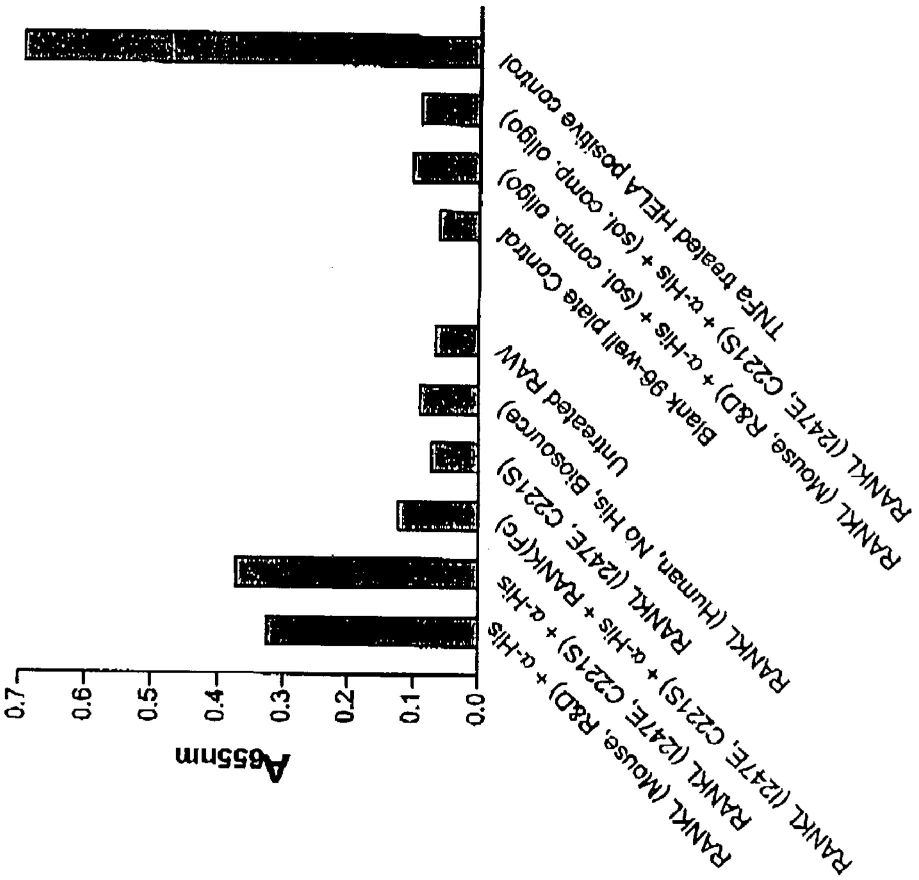
FIG. 15 shows TRANSFACTOR™ (commercially available from Clontech) analysis demonstrating that the RANKL variant (C221S/I247E) activates the NFκB pathway. This analysis indicates that the solubility variant is functionally active.
Figure 16:
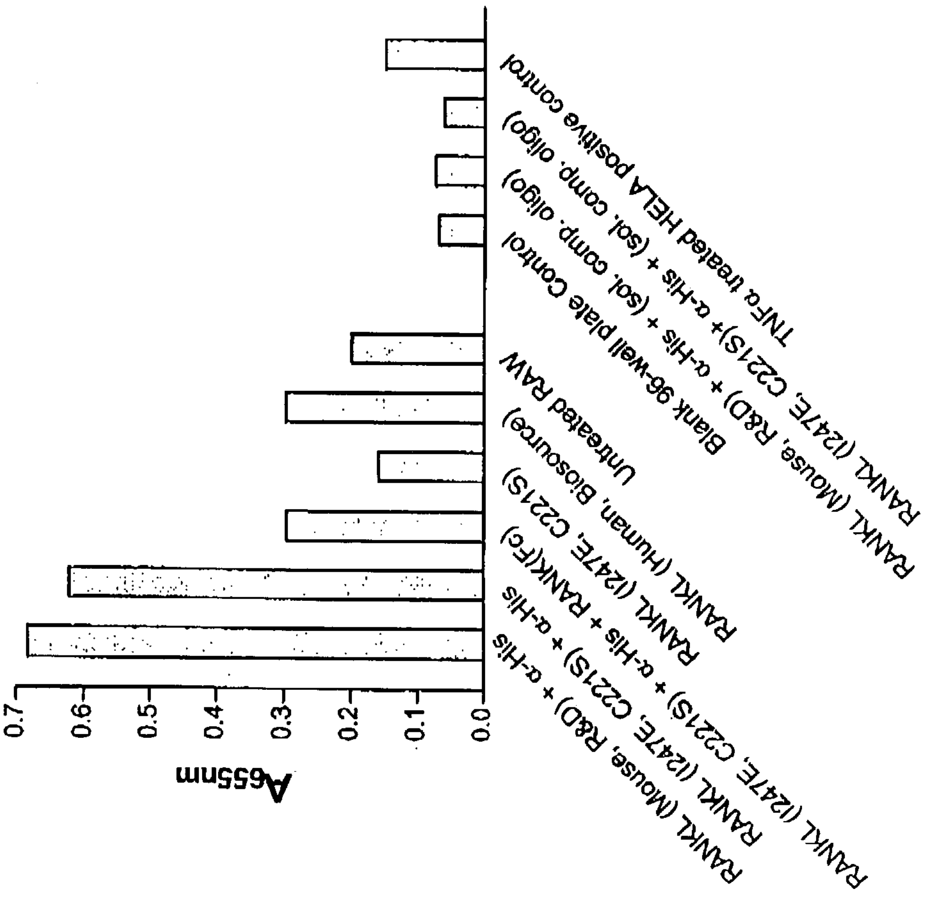
FIG. 16 shows TRANSFACTOR™ (commercially available from Clontech) analysis demonstrating that the RANKL variant (C221S/I247E) activates the JNK pathway. This analysis indicates that the solubility variant is functionally active.

The human RANKL solubility variants were evaluated for their ability to activate the NFκB and JNK pathways in the mouse macrophage monocytic cell line RAW 264.7. RANKL binding to the RANK receptor is known to activate these two pathways (see Gowen, M., Every, J G, and Kumar S. Emerging therapies for osteoporosis. Emerging Drugs, 2000 5(1): p.1-43; Rodan, G A, and Martin T J. Therapeutic approaches to bone disease. Science 2000 289: p. 1508-1514; Hofbauer, L C, Neubauer, A, and Heufelder A E. Receptor activator of nuclear factor-kB ligand and osteoprotegrin. 2001 Cancer 92(3): p.460-470.). Activating these pathways requires a RANKL protein that is folded, trimeric, and capable of binding the RANK receptor. The variant C221S/I247E activates both NFκB and JNK (FIGS. 15, 16) to similar levels as does the wild-type mouse RANKL (commercially available from R&D Systems).

Figure 17:
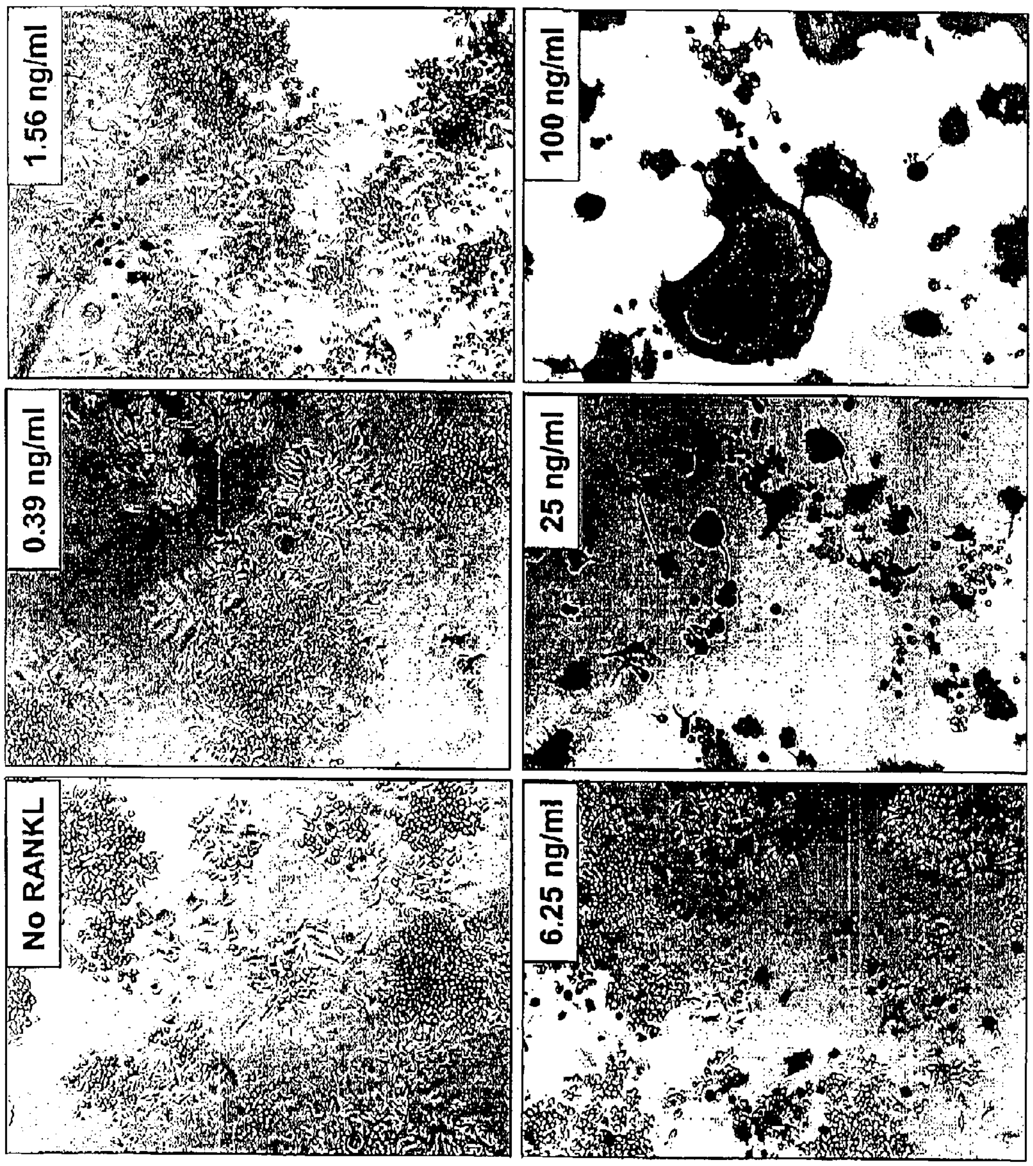
FIG. 17 shows that the RANKL solubility variant C221S/I247E induces osteoclastogenesis in mouse RAW264.7 cells. RAW264.7 cells were plated and incubated with RANKL (C221S/I247E) at the indicated doses for 3 days. Tartrate resistant acid phosphatase (TRAP) staining revealed multinucleated osteoclast cells in a dose-dependant manner.
Figure 18:
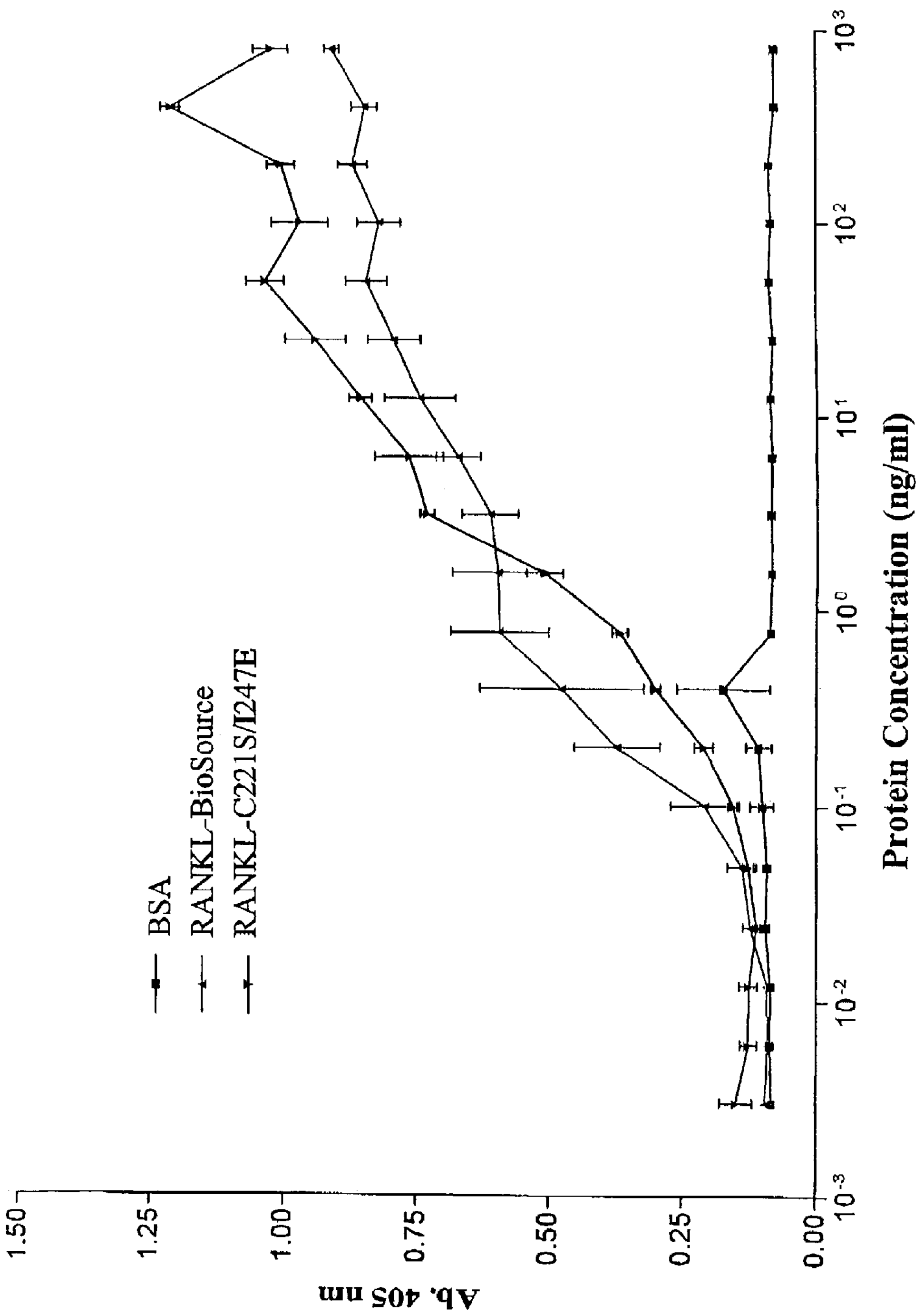
FIG. 18 shows that RANKL solubility variant C221S/I247E induces osteoclastogenesis in mouse RAW264.7 cells. RAW264.7 cells were plated and incubated with proteins at various doses for 3 days. Tartrate resistant acid phosphatase (TRAP) activity measurements using p-nitrophenyl phosphate as substrate show that variant RANKL variant C221/I247E has similar activity to wild-type RANKL commercially available from Biosource Inc.
Figure 19:
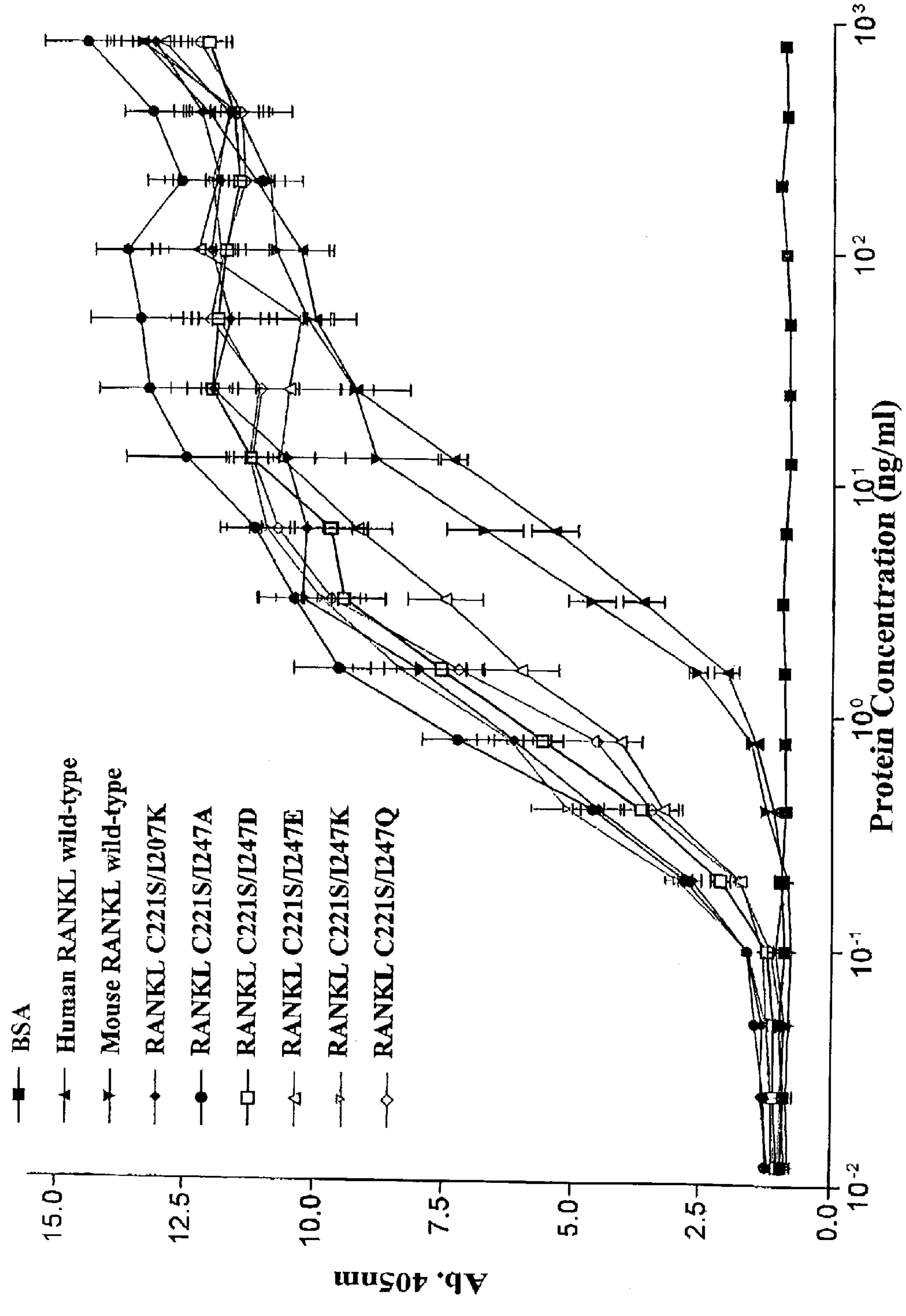
FIG. 19 shows that six RANKL solubility variants induce osteoclastogenesis in mouse RAW264.7 cells. RAW264.7 cells were plated and incubated with proteins at various doses for 3 days. Tartrate resistant acid phosphatase (TRAP) activity measurements using p-nitrophenyl phosphate as substrate show that the RANKL variants are ail active. Human and mouse wild-type RANKL from R&D Systems are included as controls.
Figure 20:
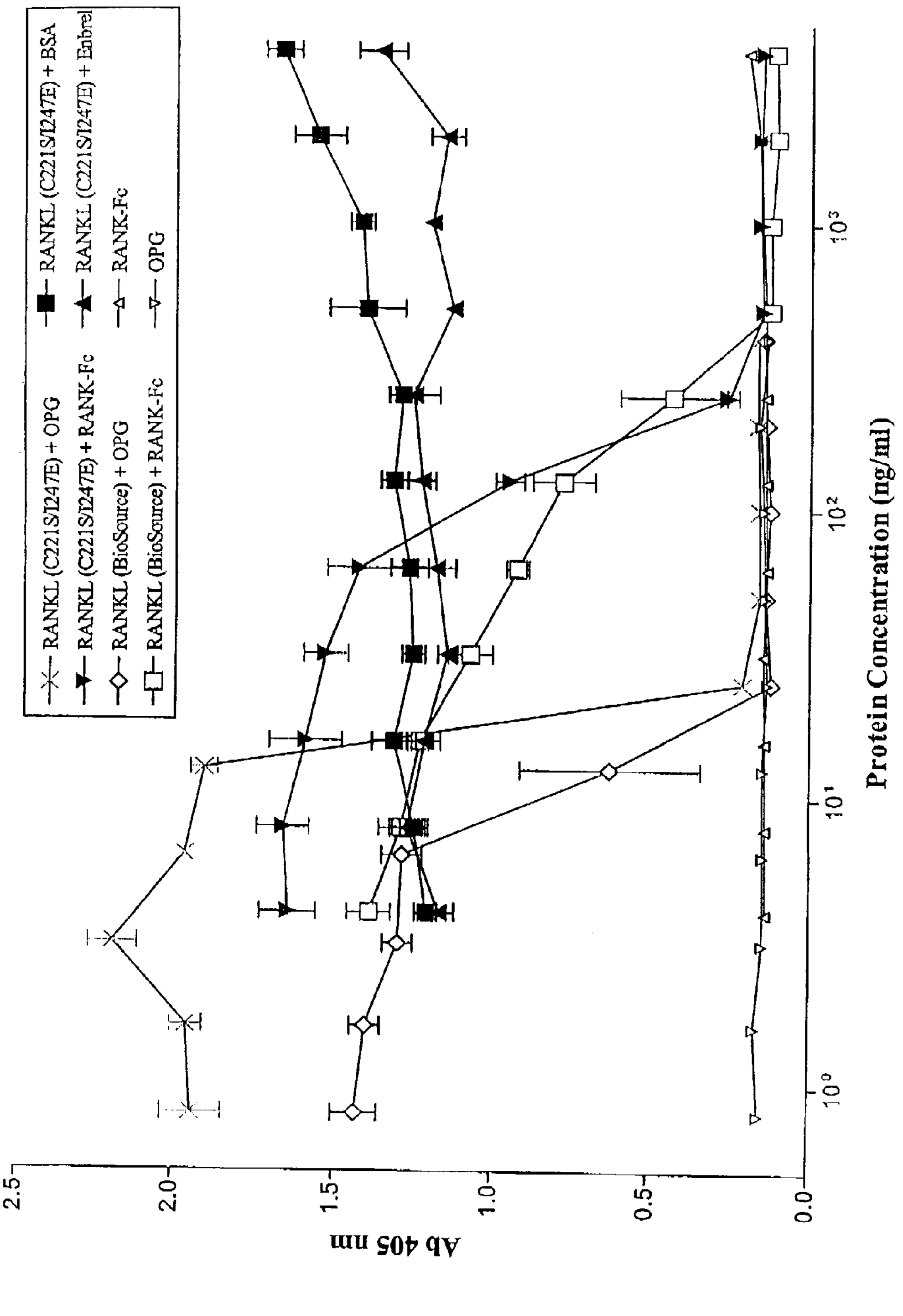
FIG. 20 shows that osteoclastogenesis mediated by RANKL solubility variant C22S/I247E is antagonized by OPG and RANK-Fc. The plots show that commercial RANKL from BioSource is antagonized to the same extent as Xencor solubility variant. The BSA and ENBREL® controls show that the antagonism is specific to RANKL interacting with OPG and RANK-Fc. The RANK-Fc and OPG controls show that the variants do not mediate osteoclastogenesis.

The six human RANKL solubility variants were evaluated for their ability to activate osteoclastogenesis in the mouse monocytic cell line RAW 264.7. The RAW 264.7 cells are known to differentiate into multi-nucleated osteoclasts in a RANKL dependent manner (see Hitoshi H., Sakai E., Kanaoka K., Saito K., Matsuo K. I., Kitaura H., Yoshida N., and Koji Nakayama. U0126 and PD98059, specific inhibitors of MEK, accelerate differentiation of RAW264.7 cells into osteoclast-like cells. J. Biol. Chem, 10.1074/jbc.M208284200). Osteoclast formation can be monitored by the production of Tartrate Resistant Acid Phosphatase (TRAP) from the RAW 264.7 cells as they differentiate. RAW264.7 cells treated with increasing doses of RANKL variant C221S/I247E reveal a dose-dependent increase in the number of multi nucleated cells staining for TRAP (FIG. 17). A quantitative TRAP assay using p-nitrophenyl phosphate as substrate (see Nakagawa N, Kinosaki M, Yamaguchi K, Shima N, Yasuda H, Yano K, Morinaga T, Higashio K. RANK is the essential signaling receptor for osteoclast differentiation factor in osteoclastogenesis. Biochem Biophys Res Commun Dec. 18, 1998; 253(2):395-400.) shows that this variant also mediates osteoclastogenesis with an activity similar to commercially available RANKL made in *E. coli* and refolded from occlusion bodies (commercially available from BioSource) (FIG. 18). All six solubility variants demonstrate similar osteoclastogenesis activity using the TRAP assay (FIG. 19). The ability to antagonize the RANKL solubility variant C221S/I247E with soluble receptor RANK-Fc and OPG-Fc (FIG. 20) confirms that the variant binds RANK and OPG and that the osteoclastogenesis observed in the TRAP assay results from the binding of RANKL to the RANK receptor.

Tartrate-Resistant Acid Phosphatase (TRAP) Activity Bioassay

RAW 264.7 cells (ATCC#TIB-71) were cultured and maintained in 75 $cm^2$ flasks in 5% $CO_2$ humidified incubator at 37° C. in growth media containing α-MEM w/2 mM L-Glutamine (Gibco-BRL#12571-063), 10% Heat Inactivated Fetal Bovine Serum (FBS) (Hyclone#SH30071.03) and Penicillin/Streptomycin (Gibco-BRL#15140-122) 100 units/ml and 100 μg/ml respectively.

Recombinant mouse RANKL (R&D#462-TR), recombinant human soluble RANKL (Biosource#PHP0034), and recombinant human soluble RANKL variants were diluted to their working concentration in assay media consisting of α-MEM w/l-glutamine (Gibco-BRL#12571-063) supplemented with 10% Heat Inactivated Fetal Bovine Serum (FBS) (Hyclone#SH30071.03) and Penicillin/Streptomycin (Gibco-BRL#15140-122) 100 units/ml and 100 μg/ml respectively. 250 μl of RANKL standards and samples were added to 96-well assay plate in triplicate or quadruplicate, and serially diluted 1:2 by transferring 125 μl into subsequent wells containing 125 μl of assay media.

Aspirating the exhausted media, adding 10 ml of pre-warmed media to the flask, and scraping cells from the flask using a cell scraper harvested the cells. The cells were transferred to a 15 ml conical tube, spun at 1000 rpm for 5 minutes and resuspended in 10 ml of assay media. The cells were counted and seeded at density of $1.5\times10^3$/125 μl/well in 96-well assay plate. Assay plates were incubated at 37° C. in 5% $CO_2$ humidified incubator for 72 hours.

The amount of osteoclast-like cells induced from the RAW 264.7 cells was determined by measuring the Tartrate-Resistant Acid Phosphatase (TRAP) activity. TRAP substrate was prepared by adding 20 mg of p-nitrophenol phosphate (pNPP) (ICN#100878) to 10 ml TRAP buffer pH5.0 (100 mM Sodium Acetate, 11.5 mg/ml Sodium Tartrate (ICN#195503)). The media was aspirated off the assay plate and discarded. Cells were fixed for 1 minute with 1:1 ethanol and acetone solution and washed once with 100-150 μl/well of PBS (Hyclone#SH30256.02). 100 μl of TRAP solution was added to each well, and the plate was incubated at 37° C. for 2 hours. The reaction was stopped by adding 50 μl/well of a 0.2N NaOH solution and the absorbance was read at 405 nm. If the absorbance reached saturation, the solutions were diluted 1:5 and read again.

Tartrate-Resistant Acid Phosphatase (TRAP) Cytological Staining

In parallel experiments, osteoclast formation from the RAW 264.7 cells was measured by the presence of Tartrate-Resistant Acid Phosphatase (TRAP) multinucleated positive cells using cytological staining. 0.1 M Acetate buffer was prepared prior to staining by combining 35.2 ml of a 0.2M Sodium Acetate solution, 14.8 ml of a 0.2M Acetic Acid solution and 50 ml of water. 10 ml TRAP buffer pH5.0 (50 mM Acetate Buffer, 30 mM Sodium Tartrate (Sigma#S-8640), 0.1 mg/ml Napthol AS-MX Phosphate Disodium Salt (Sigma#N-5000), 0.1% Triton X-100) was prepared fresh for each assay. The TRAP buffer was warmed in a 37° C. water bath and 0.3 mg/ml of Fast Red Violet LB Stain (Sigma#F-3381) was added and the stain was returned to the 37° C. water bath. The media was aspirated off the assay plate and discarded. The cells were washed once with 150 μl/well of PBS (Hyclone#SH30256.02) and subsequently fixed with 100 μl/well of a 10% Glutaraldehyde solution for 15 minutes at 37° C. The cells were washed twice with 150 µl/well of pre-warmed PBS. 100 µl of the pre-warmed TRAP stain was added to each well and the plate was incubated at 37° C. for 5-10 minutes. The TRAP stain was removed and 100 µl of PBS was added to each well to prevent cells from drying out. TRAP positive multinucleated cells (more than three nuclei) were counted.

Example 2

Antagonistic RANKL Variant Library Design

Antagonistic RANKL variants were generated using the dominant-negative strategy which includes the single chain variety, and by the selection of competitive inhibitor antagonists.

Dominant-Negative RANKL Library Variants

Figure 21:
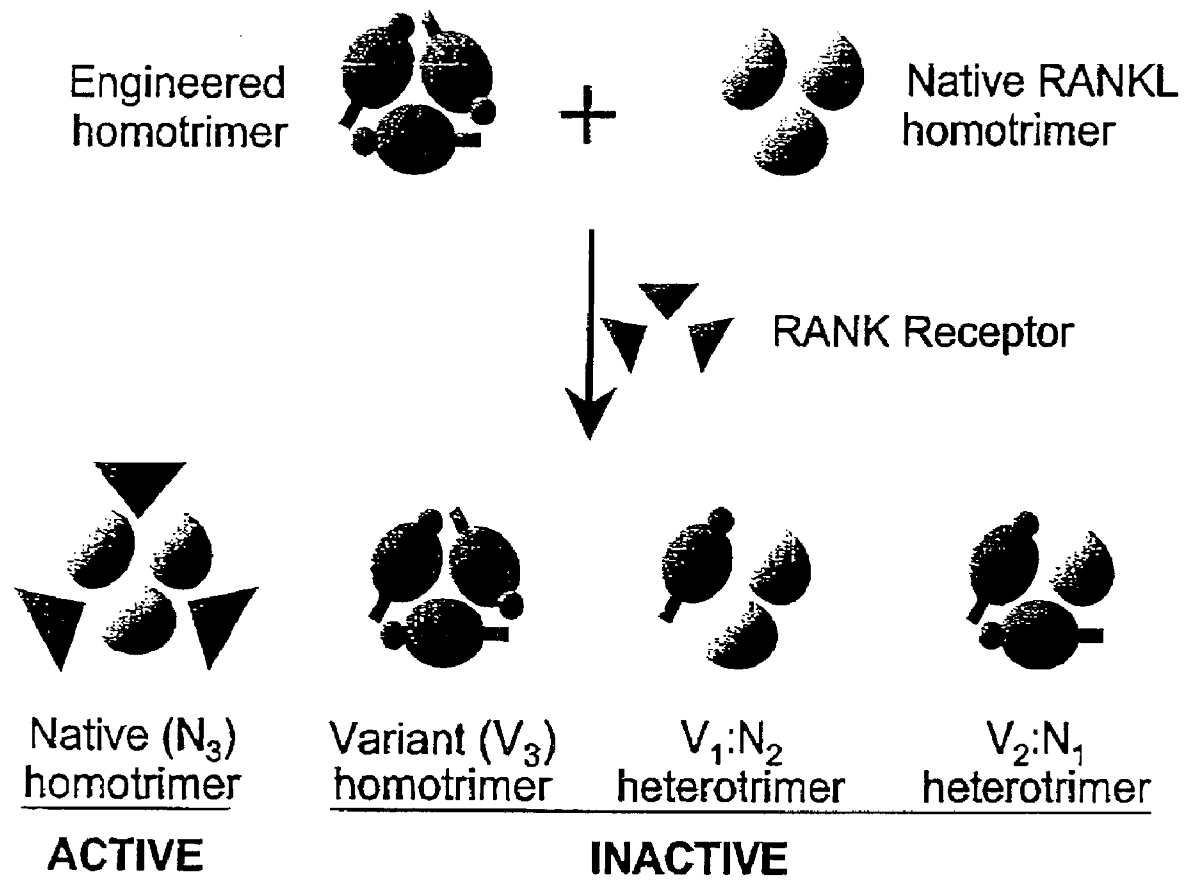
FIG. 21 shows a model for the dominant-negative inhibitory RANKL variant strategy. The RANKL variant homotrimers and heterotrimers with wild-type RANKL do not activate the RANK receptor. The RANKL variants act in a dominant-negative manner by rendering the wild-type RANKL protein inactive through the formation of these heterotrimer species. The bumps and sticks on the engineered RANKL protein symbolize the rationally designed mutations in the small and large binding domains of RANKL that interfere with receptor binding. Through this mechanism of inactivating wild-type RANKL, the dominant-negative inhibitory RANKL variants will exert their therapeutic effects.
Figure 23:
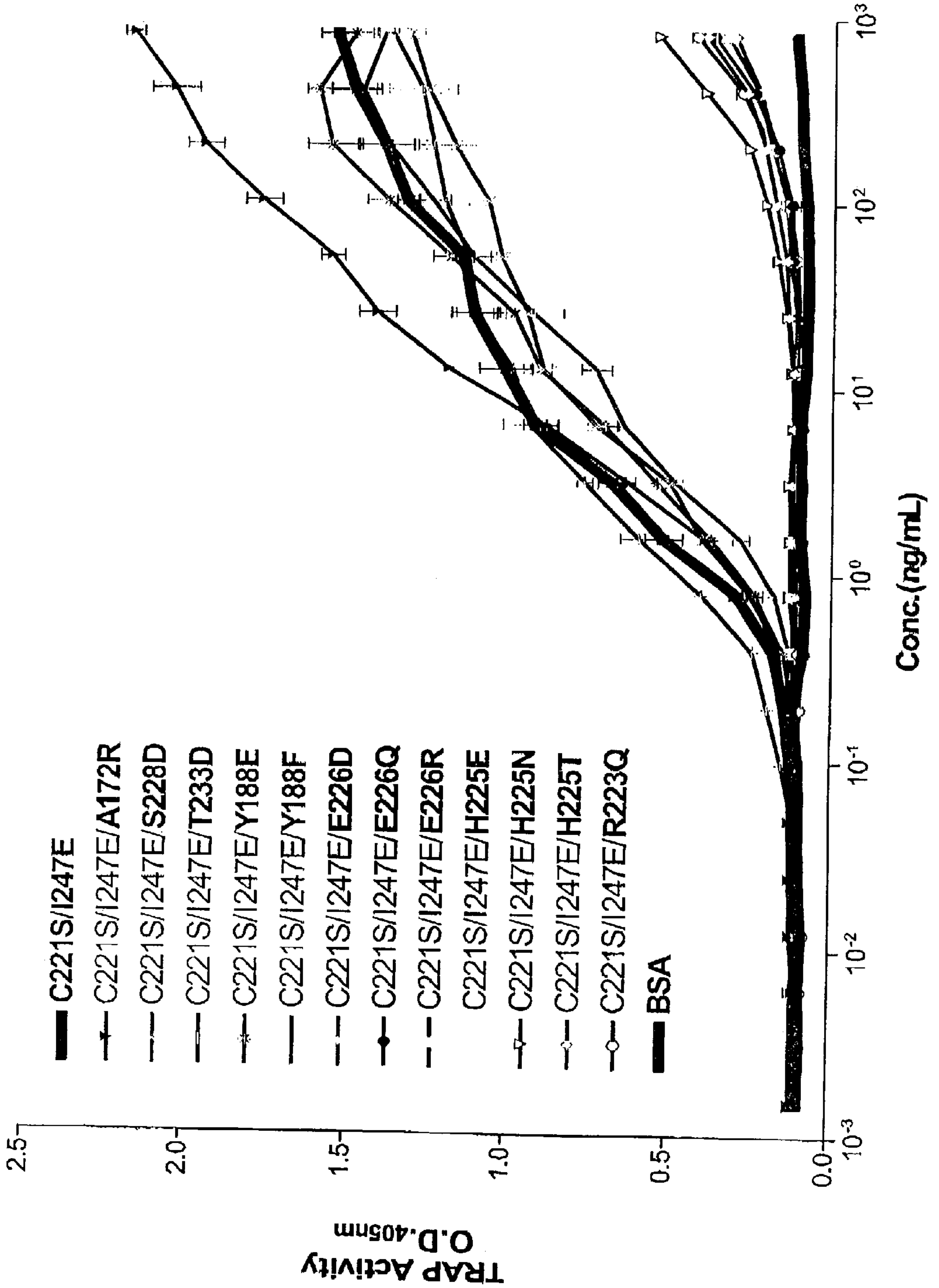
FIG. 23. RANKL variant agonism screen. The ability of RANKL variants to agonize osteoclastogenesis was evaluated by monitoring TRAP levels. TRAP is released from RAW264.7 cells as they undergo RANK-mediated osteoclastogenesis. This experiment identified several non agonizing RANKL variants and one superagonist (RANKL C221S/I247E/A172R).
Figure 24:
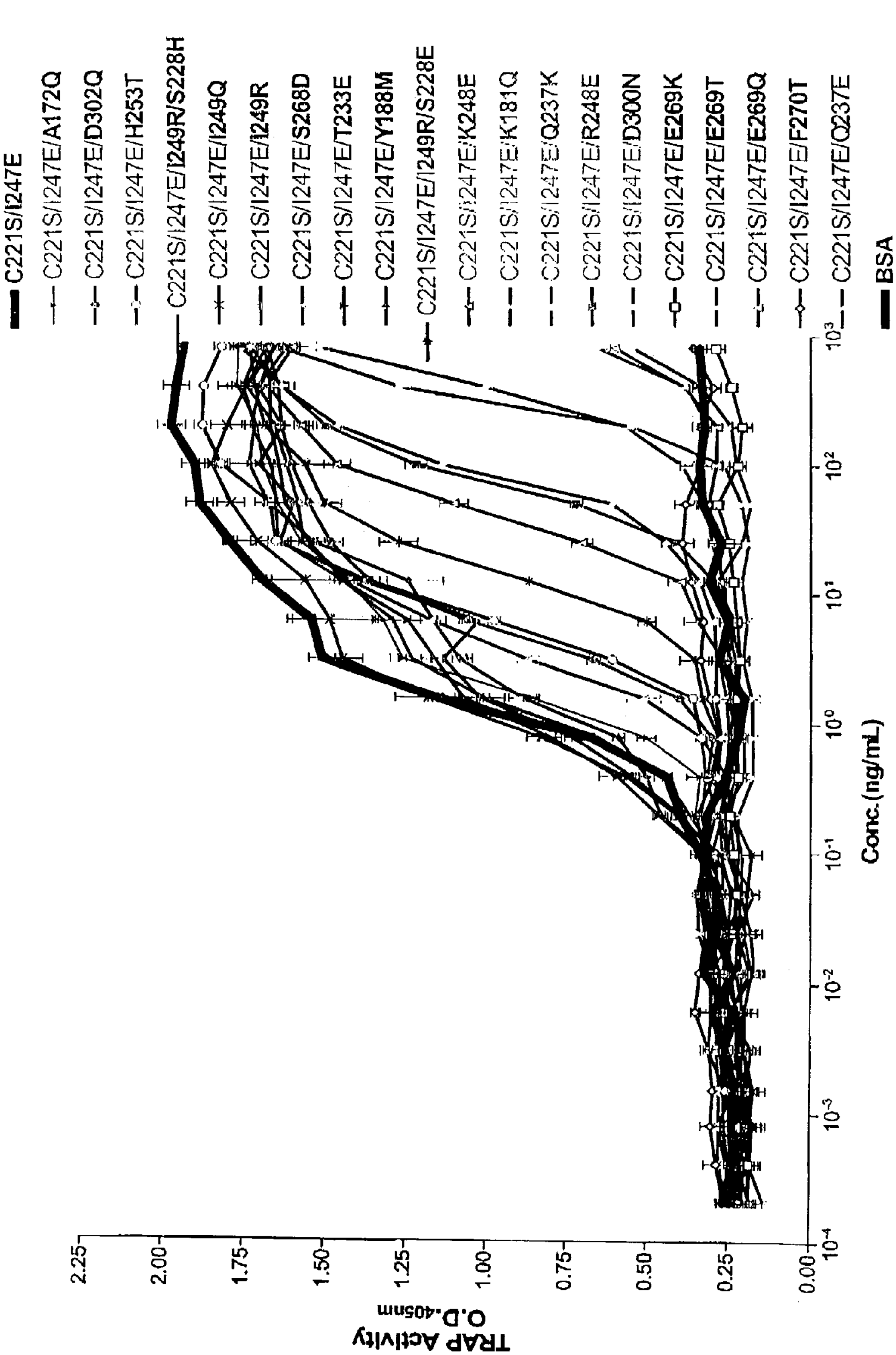
FIG. 24. RANKL variant agonism screen. The ability of RANKL variants to agonize osteoclastogenesis was evaluated by monitoring TRAP levels. TRAP is released from RAW264.7 cells as they undergo RANK-mediated osteoclastogenesis. This experiment identified several non agonizing RANKL variants.
Figure 25:
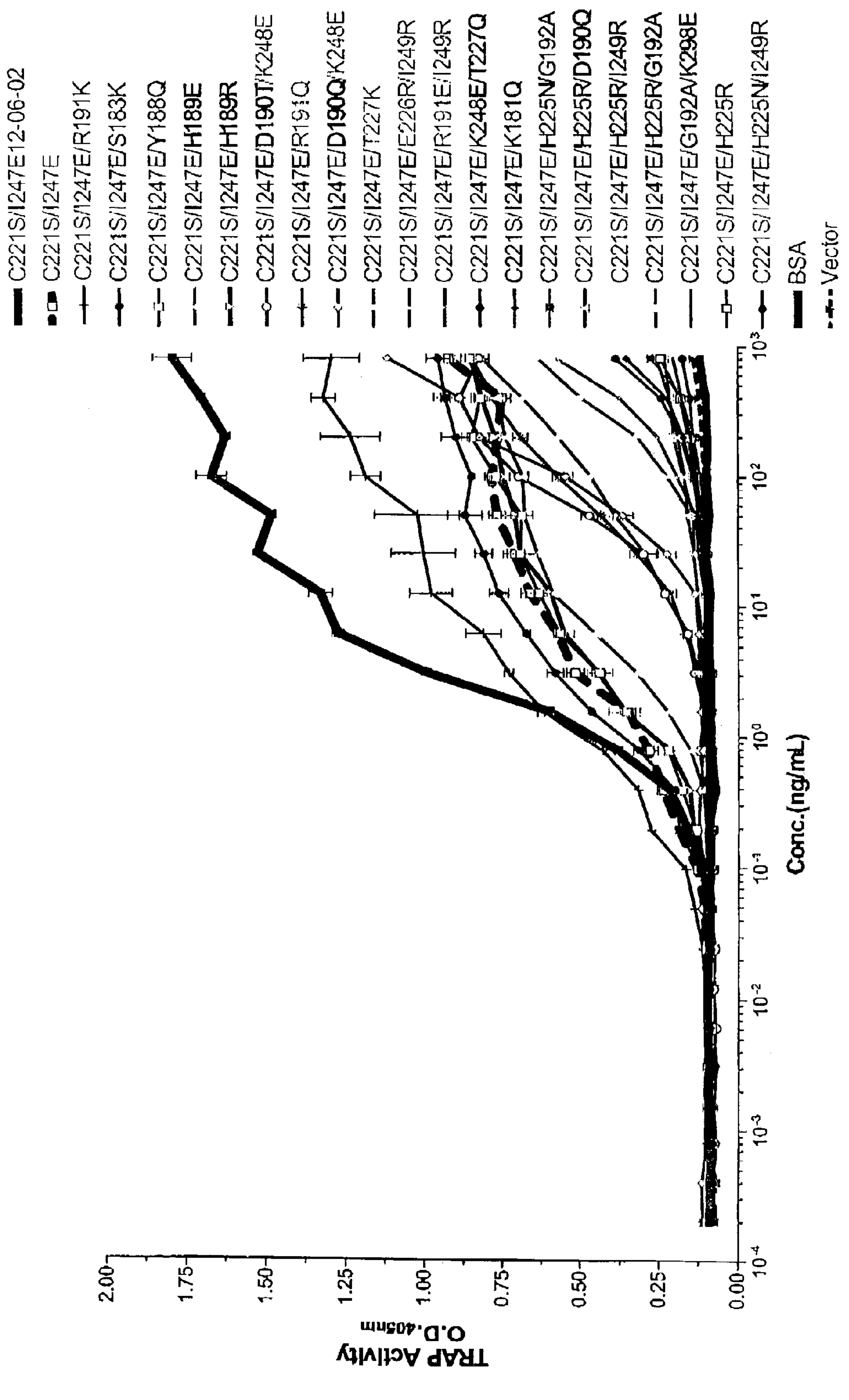
FIG. 25. RANKL variant agonism screen. The ability of RANKL variants to agonize osteoclastogenesis was evaluated by monitoring TRAP levels. TRAP is released from RAW264.7 cells as they undergo RANK-mediated osteoclastogenesis. This experiment identified several non agonizing RANKL variants.
Figure 26:
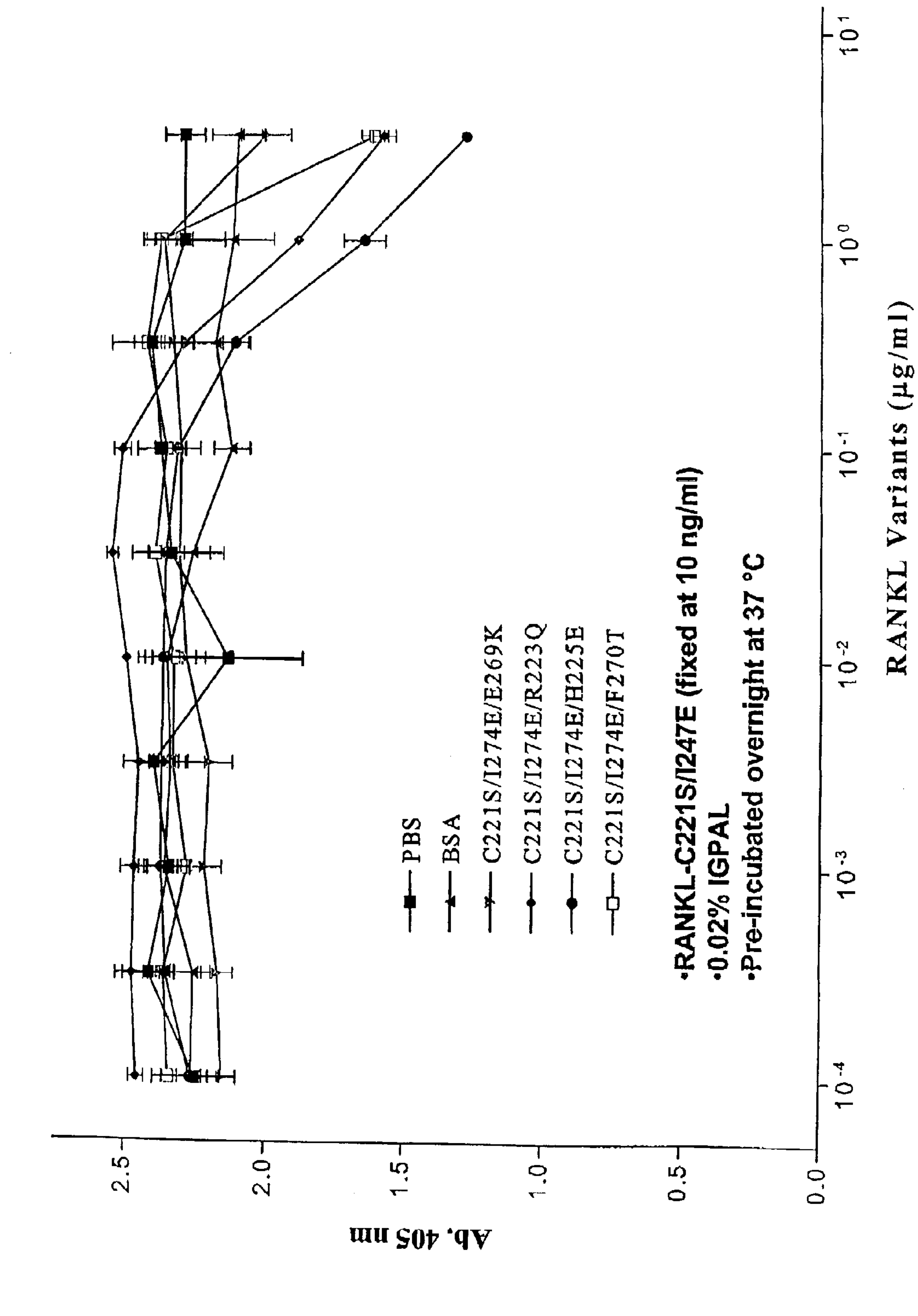
FIG. 26. RANKL variant antagonism screen. The ability of RANKL variants to antagonize osteoclastogenesis was evaluated by monitoring TRAP levels when RANKL-C221S/I247E is mixed with RANKL variants, incubated and added to RAW264.7 cells. TRAP is released from RAW264.7 cells as they undergo RANK-mediated osteoclastogenesis. This experiment identified RANKL variants that antagonized this process.
Figure 27:
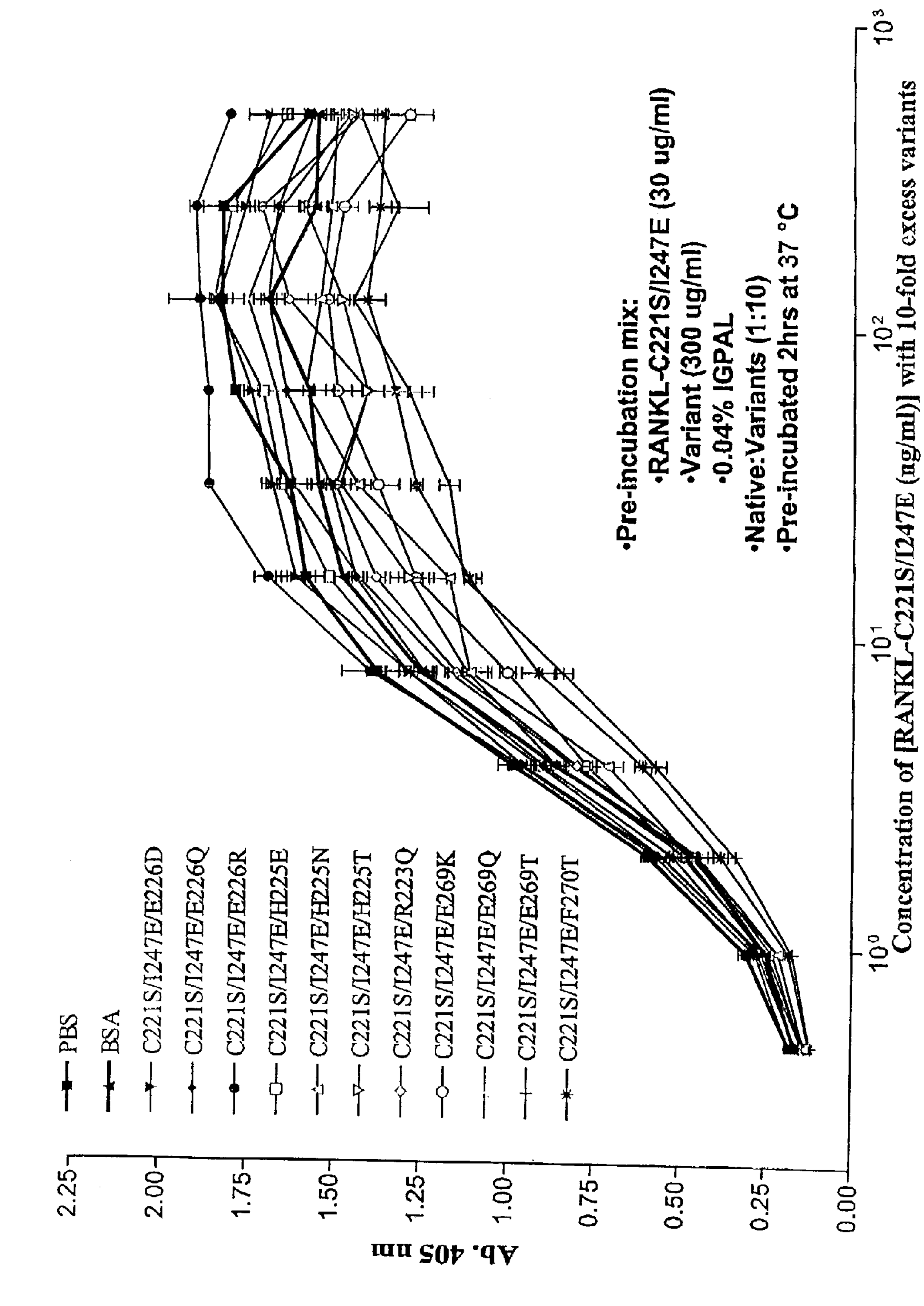
FIG. 27. RANKL variant antagonism screen using a fixed ratio of RANKL-C221S/I247E to ten fold excess variants. The ability of RANKL variants to antagonize osteoclastogenesis was evaluated by monitoring TRAP levels when RANKL-C221S/I247E is mixed with RANKL variants, incubated, diluted over 2 logs, and added to RAW264.7 cells. TRAP is released from RAW264.7 cells as they undergo RANK-mediated osteoclastogenesis. This experiment identified RANKL variants that antagonized this process.
Figure 28:
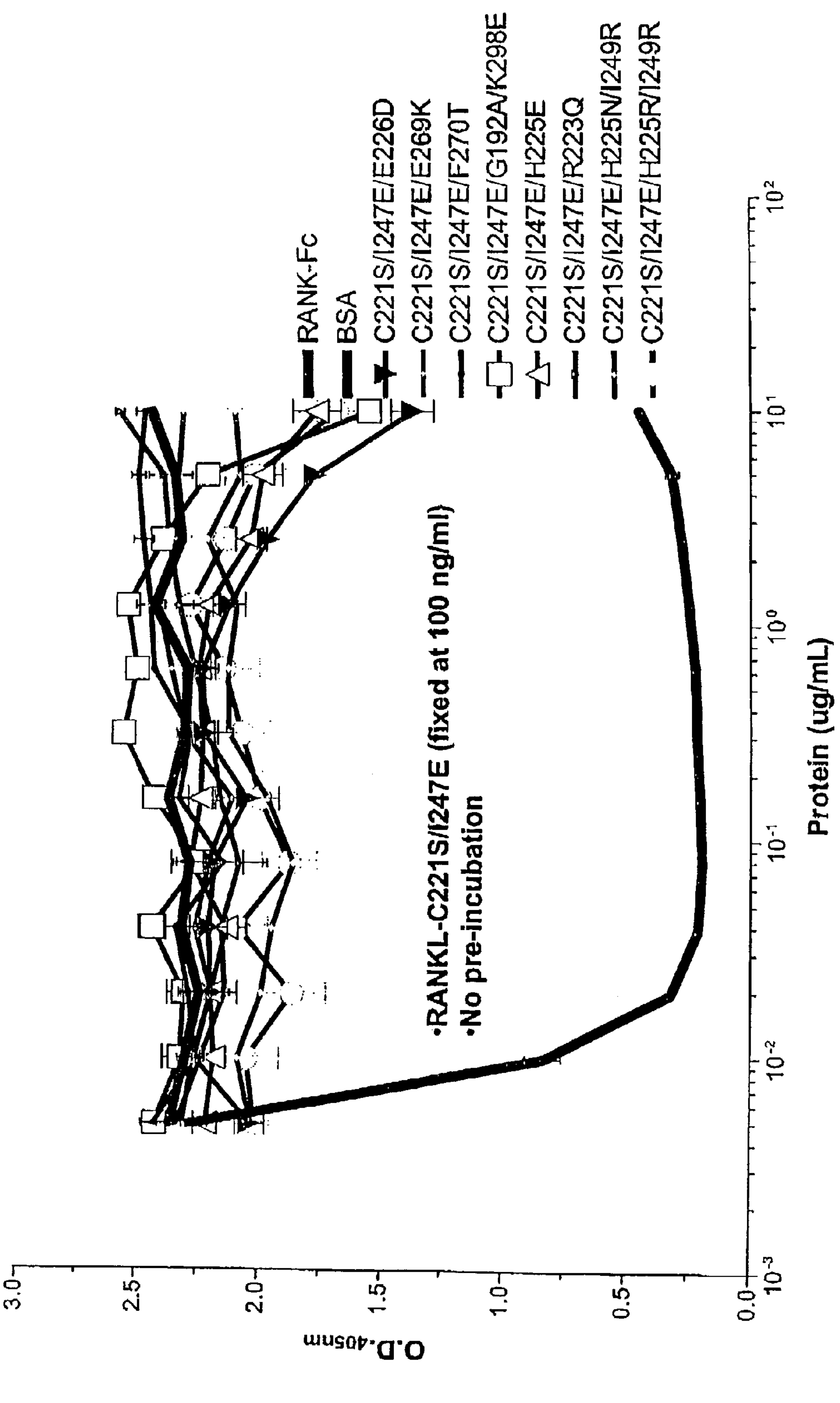
FIG. 28 RANKL variant antagonism screen. The ability of RANKL variants to antagonize osteoclastogenesis was evaluated by monitoring TRAP levels when RANKL-C221S/I247E and RANKL variants are added to RAW264.7 cells without pre-incubation. TRAP is released from RAW264.7 cells as they undergo RANK-mediated osteoclastogenesis. This experiment identified RANKL variants that antagonized this process.

PDA™ was utilized to generate a human structural model of RANKL in addition to selecting amino acids that disrupt RANK binding. The lack of a crystal structure for human OPGL necessitated the creation of a homology model where PDA™ was used for side chain placement based on the human sequence and mouse RANKL structure (PDB# 1JTZ). This modeling was facilitated by the 87% sequence identity between the mouse and human RANKL sequences. The dominant-negative RANKL therapeutic strategy is based on the design of novel RANKL variants that have reduced receptor binding and/or activation properties and the ability to heterotrimerize with wild-type RANKL (FIG. 21). In other words, RANKL variants that do not activate RANK will exchange with wild-type RANKL protein and sequester it into inactive heterotrimers, inhibiting its activity. The number and activity of osteoclasts will be lowered as a result of this treatment leading to a decrease in bone resorption and an overall increase in bone mineral density.

The dominant-negative RANKL variants were designed by substituting the amino acids at key RANKL-RANK contact points with amino acids that disrupt the ability of the ligand to activate receptor. PDA™ technology was used to select appropriate substitutions for optimal protein folding. The exchange of these trimeric RANKL variants with trimeric wild-type RANKL will result in the deactivation of the wild-type RANKL and reduced osteoclast formation. To help accomplish this goal more effectively, the RANKL variants can also be designed to preferentially heterotrimerize with wild-type RANKL. The list of 89 RANKL library variants is found in FIG. 22. Additional libraries based on the combinatorial assembly of these variants and between these variants and the solubility variants (FIG. 2*b*) were also produced.

Single Chain Dominant-Negative Polypeptides

Multiple strategies for covalent linkage of monomers exist. These included, but are not limited to: polypeptide linkages between N and C-termini of two domains, made up of zero or more amino acids (resulting in single chain polypeptides comprising multiple domains); linkage via a disulfide bond between monomers; linkage via chemical crosslinking agents.

Multiple strategies exist for modification of individual domains such that receptor binding is removed (or reduced). These include, but are not limited to: amino acid modifications that create steric repulsion between ligand domain and receptor; modifications that create electrostatic repulsion; modifications that create unfavorable desolvation of amino acids; and chemical modification of amino acids at the ligand/receptor interface (e.g. PEGylation or glycosylation).

Linkage of RANKL Monomers into a Trimer

To improve the dominant negative behavior of these mutants, single-chain dimers between two modified receptor interaction domains are being created.

RANKL Variant Library Construction

The full-length RANKL cDNA was cloned using RT-PCR on lymph node cDNAs. Two lengths of RANKL, amino acids 147 to 317 and 159 to 317, were subcloned into pET33b after PCR-mediated addition of TEV and HIS tags (FIG. 1*b*).

Muatagenesis reactions were performed to introduce the nucleotide changes that result in the desired amino acid substitutions. The mutagenesis reactions utilize pairs of divergent and overlapping oligonucleotides with nucleotide variations that introduce the specific amino acid changes. These oligonucleotides are extended using Pfu polymerase through multiple rounds of thermal cycling and these extension products are transformed into TOP10 bacterial cells after digesting the products with DpnI. Clones were sequenced to confirm the designed changes and to insure no modifications were introduced into the cDNA during the thermal cycling.

RANKL Variant Screening for Non-agonists, Superagonists, and Antagonists

A library of 89 human RANKL variants was constructed with all members of the library comprising the amino acid sequence in FIG. 1*b* and the two solubility-imparting modifications, C221S/I247E in addition to the 89 computationally designed inhibitory modifications from FIG. 22. These 89 human RANKL variant proteins were expressed and purified from *E. coli* and 52 were screened for non-agonists, superagonists, and antagonists in an assay that monitors osteoclastogenesis in RAW264.7 cells (FIGS. 23-30). Treating RAW264.7 cells with the purified human RANKL variant protein and measuring the amount of TRAP released identified non-agonist and superagonist variants (FIG. 29). Of the 52 RANKL variants screened, 21 RANKL variants were identified to be non-agonists, while C221S/I247E/A172R was found to be a superagonist. In addition, the antagonism screens described in FIGS. 26-28 identified the six antagonizing variants listed in FIG. 30. These antagonizing variants have the ability to lower the osteoclastogenesis activity of human RANKL.

Tartrate-Resistant Acid Phosphatase (TRAP) Activity Bioassay

The TRAP activity bioassay was used for assaying non-agonism, super-agonism, and antagonism. TRAP activity was measured after adding the RANKL variant protein to cell lines such as RAW264.7 to identify RANKL variants that are non-agonists or super-agonists (FIGS. 23-25, 29). An additional screen was performed to identify antagonist RANKL variants by mixing RANKL variant protein with one of the active RANKL solubility variants, C221S/I247E, and adding the protein mixture to the RAW264.7 and measuring TRAP activity. Antagonist RANKL variants were identified that lowered the activity of the RANKL solubility variant C221S/I247E (FIGS. 26-28, 30).

RAW 264.7 cells (ATCC#TIB-71) were cultured and maintained in 75 $cm^2$ flasks in 5% $CO_2$ humidified incubator at 37° C. in growth media containing α-MEM w/2 mM L-Glutamine (Gibco-BRL#12571-063), 10% Heat Inactivated Fetal Bovine Serum (FBS) (Hyclone#SH30071.03) and Penicillin/Streptomycin (Gibco-BRL#15140-122) 100 units/ml and 100 µg/ml respectively.

Recombinant mouse RANKL (R&D#462-TR), recombinant human soluble RANKL (Biosource#PHP0034), and recombinant human soluble RANKL variants were diluted to their working concentration in assay media consisting of α-MEM w/I-glutamine (Gibco-BRL#12571-063) supplemented with 10% Heat Inactivated Fetal Bovine Serum (FBS) (Hyclone#SH30071.03) and Penicillin/Streptomycin (Gibco-BRL#15140-122) 100 units/ml and 100 μg/ml respectively. 250 μl of RANKL standards and samples were added to 96-well assay plate in triplicate or quadruplicate, and serially diluted 1:2 by transferring 125 μl into subsequent wells containing 125 μl of assay media.

Aspirating the exhausted media, adding 10 ml of pre-warmed media to the flask, and scraping cells from the flask using a cell scraper harvested the cells. The cells were transferred to a 15 ml conical tube, spun at 1000 rpm for 5 minutes and resuspended in 10 ml of assay media. The cells were counted and seeded at density of $1.5\times10^3$/125 μl/well in 96-well assay plate. Assay plates were incubated at 37° C. in 5% $CO_2$ humidified incubator for 72 hours.

The amount of osteoclast-like cells induced from the RAW 264.7 cells was determined by measuring the Tartrate-Resistant Acid Phosphatase (TRAP) activity. TRAP substrate was prepared by adding 20 mg of p-nitrophenol phosphate (pNPP) (ICN#100878) to 10 ml TRAP buffer pH5.0 (100 mM Sodium Acetate, 11.5 mg/ml Sodium Tartrate (ICN#195503)). The media was aspirated off the assay plate and discarded. Cells were fixed for 1 minute with 1:1 ethanol and acetone solution and washed once with 100-150 μl/well of PBS (Hyclone#SH30256.02). 100 μl of TRAP solution was added to each well, and the plate was incubated at 37° C. for 2 hours. The reaction was stopped by adding 50 μl/well of a 0.2N NaOH solution and the absorbance was read at 405 nm. If the absorbance reached saturation, the solutions were diluted 1:5 and read again.

Tartrate-Resistant Acid Phosphatase (TRAP) Cytological Staining

In parallel experiments, osteoclast formation from the RAW 264.7 cells was measured by the presence of Tartrate-Resistant Acid Phosphatase (TRAP) multinucleated positive cells using cytological staining. 0.1M Acetate buffer was prepared prior to staining by combining 35.2 ml of a 0.2M Sodium Acetate solution, 14.8 ml of a 0.2M Acetic Acid solution and 50 ml of water. 10 ml TRAP buffer pH5.0 (50 mM Acetate Buffer, 30 mM Sodium Tartrate (Sigma#S-8640), 0.1 mg/ml Napthol AS-MX Phosphate Disodium Salt (Sigma#N-5000), 0.1% Triton X-100) was prepared fresh for each assay. The TRAP buffer was warmed in a 37° C. water bath and 0.3 mg/ml of Fast Red Violet LB Stain (Sigma#F-3381) was added and the stain was returned to the 37° C. water bath. The media was aspirated off the assay plate and discarded. The cells were washed once with 150 μl/well of PBS (Hyclone#SH30256.02) and subsequently fixed with 100 μl/well of a 10% Glutaraldehyde solution for 15 minutes at 37° C. The cells were washed twice with 150 μl/well of pre-warmed PBS. 100 μl of the pre-warmed TRAP stain was added to each well and the plate was incubated at 37° C. for 5-10 minutes. The TRAP stain was removed and 100 μl of PBS was added to each well to prevent cells from drying out. TRAP positive multinucleated cells (more than three nuclei) were counted.

We claim:

1. A variant RANKL protein comprising amino acid substitution C221S and at least one substitution selected from the group consisting of: A232K, I207K, I207R, I247A, I247D, I247E, I247K, I247Q, and I247R in SEQ ID NO:1 when numbered as amino acids 68-317 corresponding to the numbering of the full-length wild-type human RANKL sequence.

2. A variant RANKL protein comprising amino acid substitution C221S and at least one amino acid substitution selected from the group consisting of: I207K, I247A, I247D, I247E, I247K and I247Q in SEQ ID NO:1 when numbered as amino acids 68-317 corresponding to the numbering of the full-length wild-type human RANKL sequence.

3. A variant RANKL protein comprising amino acid substitutions C221S/I247E, and at least one set of substitutions selected from the group consisting of: A172R, A172Q, Y188E, Y188F, Y188M, T233D, T233E, S228D, I249Q, I249R, I249R/S228H, H253T, D302Q, S268D, R191K, S183K, H189R, Y188Q, H198E, K181Q, Q237K, K248E, R284E, I249R/S228E, D300N, D190T/K248E, R191Q, T227K, D190Q/K248E, E226R/i249R, R191E/1249R, H225E, H225N, H225T, R223Q, E226D, E226Q, E226R, E269Q, E269T, Q237E, K248E/T227Q, H225R/D1 90Q, H225R/G192A, H225R, H225N/G192A, E269K, F270T, H225N/I249R, H225R/I249R, and G192A/K298E in SEQ ID NO:1 when numbered as amino acids 68-317 corresponding to the numbering of the full-length wild-type human RANKL sequence.

4. A variant RANKL protein according to claims 1, 2 or 3, wherein said variant protein is chemically modified.

5. A RANKL variant protein according to claim 4, wherein said chemical modification is PEGylation.

6. A RANKL variant protein according to claim 4, wherein said chemical modification is glycosylation.

7. A recombinant nucleic acid encoding the protein of claim 1, 2 or 3.

8. An isolated host cell comprising the recombinant nucleic acid of claim 7.

9. A method of producing a non-naturally occurring RANKL protein comprising culturing the host cell of claim 8 under conditions suitable for expression of said nucleic acid.

10. A method according to claim 9, further comprising recovering said RANKL protein.

11. A composition comprising a variant RANKL protein according to claims 2 or 3 and a carrier.

12. A method of making a mixed RANKL oligomer comprising contacting at least one variant RANKL protein comprising at least a variant extracellular domain of a RANKL monomer protein with a homo-oligomer comprising naturally occurring RANKL monomer proteins, under conditions whereby at least one naturally occurring RANKL monomer exchanges with a variant monomer to form a mixed oligomer, and wherein the variant RANKL protein comprises the variant RANKL protein of claim 1, 2 or 3.

* * * * *

SEQUENCE LISTING

```
<160> NUMBER OF SEQ ID NOS: 6

<210> SEQ ID NO 1
<211> LENGTH: 250
<212> TYPE: PRT
<213> ORGANISM: Homo sapiens
<300> PUBLICATION INFORMATION:
<308> DATABASE ACCESSION NUMBER: Genbank Acc. No. AAB86811
<309> DATABASE ENTRY DATE: 1997-11-21
<313> RELEVANT RESIDUES: (68)..(317)

<400> SEQUENCE: 1

Phe Tyr Phe Arg Ala Gln Met Asp Pro Asn Arg Ile Ser Glu Asp Gly
1               5                   10                  15

Thr His Cys Ile Tyr Arg Ile Leu Arg Leu His Glu Asn Ala Asp Phe
            20                  25                  30

Gln Asp Thr Thr Leu Glu Ser Gln Asp Thr Lys Leu Ile Pro Asp Ser
        35                  40                  45

Cys Arg Arg Ile Lys Gln Ala Phe Gln Gly Ala Val Gln Lys Glu Leu
    50                  55                  60

Gln His Ile Val Gly Ser Gln His Ile Arg Ala Glu Lys Ala Met Val
65                  70                  75                  80

Asp Gly Ser Trp Leu Asp Leu Ala Lys Arg Ser Lys Leu Glu Ala Gln
                85                  90                  95

Pro Phe Ala His Leu Thr Ile Asn Ala Thr Asp Ile Pro Ser Gly Ser
            100                 105                 110

His Lys Val Ser Leu Ser Ser Trp Tyr His Asp Arg Gly Trp Ala Lys
        115                 120                 125

Ile Ser Asn Met Thr Phe Ser Asn Gly Lys Leu Ile Val Asn Gln Asp
```

-continued

```
    130                 135                 140

Gly Phe Tyr Tyr Leu Tyr Ala Asn Ile Cys Phe Arg His His Glu Thr
145                 150                 155                 160

Ser Gly Asp Leu Ala Thr Glu Tyr Leu Gln Leu Met Val Tyr Val Thr
                165                 170                 175

Lys Thr Ser Ile Lys Ile Pro Ser Ser His Thr Leu Met Lys Gly Gly
            180                 185                 190

Ser Thr Lys Tyr Trp Ser Gly Asn Ser Glu Phe His Phe Tyr Ser Ile
        195                 200                 205

Asn Val Gly Gly Phe Phe Lys Leu Arg Ser Gly Glu Glu Ile Ser Ile
    210                 215                 220

Glu Val Ser Asn Pro Ser Leu Leu Asp Pro Asp Gln Asp Ala Thr Tyr
225                 230                 235                 240

Phe Gly Ala Phe Lys Val Arg Asp Ile Asp
                245                 250


<210> SEQ ID NO 2
<211> LENGTH: 178
<212> TYPE: PRT
<213> ORGANISM: Artificial sequence
<220> FEATURE:
<223> OTHER INFORMATION: contruct of human RANKL extracellular region
      with histidine tag and TEV protease cleavage site

<400> SEQUENCE: 2

Met Gly His His His His His His Ser Ser Gly Leu Glu Val Leu Phe
1               5                   10                  15

Gln Gly Pro Lys Leu Glu Ala Gln Pro Phe Ala His Leu Thr Ile Asn
            20                  25                  30

Ala Thr Asp Ile Pro Ser Gly Ser His Lys Val Ser Leu Ser Ser Trp
        35                  40                  45

Tyr His Asp Arg Gly Trp Ala Lys Ile Ser Asn Met Thr Phe Ser Asn
    50                  55                  60

Gly Lys Leu Ile Val Asn Gln Asp Gly Phe Tyr Tyr Leu Tyr Ala Asn
65                  70                  75                  80

Ile Cys Phe Arg His His Glu Thr Ser Gly Asp Leu Ala Thr Glu Tyr
                85                  90                  95

Leu Gln Leu Met Val Tyr Val Thr Lys Thr Ser Ile Lys Ile Pro Ser
            100                 105                 110

Ser His Thr Leu Met Lys Gly Gly Ser Thr Lys Tyr Trp Ser Gly Asn
        115                 120                 125

Ser Glu Phe His Phe Tyr Ser Ile Asn Val Gly Gly Phe Phe Lys Leu
    130                 135                 140

Arg Ser Gly Glu Glu Ile Ser Ile Glu Val Ser Asn Pro Ser Leu Leu
145                 150                 155                 160

Asp Pro Asp Gln Asp Ala Thr Tyr Phe Gly Ala Phe Lys Val Arg Asp
                165                 170                 175

Ile Asp


<210> SEQ ID NO 3
<211> LENGTH: 249
<212> TYPE: PRT
<213> ORGANISM: Mus musculus
<300> PUBLICATION INFORMATION:
<308> DATABASE ACCESSION NUMBER: GenBank Acc. No. NP_035743
<309> DATABASE ENTRY DATE: 2002-01-04
<313> RELEVANT RESIDUES: (68)..(316)
```

-continued

<400> SEQUENCE: 3

```
Phe Leu Tyr Phe Arg Ala Gln Met Asp Pro Asn Arg Ile Ser Glu Asp
1               5                   10                  15

Ser Thr His Cys Phe Tyr Arg Ile Leu Arg Leu His Glu Asn Ala Gly
            20                  25                  30

Leu Gln Asp Ser Thr Leu Glu Ser Glu Asp Thr Leu Pro Asp Ser Cys
        35                  40                  45

Arg Arg Met Lys Gln Ala Phe Gln Gly Ala Val Gln Lys Glu Leu Gln
    50                  55                  60

His Ile Val Gly Pro Gln Arg Phe Ser Gly Ala Pro Ala Met Met Glu
65                  70                  75                  80

Gly Ser Trp Leu Asp Val Ala Gln Arg Gly Lys Pro Glu Ala Gln Pro
                85                  90                  95

Phe Ala His Leu Thr Ile Asn Ala Ala Ser Ile Pro Ser Gly Ser His
            100                 105                 110

Lys Val Thr Leu Ser Ser Trp Tyr His Asp Arg Gly Trp Ala Lys Ile
        115                 120                 125

Ser Asn Met Thr Leu Ser Asn Gly Lys Leu Arg Val Asn Gln Asp Gly
    130                 135                 140

Phe Tyr Tyr Leu Tyr Ala Asn Ile Cys Phe Arg His His Glu Thr Ser
145                 150                 155                 160

Gly Ser Val Pro Thr Asp Tyr Leu Gln Leu Met Val Tyr Val Val Lys
                165                 170                 175

Thr Ser Ile Lys Ile Pro Ser Ser His Asn Leu Met Lys Gly Gly Ser
            180                 185                 190

Thr Lys Asn Trp Ser Gly Asn Ser Glu Phe His Phe Tyr Ser Ile Asn
        195                 200                 205

Val Gly Gly Phe Phe Lys Leu Arg Ala Gly Glu Glu Ile Ser Ile Gln
    210                 215                 220

Val Ser Asn Pro Ser Leu Leu Asp Pro Asp Gln Asp Ala Thr Tyr Phe
225                 230                 235                 240

Gly Ala Phe Lys Val Gln Asp Ile Asp
                245
```

<210> SEQ ID NO 4
<211> LENGTH: 5
<212> TYPE: PRT
<213> ORGANISM: Artificial sequence
<220> FEATURE:
<223> OTHER INFORMATION: linker consensus sequence

<400> SEQUENCE: 4

```
Gly Ser Gly Gly Ser
1               5
```

<210> SEQ ID NO 5
<211> LENGTH: 5
<212> TYPE: PRT
<213> ORGANISM: Artificial sequence
<220> FEATURE:
<223> OTHER INFORMATION: linker consensus sequence

<400> SEQUENCE: 5

```
Gly Gly Gly Gly Ser
1               5
```

<210> SEQ ID NO 6
<211> LENGTH: 4

-continued

```
<212> TYPE: PRT
<213> ORGANISM: Artificial sequence
<220> FEATURE:
<223> OTHER INFORMATION: linker consensus sequence

<400> SEQUENCE: 6

Gly Gly Gly Ser
1
```